(12) United States Patent
Azhir et al.

(10) Patent No.: US 12,329,776 B2
(45) Date of Patent: Jun. 17, 2025

(54) TREATMENT METHODS FOR ALS PATIENTS

(71) Applicants: Neuvivo, Inc., Palo Alto, CA (US); The Regents of the University of California, Oakland, CA (US)

(72) Inventors: Arasteh Azhir, Los Altos, CA (US); Michael S. McGrath, Meadow Vista, CA (US); Bruce D. Forrest, Nyack, NY (US); Leah Price, Karmiel (IL)

(73) Assignees: NEUVIVO, INC., Palo Alto, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/167,245

(22) Filed: Feb. 10, 2023

(65) Prior Publication Data
US 2023/0190790 A1 Jun. 22, 2023

Related U.S. Application Data

(63) Continuation of application No. PCT/US2022/077557, filed on Oct. 4, 2022.

(60) Provisional application No. 63/302,000, filed on Jan. 21, 2022, provisional application No. 63/301,476, filed on Jan. 20, 2022, provisional application No. 63/252,061, filed on Oct. 4, 2021.

(51) Int. Cl.
*A61K 33/20* (2006.01)
*A61K 9/08* (2006.01)
*A61P 25/28* (2006.01)

(52) U.S. Cl.
CPC ........... *A61K 33/20* (2013.01); *A61K 9/08* (2013.01); *A61P 25/28* (2018.01)

(58) Field of Classification Search
CPC combination set(s) only.
See application file for complete search history.

(56) References Cited

U.S. PATENT DOCUMENTS

| | | |
|---|---|---|
| 7,105,183 B2 | 9/2006 | Mcgrath |
| 8,029,826 B2 | 10/2011 | Mcgrath |
| 8,067,035 B2 | 11/2011 | Boulanger et al. |
| 8,231,856 B2 | 7/2012 | Boulanger et al. |
| 8,501,244 B2 | 8/2013 | Boulanger et al. |
| 9,266,734 B2 | 2/2016 | Boulanger et al. |
| 9,364,501 B2 | 6/2016 | Mcgrath |
| 9,579,346 B2 | 2/2017 | Mcgrath et al. |
| 9,839,650 B2 | 12/2017 | Boulanger et al. |
| 12,109,228 B2 | 10/2024 | Norviel et al. |
| 12,109,229 B2 | 10/2024 | Norviel et al. |
| 12,109,230 B2 | 10/2024 | Norviel et al. |
| 12,109,231 B2 | 10/2024 | Norviel et al. |
| 2006/0051790 A1 | 3/2006 | Geschwind et al. |
| 2007/0145328 A1 * | 6/2007 | Boulanger ............. A61P 31/12 252/187.21 |
| 2008/0274118 A1 | 11/2008 | Aukerman et al. |
| 2011/0086894 A1 | 4/2011 | Bowser |
| 2012/0134929 A1 | 5/2012 | Mcgrath et al. |
| 2012/0295296 A1 | 11/2012 | Mcgrath |
| 2014/0147856 A1 | 5/2014 | Forsyth et al. |
| 2014/0178420 A1 | 6/2014 | Goldberg et al. |
| 2015/0258069 A1 * | 9/2015 | Voudouris ........... A61K 9/0019 |
| 2019/0060359 A1 | 2/2019 | Norviel et al. |
| 2023/0172974 A1 | 6/2023 | Norviel et al. |
| 2023/0181629 A1 | 6/2023 | Norviel et al. |
| 2023/0190789 A1 | 6/2023 | Norviel et al. |
| 2023/0218662 A1 | 7/2023 | Norviel et al. |
| 2024/0261324 A1 | 8/2024 | Norviel et al. |
| 2024/0261325 A1 | 8/2024 | Norviel et al. |
| 2024/0261326 A1 | 8/2024 | Norviel et al. |
| 2024/0269168 A1 | 8/2024 | Norviel et al. |

FOREIGN PATENT DOCUMENTS

| | | | |
|---|---|---|---|
| AU | 2011205095 A1 * | 8/2011 | ............ A61K 33/00 |
| WO | WO-2008042190 A2 | 4/2008 | |
| WO | WO-2014057880 A1 | 4/2014 | |
| WO | WO-2015006489 A1 | 1/2015 | |
| WO | WO-2015175974 A1 | 11/2015 | |
| WO | WO-2017079161 A2 | 5/2017 | |
| WO | WO-2022245209 A2 | 11/2022 | |
| WO | WO-2023060097 A1 | 4/2023 | |
| WO | WO-2023230538 A2 | 11/2023 | |

OTHER PUBLICATIONS

Miller RG, Block G, Katz JS, Barohn RJ, Gopalakrishnan V, Cudkowicz M, Zhang JR, McGrath MS, Ludington E, Appel SH, Azhir A. Neurol Neuroimmunol Neuroinflamm. Apr. 9, 2015;2(3):e100. doi: 10.1212/NXI.0000000000000100. PMID: 25884010; PMCID: PMC4396529. (Year: 2015).*

Thomas Scientific, https://www.thomassci.com/Laboratory-Supplies/Sampling-Serum-Bottles/_/Sterile-Empty-Vial-Clear?q=20A00M599 (Year: 2023).* https://www.thomassci.com/Laboratory-Supplies/Sample-Vials/_/Depyrogenated-Sterile-Empty-Vials (Year: 2018).*

(Continued)

*Primary Examiner* — Adam Weidner
*Assistant Examiner* — Laura Ann Essex
(74) *Attorney, Agent, or Firm* — WILSON SONSINI GOODRICH & ROSATI

(57) ABSTRACT

Provided herein are methods and compositions for the treatment of ALS using chlorite or a pharmaceutical composition comprising sodium chlorite, for a target ALS patient population. Also provided herein are methods for identifying a target ALS patient population likely to be responsive to treatment with chlorite or a pharmaceutical composition comprising sodium chlorite, the methods including identifying ALS patients with elevated plasma C-reactive protein (CRP) levels and/or patients age 40-65, sporadic ALS pathology, or combinations thereof.

11 Claims, 9 Drawing Sheets

(56) References Cited

OTHER PUBLICATIONS

Nzwalo H, de Abreu D, Swash M, Pinto S, de Carvalho M. Delayed diagnosis in ALS: the problem continues. J Neurol Sci. Aug. 15, 2014;343(1-2): 173-5. doi: 10.1016/j.jns.2014.06.003. Epub Jun. 12, 2014. PMID: 24972820. (Year: 2014).*

Kim YM, Lim BG, Kim H, Kong MH, Lee MK, Lee IO. Slow injection of nefopam reduces pain intensity associated with intravenous injection: a prospective randomized trial. J Anesth. Jun. 2014;28(3):399-406. doi: 10.1007/s00540-013-1744-z. Epub Nov. 8, 2013. PMID: 24201414. (Year: 2014).*

Alzforum. "In ALS, Respiratory Measure Predicts Pace of Disease." Webpage. https://www.alzforum.org/news/research-news/als-respiratory-measure-predicts-pace-disease. Dec. 1, 2017.

Burdo, T.H., et al., Soluble CD163 Made by Monocyte/Macrophages Is a Novel Marker of HIV Activity in Early and Chronic Infection Prior to and After Anti-retroviral Therapy. The Journal of Infectious Diseases 204:154-163 (2011).

Cederbaum et al., The ALSFRS-R: a revised ALS functional rating scale that incorporates assessments of respiratory function. Bdnf Als Study Group (Phase III). J Neurol Sci 169(1-2):13-21 (1999).

Dyken, et al. Neurodegenerative diseases of infancy and childhood. Ann Neurol. Apr. 1983;13(4):351-64.

Galimberti, D. et al. Inflammatory molecules in Frontotemporal Dementia: Cerebrospinal fluid signature of progranulin mutation carriers. Brain Behavior and Immunity 49:182-187 (2015).

Joyce NC, Carter GT. Electrodiagnosis in Amyotrophic Lateral Sclerosis. Published in final edited form as: Electrodiagnosis in persons with amyotrophic lateral sclerosis. Pm R. May 2013;5(5 Suppl): S89-95. Epub Mar. 21, 2013.

Kale, S. et al. Osteopontin signaling upregulates cyclooxygenase-2 expression in tumor-associated macrophages leading to enhanced angiogenesis and melanoma growth via a9b1 integrin. Oncogene 33:2295-2306(2014).

Khazen, et al. Expression of macrophage-selective markers in human and rodent adipocytes. FEBS Lett. Oct. 24, 2005;579(25):5631-4.

Luo et al., Bioluminescence analysis of Smad-dependent TGF-beta signaling in live mice. Methods Mol Biol 574:193-202 (2009).

Luo et al., Bioluminescence imaging of Smad signaling in living mice shows correlation with excitotoxic neurodegeneration. PNAS 103(48): 18326-18331 (2006).

Mackenzie IR. The neuropathology and clinical phenotype of FTD with progranulin mutations. Acta Neuropathol. Jul. 2007;114(1):49-54.

Miller RG, et al. Phase 2B randomized controlled trial of NP001 in amyotrophic lateral sclerosis: Pre-specified and post hoc analyses. Muscle Nerve. Jul. 2022;66(1):1-11. Epub Jun. 3, 2022.

Miller, R.G., et al., Randomized phase 2 trial of NP001-a novel immune regulator: Safety and early efficacy in ALS. Neurology 2:e100:1-9 (2015).

Miller, Robert G. et al., NP001 regulation of macrophage activation markers in ALS: A phase I clinical and biomaker study. Amyotrophic Lateral Sclerosis and Frontotemporal Degeneration 15:601-609 (2014).

Minami et al., Progranulin protects against amyloid β deposition and toxicity in Alzheimer's disease mouse models. Nat Med 20(10):1157-1164 (2014).

Orsini, M. et al., Frontotemporal dementia in amyotrophic lateral sclerosis: from rarity to reality? Neurology International 8:6534:1-3 (2016).

PCT/US2022/077557 International Search Report and Written Opinion dated Mar. 14, 2023.

Qin et al., NADPH oxidase and aging drive microglial activation, oxidative stress, and dopaminergic neurodegeneration following systemic LPS administration. Glia 61(6):855-868 (2013).

Simeonovska Joveva E, et al. Differential diagnosis between Bulbospinal muscular atrophy-Kennedy's disease and Amyotrophic lateral sclerosis. Acta Medica Medianae. Jun. 6, 2019;58(2):77-81.

Uher et al., An inflammatory biomarker as a differential predictor of outcome of depression treatment with escitalopram and nortriptyline. Am J Psychiatry 171(12):1278-1286 (2014).

Walker KA, et al. The association of mid-to late-life systemic inflammation with white matter structure in older adults: The ARIC Study. Neurobiol Aging. Aug. 2018;68:26-33. Epub Apr. 4, 2018.

Yin, F. et al., Exaggerated inflammation, impaired host defense, and neurophathology in progranulin-deficient mice. J. Exp. Med. 207(1):117-128 (2009).

Zhang R, et al.. Macrophage-Targeted Sodium Chlorite (NP001) Slows Progression of Amyotrophic Lateral Sclerosis (ALS) through Regulation of Microbial Translocation. Biomedicines. Nov. 12, 2022;10(11):2907.

PCT/US2016/059915 International Search Report and Written Opinion dated Apr. 17, 2017.

Cellura et al. Factors affecting the diagnostic delay in amyotrophic lateral sclerosis. Clin Neurol Neurosurg 114(6):550-554 (2012).

Co-pending U.S. Appl. No. 18/824,610, inventors Norviel; Vernon A. et al., filed on Sep. 4, 2024.

Co-pending U.S. Appl. No. 18/980,447, inventors Araseth; Azhir et al., filed on Dec. 13, 2024.

Co-pending U.S. Appl. No. 19/011,989, inventors Norviel; Vernon A. et al., filed on Jan. 7, 2025.

Grauers, S. et al. Propofol infusion rate does not affect local pain on injection. Acta Anaesthesiol Scand 46(4):361-3 (2002).

Scott, R. P. et al. Propofol: clinical strategies for preventing the pain of injection. Anaesthesia 43(6):492-494 (1988).

Shimizu, T. et al. Rapid injection reduces pain on injection with propofol. Eur J. Anaesthesiol 22(5):394-396 (2005).

* cited by examiner

N = Number of participants.
ET = Early Termination.
AE = Adverse Event.

TREATMENT METHODS FOR ALS PATIENTS

CROSS-REFERENCE TO RELATED APPLICATIONS

This application is a continuation of International Application PCT/US22/77557, filed Oct. 4, 2022, which claims the benefit of U.S. Provisional Patent Application No. 63/252,061, filed on Oct. 4, 2021, and U.S. Provisional Patent Application No. 63/301,476, filed on Jan. 20, 2022, and U.S. Provisional Patent Application No. 63/302,000, filed on Jan. 21, 2022, which are each incorporated by reference herein in their entireties and for all purposes as if set forth fully herein.

BACKGROUND

Amyotrophic lateral sclerosis (ALS) is a progressive neurodegenerative disease that destroys motor neurons in the brain and spinal cord, eventually leading to muscle paralysis, and death, usually within 2-4 years of diagnosis. There is no cure for ALS, and no effective treatment. While there are two approved drugs for use in ALS patients which may extend life for a short time, or slow progression in a small fraction of very recently diagnosed patients, most ALS patients lack any sort of effective treatment.

SUMMARY

While a formulation of purified sodium chlorite, NP001, was not effective in treating all ALS patients, a portion of ALS patients treated with NP001 experience halted or slowed disease progression. Considering the lack of any effective treatment for ALS, methods of identifying what ALS patients are likely to respond to NP001 may provide an effective treatment for a subpopulation of ALS patients.

Responsive to this need, disclosed herein are methods for identifying and treating a subpopulation of ALS patients likely to be responsive to treatment with NP001 (purified sodium chlorite), who may experience halted or slowed disease progression upon treatment. As there is no effective treatment for ALS, such a treatment which halts or slows disease progression among a subpopulation of ALS patients represents a significant advancement in the treatment of ALS.

In one aspect, provided herein are methods of treating amyotrophic lateral sclerosis (ALS) in a subject aged 40 to 65 years, the method comprising administering intravenously to the subject a chlorite composition comprising purified sodium chlorite, wherein the chlorite composition is administered at 2 mg chlorite per kg of the subject's body weight, wherein the chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5. The purity of the sodium chlorite may be determined by ion chromatography. The method may slow progression of the subject's ALS, or loss of the subject's functions, or loss of the subject's vital capacity. The chlorite composition may be administered over a 60-minute period. The subject may have a plasma C-reactive protein (CRP) level of at least 1.13 mg/L or at least 3.0 mg/L. The subject may have a plasma hs-CRP level of at least 1.13 mg/L or at least 3.0 mg/L. The subject may have experienced a symptom of ALS for at least 18 months prior to administering the chlorite composition to the subject, and optionally the symptom of ALS comprises muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof. The subject may have sporadic ALS pathology and/or does not have an inherited ALS pathology. The subject may not have a mutation in an ALS-associated gene, wherein the mutation may be in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD.

In a further aspect, provided herein are methods of treating amyotrophic lateral sclerosis (ALS) in a subject with a plasma C-reactive protein (CRP) level of at least 1.13 mg/, the method comprising administering intravenously to the subject a chlorite composition comprising purified sodium chlorite, wherein the chlorite composition is administered at 2 mg chlorite per kg of the subject's body weight, wherein the chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5. The subject may be 40 to 65 years old. The chlorite composition may be administered over a 60-minute period.

In another aspect, provided herein are methods of treating amyotrophic lateral sclerosis (ALS) in a subject with a plasma hs-CRP level of at least 1.13 mg/, the method comprising administering intravenously to the subject a chlorite composition comprising purified sodium chlorite, wherein the chlorite composition is administered at 2 mg chlorite per kg of the subject's body weight, wherein the chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5. The subject may be 40 to 65 years old. The chlorite composition may be administered over a 60-minute period.

In a further aspect, provided herein are methods of treating amyotrophic lateral sclerosis (ALS) in a subject years, the method comprising administering intravenously over a 60-minute period to the subject a chlorite composition comprising purified sodium chlorite, wherein the chlorite composition is administered at 2 mg chlorite per kg of the subject's body weight, wherein the chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5. The purity of the sodium chlorite may be determined by ion chromatography. The subject may have a plasma hs-CRP level of greater than 1.13 mg/L and/or the subject may be 40 to 65 years old.

In another aspect, provided herein are methods of treating amyotrophic lateral sclerosis (ALS) in a subject, the method comprising administering intravenously to the subject a chlorite composition comprising purified sodium chlorite, wherein the chlorite composition is administered at 2 mg chlorite per kg of the subject's body weight, wherein the chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5, and wherein the subject has at least one ALS response factor selected from: (a) age 40 to 65 years, (b) plasma hs-CRP level of at least 1.13 mg/L, (c) experienced a symptom of ALS for at least 18 months prior to administration of the chlorite composition, (d) no inherited ALS pathology; (e) no mutation in an ALS-associated gene; and no mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD. In a further aspect, a method of treating amyotrophic lateral sclerosis (ALS) in a subject may comprise administering intravenously to the subject a chlorite composition comprising purified sodium chlorite, wherein the chlorite composition is administered at 4 mg chlorite (or greater) per kg of the subject's body weight, wherein the chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the chlorite composition comprises dibasic sodium phosphate and has a pH between 7.5 and 9.5, and wherein the subject has at least one ALS response factor selected from: (a) age 40 to 65 years, (b) plasma hs-CRP level of at least 1.13 mg/L, (c) experienced a symptom of ALS for at least 18 months prior to administration of the chlorite composition, (d) no inherited ALS pathology; (e) no mutation in an ALS-associated gene; and no mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
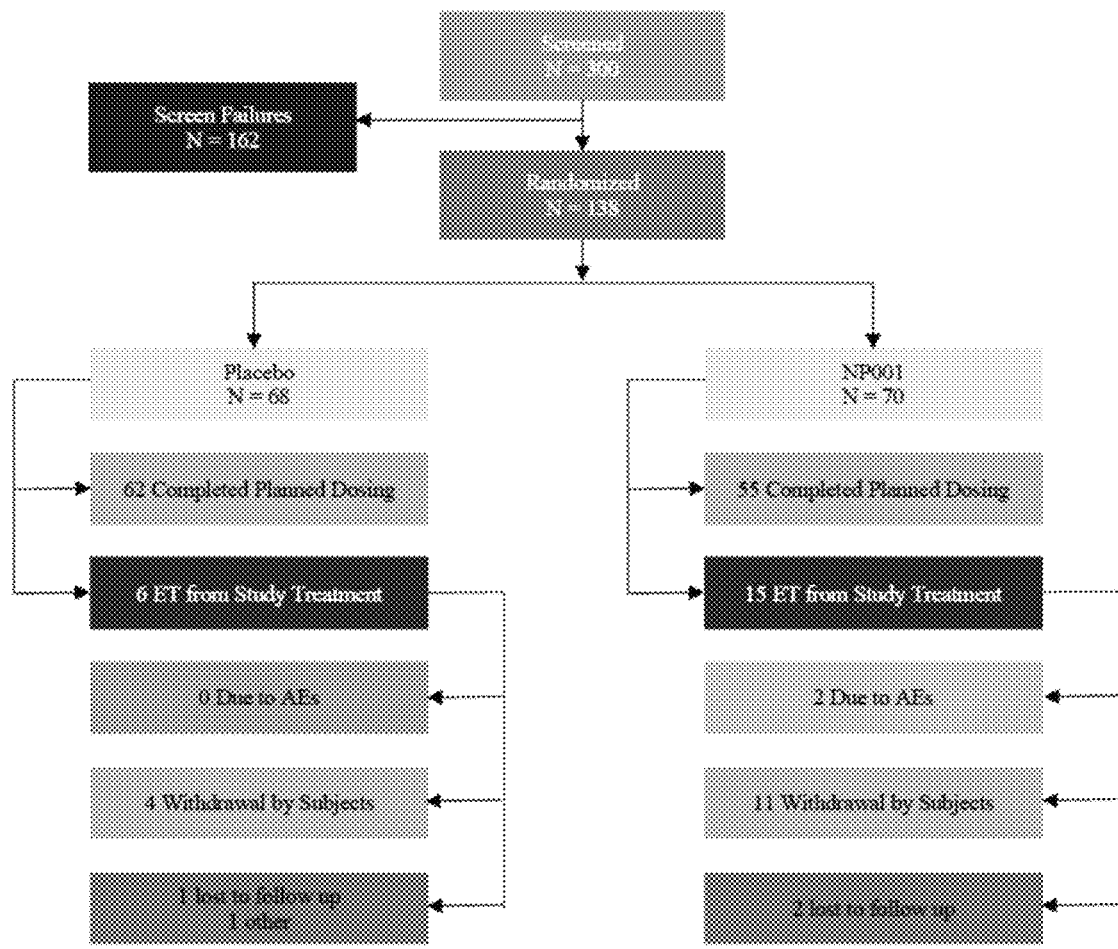
FIG. 1 shows a flow chart summarizing subject distribution within the trial.

The present application describes ALS pathology and interaction with a pharmaceutical composition comprising sodium chlorite (NP001), explaining a plausible mechanism of action for treatment of ALS with a pharmaceutical composition comprising sodium chlorite (NP001), and describes the ALS patient subpopulations likely to be responsive to treatment with a pharmaceutical composition comprising sodium chlorite (NP001). The application further describes ALS symptoms and identification of symptom onset; evaluation of ALS patients using the ALSFRS-R rating scale; quantification of patient plasma CRP levels; quantification of patient vital capacity; methods of treatment with a pharmaceutical composition comprising sodium chlorite (NP001); preparation of chlorite compounds; and chlorite pharmaceutical formulations. Finally, the application will set forth representative examples of a pharmaceutical composition comprising sodium chlorite (NP001) treatment efficacy in various ALS patient subpopulations, and supporting data.

ALS Pathology & Interaction with a Pharmaceutical Composition Comprising Sodium Chlorite (NP001) as an Oxidizer & Immune System Regulator Amyotrophic lateral sclerosis (ALS) is a fatal neurodegenerative disease associated with inappropriate immune system dysfunction involving NF-kB activation, proinflammatory factor production and progressive changes in motor neuron function. Factors elaborated by spinal cord microglia have been identified that both damage and inhibit repair of neurons injured by the accumulation of misfolded proteins as a general model. The recent description of ALS patient monocyte subsets becoming more activated over time as reflected by HLA-DR cell surface levels confirms our earlier studies implicating innate immune dysfunction in disease progression. Therefore, drugs that interfere with or regulate this process could have a therapeutic impact on disease.

The causes of ALS remain largely unknown, however data implicates inflammation and immune system dysregulation in the progression of ALS, including the presence of activated macrophages in ALS patients. Compounds which can reduce inflammation and immune system dysregulation, possibly by returning macrophages to their inactivated state, may be effective in treating ALS.

Macrophages are white blood cells produced by the division of monocytes, and monocytes and macrophages are phagocytes, and play a role in innate immunity (non-specific immune defenses) as well as helping to initiate adaptive immunity (specific defense mechanisms). These cells phagocytose (engulf and then digest) cellular debris and pathogens either as stationary or as mobile cells. When activated by pathogens or by other mechanisms, macrophages stimulate and recruit lymphocytes and other immune cells to respond. Activated macrophages are involved in the progression of a number of diseases and disorders, including, amyotrophic lateral sclerosis (ALS). Activated macrophages elicit massive leukocyte infiltration and flood the surrounding tissue with inflammatory mediators, pro-apoptotic factors, and matrix degrading proteases. These actions can result in inflammation that can dismantle tissues to the point of inflicting serious injury. Tissue destruction perpetrated by macrophage-induced inflammation, a form of immune system dysregulation, has been associated with the progression of the degenerative disease ALS.

Oxidative agents such as chlorite can return macrophages to their inactivated state, and chlorite may be used to treat various diseases or conditions where immune system dysregulation is implicated in disease pathology.

For example, chlorite may be used to treat amyotrophic lateral sclerosis (ALS), a macrophage-related disease. However, the effectiveness of the chlorite treatment can vary within the ALS patient population. A pharmaceutical composition comprising sodium chlorite (NP001) may comprise an intravenous (iv) formulation of pH adjusted purified sodium chlorite which, without being bound to a particular theory, may be converted rapidly into taurine chloramine a known regulator of nuclear factor kappa B (NFkB) activation. Chloramine levels in macrophages increase rapidly and remain elevated in vitro, and in vivo immune regulatory activity has been documented to last weeks. Unlike an anti-inflammatory drug such as hydrocortisone, chlorite does not cause global immune suppression, but a redirection of activation towards a wound healing, phagocytic state through upregulation of heme-oxygenase 1 (HO1).

Sodium chlorite is noteworthy as an oxidizer utilized in the treatment of diseases where inflammation and immune system dysregulation are believed to be significant contributing factors in disease progression, including ALS. For instance, activated macrophages are believed to be a form of immune system dysregulation involved in the progression of ALS, as they elicit massive leukocyte infiltration and flood the surrounding tissue with inflammatory mediators, pro-apoptotic factors, and matrix degrading proteases. These actions can result in inflammation that can dismantle tissues to the point of inflicting serious injury. Tissue destruction perpetrated by macrophage-induced inflammation, a form of immune system dysregulation, has been associated with the progression of the neurodegenerative disease ALS. In the presence of heme associated iron, presumably from the NADPH oxidase complex on the surface of phagocytic cells, sodium chlorite is converted from a prodrug through a hypochlorite intermediate, to an intracellular form of taurine chloramine (TauCl). TauCl is a long-lived effector molecule within macrophages that down-regulates NF-kB expression and inhibits production of pro-inflammatory cytokines in part through activation of heme oxygenase-1 (HO-1).

ALS patients can be defined by four generalized patient groups: slowly progressive, fast progressive, early disease presentations, and late disease presentations. Challenges associated with developing a treatment for ALS include clinical trials which mix together various members of the ALS patient population from these categories, particularly when recruited from the earliest time of disease onset. This has generally been the approach to clinical trial patient selection, as it has been thought that treatment outcomes are likely to be better if introduced early in disease progression. However, there are characteristics of the different ALS patient groups that may impact the ability to determine whether any drug has subset specific activities important for the regulation of ALS disease in that ALS patient group, which may not be present in another or every other ALS patient group. Given the small sizes typical of ALS trials, the presence of even a small number of individuals with confounding characteristics might lead to failure of a drug that if appropriately targeted might have disease modification activities documented. Additional problems with past clinical trials also include relying on only one positive clinical outcome category to assess the general efficacy of a drug for ALS, for example, ALSFRS-R score, and it may be beneficial to measure multiple clinical outcome categories to assess ALS drug efficacy, as disclosed and embodied in some methods of patient selection herein.

Of the four categories, only the subset termed slowly progressive appears to have a component of inflammation as a significant aspect of ALS disease pathology. The slowly progressive subsets' association with inflammation is inferred upon study of ALS in association with CRP levels over time from diagnosis. The longer an ALS patient lives after diagnosis, the higher the plasma CRP. There is a large subgroup of ALS patients with evidence for ongoing, and potentially growing inflammation associated with a slower rate of progression to that seen in standard ALS clinical trials recruiting the very earliest patients. In the context of drug development targeting ALS patients wherein inflammation might play a pathogenic role, the challenge is to what degree this patient population can be identified before enrollment into a clinical trial. The data presented in this application defines an ALS patient population responsive to immune regulatory approaches.

The methods disclosed herein methods for treatment of an ALS patient population responsive to immune regulatory approaches, for example, treatment of the slowly progressive ALS patient population with a pharmaceutical composition comprising sodium chlorite.

Disclosed herein are compositions and methods for treatment of a subject suffering from ALS using chlorite. The chlorite ion is $ClO_2^-$. A chlorite (compound) is a compound that contains this group, with chlorine in oxidation state +3. Chlorites are also known as salts of chlorous acid. Chlorine can assume oxidation states of −1, +1, +3, +5, or +7 within the corresponding anions $Cl^-$, $ClO^-$, $ClO_2^-$, $ClO_3^-$ or $ClO_4^-$ known commonly and respectively as chloride, hypochlorite, chlorite, chlorate, and perchlorate. As used herein the term chlorite also includes pharmaceutically acceptable chlorite salts (e.g., $NaClO_2$).

Sodium chlorite, including NP001, a pH-adjusted IV formulation of purified sodium chlorite, has previously been investigated for the treatment of amyotrophic lateral sclerosis (ALS) patients in a randomized phase II clinical trial. While it was found that NP001 was generally safe and well-tolerated, the clinical trial was discontinued following results which indicated there was no significant slowing of disease progression across the entire patient population.

NP001 drug product (DP) is a clear, colorless, sterile solution of sodium chlorite and contains no preservatives. NP001 DP contains purified sodium chlorite (5.61 mg/mL, 62 mM), sodium phosphate, dibasic (0.107 mg/mL) and sterile water for injection, at a pH of 7.5 to 9.5. The active moiety is chlorite, and all clinical doses are expressed as mg/kg chlorite. A concentration of 5.61 mg/mL sodium chlorite (62 mM) translates to 4.2 mg/mL chlorite (62 mM). The formulation is packaged in 30 mL Type 1 flint glass vials with 20 mM stoppers and capped with red aluminum overseals. Each single-use 30 mL vial delivers 20 mL (nominal) of NP001. The formulation is not intended for IV administration neat. Dose preparation instructions specify combining the formulation with 0.45% sodium chloride (half normal saline obtained from commercial vendors) to achieve a total exact volume of 250 mL infusion solution prior to administration.

In the data and examples provided herein, the immune regulator sodium chlorite in ALS patients demonstrates dose dependent modulation of blood cell associated activation markers. Following intravenous administration of a formulation of sodium chlorite (NP001), 24 hours after a single dose, blood monocyte activation markers CD16 and HLA-DR are down regulated in a dose dependent manner. There are no drug related hematologic toxicities or drug related SAEs (adverse events).

The present disclosure provides methods for treating sub-populations of patients suffering from amyotrophic lateral sclerosis (ALS) patients with chlorite, particularly sodium chlorite. While a pharmaceutical composition comprising sodium chlorite may not be effective in all ALS patients, a pharmaceutical composition comprising sodium chlorite is effective in slowing disease progression across at least or greater than a subpopulation of ALS patients, and identifying a responsive subpopulation of ALS patients may lead to a safe and effective treatment of ALS. Accordingly, the present disclosure provides methods for identifying and treating an ALS patient subpopulation using chlorite salts.

Without being bound by any theory, treatment with NP001 (sodium chlorite) may reduce both systemic inflammation and blood monocyte migration into the spinal cord, key processes thought to be critical to the progression of ALS, with the potential to slow the progression of the disease. Sodium chlorite, as an oxidative agent, may function by returning activated macrophages to their inactivated state.

In the target ALS patient subpopulation where disease progression appears to be linked to inflammation and immune system dysregulation, as evidenced by the clinically significant elevation of CPR levels in the target ALS patient subpopulation, NP001 may be effective in slowing or halting disease progression by reducing inflammation and immune system dysregulation by way of oxidation returning activated macrophages to their inactivated state.

Sporadic ALP Pathology and Inherited ALS Pathology

There are multiple types of ALS which may be the cause of disease in a subject, which can be distinguished based upon their signs, symptoms, genetic cause, lack of clear genetic association, or combinations thereof. In comes cases, subjects with ALS may be categorized as sporadic or inherited; a sporadic ALS pathology may occur in a subject with no genetic history (e.g., family history) of ALS; and an inherited ALS pathology may occur in subjects with a genetic history (e.g., family history) of ALS. Among ALS patients, subjects may be further characterized by based upon mutations to one or more genes. For instance, mutations in the C9orf72 gene account for 30 to 40 percent of inherited ALS in the United States and Europe; and worldwide SOD1 gene mutations cause 15 to 20 percent of inherited ALS, and TARDBP and FUS gene mutations each account for about 5 percent of cases of inherited ALS. Other genes associated with inherited ALS also account for a small proportion of cases.

Most cases of ALS are thought to be sporadic, and occur in subjects with no genetic history (e.g., family history) of ALS. As many as 90% to 95% of ALS cases may be sporadic. Mutations to one or more genes may be associated with subjects experiencing either an inherited or sporadic ALS pathology. For instance, 60 percent of individuals with familial ALS may have an identified genetic mutation to one or more genes associated with the condition. In some cases, subjects experiencing either an inherited ALS pathology may have inherited mutations to one or more of the below genes listed in the table below.

In some cases, the C9orf72, SOD1, TARDBP, and FUS genes may be important to the normal functioning of motor neurons and other cells, and mutations to one or more of these genes may contribute to the decline in function or death of motor neurons in ALS patients. In some cases, one or more of the genes listed in Table X below may be important to the normal functioning of motor neurons and other cells, and mutations to one or more of these genes may contribute to the decline in function or death of motor neurons in ALS patients. Without being bound to a particular theory, mutations to one or more of these genes may contribute to a decline in motor neutron function or neuron death as a result of: buildup of protein aggregates in motor neurons, a slowing in the transport of materials needed for the proper function of axons in motor neurons, an accumulation of toxic substances in the motor neurons, or combinations thereof.

TABLE X

Gene Associated with ALS

Figure 4:
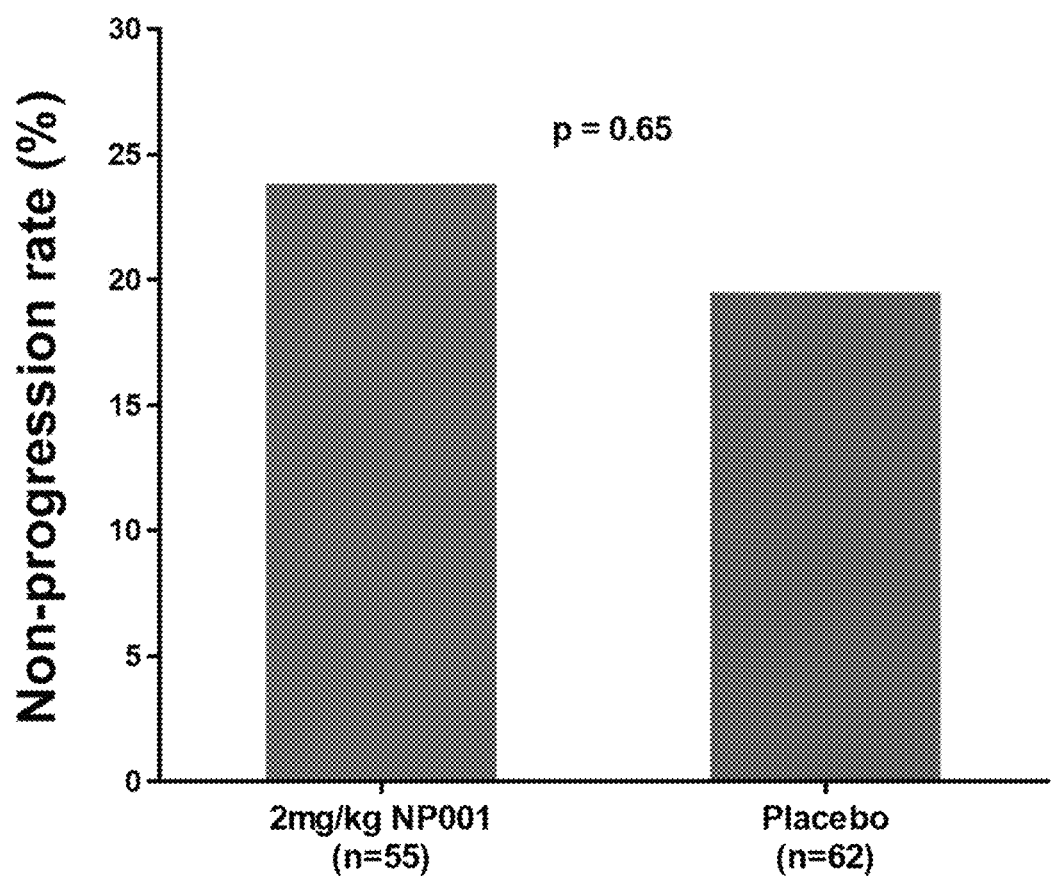
FIG. 4 shows a bar chart of the non-progression rate of subjects treated with a pharmaceutical composition comprising sodium chlorite (NP001) as opposed to a placebo.

| | |
|---|---|
| 1 | SOD1 |
| 2 | ALS2 |
| 3 | Chromosome 18 |
| 4 | SEXT |
| 5 | SPG11 |
| 6 | FUS |
| 7 | Chromosome 20 |
| 8 | VAPB |
| 9 | ANG |
| 10 | TARDBP/TDP-43 |
| 11 | FIG4 |
| 12 | OPTN |
| 13 | ATXN2 |
| 14 | VCP |
| 15 | UBQLN2 |
| 16 | SIGMAR1 |
| 17 | CHMP2B |
| 18 | PFN1 |
| 19 | ERBB4 |
| 20 | HNRNPA1 |
| 21 | MATR3 |
| 22 | TUBA4A |
| 23 | ANXA11 |
| 24 | NEK1 |
| 25 | C9orf72 |
| 26 | CHCHD10 |
| 27 | SQSTM1 |
| 28 | TARDBP |
| 29 | SETX |
| 30 | TAF15 |
| 31 | EWSR1 |
| 32 | hnRNPA2B1 |
| 33 | ELP3 |
| 34 | TBK1 |
| 35 | DCTN1 |
| 36 | NEFH |
| 37 | PRPH |
| 38 | C19ORF12 |
| 39 | SS18L1 |
| 40 | PNPLA6 |
| 41 | PON1-3 |
| 42 | DAO |
| 43 | CHRNA3, 4, B4 |
| 44 | ALS3 |
| 45 | ALS7 |
| 46 | ALS6-21 |
| 47 | ALS-FTD |

In some cases, the methods of treatment disclosed herein differ based upon the characterization of a subject's ALS pathology as sporadic or inherited. In some cases, the methods of treatment disclosed herein differ based upon the characterization of a subject's ALS pathology as inherited based upon to mutations to one or more genes associated with the condition. In some cases, the methods of treatment disclosed herein differ based upon the characterization of a subject's ALS pathology sporadic or inherited, in combination with mutations to one or more genes associated with the condition. In some cases, the methods of treatment disclosed herein differ based upon the characterization of a subject's ALS pathology as inherited, where the subject has an inherited mutation to one or more of an ALS associated gene, such as one or more of the genes listed in Table X.

In some cases, subjects experiencing an inherited ALS pathology may progress more quickly, and may begin to experience a symptom of ALS earlier then subject with experiencing a sporadic ALS pathology. In some cases, subjects experiencing ALS experiencing an inherited ALS pathology may be less likely to respond to treatment with chlorite. In some cases, subjects experiencing ALS experiencing a sporadic ALS pathology may be more likely to respond to treatment with chlorite. In some cases, a subject experiencing ALS experiencing a sporadic ALS pathology may have an inherited mutation to an ALS associated gene, such as one or more of the genes listed in Table X. In some cases, a subject experiencing ALS experiencing a sporadic ALS pathology may lack an inherited mutation to an ALS associated gene, such as one or more of the genes listed in Table X.

In some cases, the methods of treatment disclosed herein comprise determining if the subject has a sporadic or inherited ALS pathology, and treating the subject with chlorite if the subject has a sporadic ALS pathology. In some cases, the methods of treatment disclosed herein comprise determining if the subject has a sporadic or inherited ALS pathology, and not treating the subject with chlorite if the subject has an inherited ALS pathology. In some cases, the methods of treatment disclosed herein comprise determining if the subject has a mutation in one or more ALS associated genes, and treating the subject with chlorite if the subject has a mutation in the one or more ALS associated genes, wherein the one or more ALS associated genes comprise: SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3, 4,B4, ALS3, ALS7, ALS6-21, and ALS-FTD. In some cases, the methods of treatment disclosed herein comprise determining if the subject has a mutation in one or more ALS associated genes, and not treating the subject with chlorite if the subject has a mutation in the one or more ALS associated genes, wherein the one or more ALS associated genes comprise: SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, and ALS-FTD. In some cases, the methods of treatment disclosed herein comprise determining if the subject has a sporadic or inherited ALS pathology and an mutation to one or more ALS associated genes, wherein the one or more ALS associated genes comprise: SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, and ALS-FTD. In some cases, the inherited mutation is inherited in an autosomal dominant pattern. IN some cases, the mutation in the one or more ALS associated genes is an inherited mutation. In some cases, the inherited mutation is inherited in an autosomal recessive pattern. In some cases, the inherited mutation is inherited in a X-linked dominant pattern.

ALS Patient Subpopulations Parameters

Disclosed herein are multiple methods of identifying ALS patient subpopulations likely to be responsive to treatment with a pharmaceutical composition comprising sodium chlorite. Characteristics of responsive patient subpopulations vary and may include patient age, patient C-reactive protein (CRP) levels, duration since ALS symptom onset, and combinations thereof. In some cases, the responsive patient subpopulation can be further defined by elevated levels other inflammatory biomarkers.

In an exemplary embodiment, an ALS patient subpopulation responsive to treatment with a pharmaceutical composition comprising sodium chlorite includes patients age includes patients with stable disease having elevated C-reactive protein (CRP) levels of at least or greater than 1.13 mg/L, age 40-65. In some cases, the ALS patient subpopulation has a duration following ALS symptom onset of at least 12 months. In some cases, the ALS patient subpopulation has a duration following ALS symptom onset of at least 18, 21, or 24 months.

In an exemplary embodiment, an ALS patient subpopulation responsive to treatment with a pharmaceutical composition comprising sodium chlorite includes patients with stable disease having elevated C-reactive protein (CRP) levels of greater than 3 mg/L. In some cases, the ALS patient subpopulation is age 40-65. In some cases, the ALS patient subpopulation also has a duration following ALS symptom onset of at least 12 months. In some cases, the ALS patient subpopulation has a duration following ALS symptom onset of at least 18, 21, or 24 months.

In an exemplary embodiment, an ALS patient subpopulation responsive to treatment with a pharmaceutical composition comprising sodium chlorite includes patients age 45-60. In some cases, the ALS patient subpopulation has elevated C-reactive protein (CRP) levels of greater than 1.13 mg/L. In some cases, the ALS patient subpopulation has elevated C-reactive protein (CRP) levels of greater than 3 mg/L In some cases, the ALS patient subpopulation has a duration following ALS symptom onset of at least 12 months. In some cases, the ALS patient subpopulation has a duration following ALS symptom onset of at least 18, 21, or 24 months.

In an exemplary embodiment, an ALS patient subpopulation responsive to treatment with a pharmaceutical composition comprising sodium chlorite includes patients having a duration ALS symptom onset of at least 12 months. In some cases, the ALS patient subpopulation has a duration following ALS symptom onset of at least 18, 21, or 24 months. In some cases, the ALS patient subpopulation has elevated C-reactive protein (CRP) levels of greater than 1.13 mg/L. In some cases, the ALS patient subpopulation has elevated C-reactive protein (CRP) levels of greater than 1.13 mg/L. In some cases, the ALS patient subpopulation is age 40-65.

In some cases, an ALS patient subpopulation responsive to treatment with a pharmaceutical composition comprising sodium chlorite may also include patients having elevated levels of other inflammatory biomarkers. These inflammatory markers may include, but are not limited to tumor necrosis factors (e.g., TNF-alpha), monocyte chemoattractant proteins (e.g., MCP-1), interleukins (e.g., IL-6, IL-12) and chemokine ligands (e.g., CXCL1). These inflammatory proteins may be produced by an array of lymphocytes that include T cells, monocytes, and macrophages. In some cases, an ALS patient subpopulation responsive to treatment with a pharmaceutical composition comprising sodium chlorite has elevated levels of: circulating (e.g., plasma) proinflammatory, anti-inflammatory, regulatory cytokines, IL-4, IL-6, IL-10, soluble IL-2 receptor, soluble IL-6 receptor, tumor necrosis factor (TNF)-$\alpha$, soluble TNF receptor-1, and/or IL-1 receptor antagonist. In some cases, an ALS patient subpopulation responsive to treatment with a pharmaceutical composition comprising sodium chlorite has an elevated biomarker of inflammation, IL-18, and are positive for LPS at baseline. In some cases, an ALS patient subpopulation responsive to treatment with a pharmaceutical composition comprising sodium chlorite has elevated levels of one or more of the above listed inflammatory biomarkers which are twice as high as baseline when compared to the population of ALS patients that do not respond to treatment with a pharmaceutical composition comprising sodium chlorite. In some cases, these plasma markers include IL18, gamma interferon, IL6 and CRP.

In some cases, is plausible that the disease mechanism and trajectory for early age at onset (less 40 years) differs from older patients and is more likely to have a genetic or heritable component as is often seen in other chronic conditions such as cancer and cardiovascular disease. With regard to the exclusion of the older age groups, it appears that CRP levels increase with age and that the CRP sensitivity cutoffs applied to the a pharmaceutical composition comprising sodium chlorite phase 2 trials may have allowed an over representation of older ALS patients for whom the CRP values measured other disease activities, unrelated to ALS, thus obscuring the ALS specific activities of a pharmaceutical composition comprising sodium chlorite.

Measurement of ALS Symptoms, Disease Progression, and Treatment Efficacy

Disclosed herein are methods of identifying ALS symptoms and ALS symptom onset, methods of monitoring and assessing ALS disease progression, and methods of evaluation treatment efficacy based upon ALS symptoms and ALS disease progression.

I. ALS Symptoms & Identification of Onset

Amyotrophic lateral sclerosis (ALS) is a progressive neurodegenerative disease that destroys motor neurons in the brain and spinal cord, eventually leading to muscle paralysis, and death, usually within 2-4 years of diagnosis. Symptoms of ALS generally result from the gradual destruction of motor neurons, and may include: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, muscle cell death, or a combination of two or more thereof. Eventually, ALS patients will lose the ability to move their limbs, walk, hold their head up, and even breath. Thus, ALS patients will eventually become wheelchair bound, will require assistance performing all basic daily functions such as dressing, ambulating, eating, and using the bathroom, and will eventually require a tracheotomy and a ventilator.

Because the symptoms of ALS are so varied and may appear to be little more than symptoms of fatigue in its early stages, it is difficult to diagnose early. It is also difficult to diagnose because the symptoms often mimic those of other neurological diseases. For this reason, diagnosis is often accomplished by ruling out other neurological diseases as symptoms progress. Diagnosis generally begins with an identification of the problem as a neurological issue and a neurological exam, followed by diagnostic tests to rule out other neurological conditions, and confirm the presence of ALS. Such diagnostic tests may include EMG (electromyography) to test nerve conduction, MRI (magnetic resonance imaging) to image the spinal cord and surrounding nerves, muscle biopsy, and blood and urine tests seeking evidence of other diseases whose symptoms are similar to early signs of ALS such as thyroid and parathyroid disease, vitamin B12 deficiency, HIV, hepatitis, auto-immune diseases, and some types of cancer. Creatine kinase (CK), a muscle enzyme released when muscles are injured or die, is also measured, as an increased level of CK is indicative of muscle death, a symptom of ALS. In some cases, a spinal fluid tap may also be used to test for abnormal cells in spinal fluid.

Following diagnosis of ALS, identification of patients with symptom onset exceeding, e.g., 12, 18, or 24 months, for purposes of determining whether they are part of the target ALS patient population may include reviewing the subject's medical history for symptoms of ALS, reviewing the subject's medical history for a diagnosis of ALS, or inquiring from the subject as to when they first began to experience symptoms of ALS. Inquiring with the subject directly as to when they first believe they began to experience symptoms may useful, as many patients may be able to identify symptoms of ALS they recall experiencing which may not be reflected in their medical history, at a date which precedes the first reported symptoms in their medical history, or preceding their formal ALS diagnosis. For example, a patient may report having experienced one or more of the above identified symptoms of ALS at a date which would qualify them as part of the target ALS patient population, for example, at least or greater than 12 months following symptom onset, at least or greater than 18 months following symptom onset, or at least or greater than 21 months following symptom onset.

II. Evaluation of Patients Using ALSFRS-R Score

ALS disease progression is generally monitored by using the ALSFRS-R (ALS Functional Rating Scale-Revised) Score. The ALSFRS-R is a questionnaire-based scale that measures and tracks changes in a patient's physical function over time. The ALSFRS-R Score is widely used in clinical trials and patient treatment to monitor disease progression.

The ALSFRS-R Score measures 12 aspects of physical function including: speech salivation, swallowing, handwriting, cutting food, climbing stairs, turning in bed, walking, dressing and hygiene, dyspnea (difficulty breathing), orthopnea (shortness of breath while lying down), and breathing insufficiency. Each function is scored from 4 (normal) to 0 (no ability), and them the sum of each value is taken to produce a score, with a maximum score of 48, and a minimum score of 0. The higher the score, the greater the physical functionality of the patient, and the less ALS has progressed within the patient.

ALSFRS-R Score can be measured in patients upon questionnaire, or physical examination and observation of the tasks being performed by a healthcare professional. For example, as to speech, a score of 4 may be reflective of normal speech, a score of 3 may be reflective of an audible disturbance in speech, a score of 2 may be reflective of intelligible speech with repeating, a score of 1 may be reflective of some speech with non-verbal communications, and a score of 0 may be reflective of a loss of useful speech. In evaluating swallowing, a score of 4 may be reflective of normal swallowing, a score of 3 may be reflective of occasional choking, a score of 2 may be reflective of dietary changes, a score of 1 may indicate the need for a feeding tube, and a score of 0 may be reflective of exclusively parenteral or enteral feeding. Methods of determining the ALSFRS-R Score are well known within the art, and any suitable method for assessing ALSFRS-R Score may be utilized to evaluate subjects.

Evaluation of patient ALSFRS-R Scores may be utilized in assessing disease progression upon treatment with a pharmaceutical composition comprising sodium chlorite, and be used to classify a patient as a responder or a non-responder based on disease progression. A 0-point to 1-point reduction in ALSFRS-R Score upon treatment with a pharmaceutical composition comprising sodium chlorite over a period of approximately 6 months may indicate ALS disease progression has slowed or halted, and would qualify as patient as a responder.

III. Quantification of Patient CRP Levels

Elevated CRP levels are commonly used as a marker of underlying inflammation.

| Level (hs-CRP) | Classification | Illustrative Clinical Examples |
| --- | --- | --- |
| <0.3 mg/L | Normal | Level most seen in healthy adults |
| 0.3-1.0 mg/L | Normal or minor elevation | Can be seen in obesity, pregnancy, depression, diabetes, common cold, gingivitis, periodontitis, sedentary lifestyle, cigarette smoking, and genetic polymorphisms |
| 1.0-10.0 mg/L | Moderate elevation | Systemic inflammation such as RA, SLE or other autoimmune diseases, malignancies, myocardial infarction, pancreatitis, bronchitis |
| >10 mg/L | Marked elevation | Acute bacterial infections, viral infections, systemic vasculitis, major trauma |

Patient CRP levels are a metric utilized in evaluating an ALS patient as a member of the target ALS patient population. As a neurodegenerative disease which is thought to progress in the target patient population based, in part, upon inflammation and immune system dysregulation, patient; CPR levels are used to identify patients experiencing inflammation and immune system dysregulation, and likely to be responsive to treatment with a pharmaceutical composition comprising sodium chlorite. Patient CPR levels are determined by analysis of CPR plasma content, with CPR levels of greater than 3 mg/L representing clinically significant elevated levels of CRP. Patients with CRP levels of at greater than 3 mg/L may be members of the target ALS patient population likely to be responsive to treatment with a pharmaceutical composition comprising sodium chlorite.

Various methods of screening patient CRP plasma content may be utilized in present embodiments to determine if a patient is a member of the target ALS patient population. Patient CRP plasma content is generally determined using blood tests. Non-limiting methods of screening patient CRP levels may include latex agglutination, latex-enhanced nephelometry, photometric measurement of antigen-antibody reaction, or highly sensitive Near Infrared Particle Immunoassay rate methodology. However, any other suitable method for quantitatively determining patient CRP levels of at least or greater than 3 mg/L may be utilized in present embodiments to determine if a patient is a member of the target ALS patient population.

IV. Quantification of Vital Capacity

Vital capacity is the greatest volume of air that can be expelled from the lungs after taking the deepest possible breath. As ALS progresses, patients lose the ability to breath without assistance as the motor neurons controlling the diagraph succumb to the disease, eventually resulting in tracheotomy and institution of a ventilator to prolong patient life. Reduction in vital capacity can be used to measure ALS disease progression, including percent change from baseline vital capacity. Vital capacity is about 4800 mL, and varies by age and body size. It can be calculated by summing tidal volume, inspiratory reserve volume, and expiratory reserve volume. VC=TV+IRV+ERV. Vital capacity for a given patient can be measured using a spirometer, or other device known within the art, and measuring vital capacity may be convenient for assessing ALS disease progression for a given patient. Other non-limiting methods of measuring vital capacity include spirometry, or a forced expiratory volume test, however, any other suitable method for quantitatively determining change in patient vital capacity may be utilized to assess ALS disease progression and treatment efficacy according to the embodiments disclosed herein.

In ALS patients, loss of respiratory vital capacity translates directly to survival outcome. Similar to the variability seen in ALSFRS-R score comparisons, respiratory function changes in ALS patients are reproducible over time, whether the measures are FVC or SVC. ALS patient natural history studies of VC over time in ALS patients confirm an average loss of 2.5-3% of function per month.

Preparation of Chlorite Compounds for Patient Treatment

Described herein are exemplary methods of preparing and purifying chlorite for use in pharmaceutical formulations, including, for example, a pharmaceutical composition comprising sodium chlorite. Disclosed are methods of chlorite preparation, methods of preparing chlorite compounds with the necessary purity and pH for use in pharmaceutical formulations, and pharmaceutical formulations comprising chlorite, for example, a pharmaceutical composition comprising sodium chlorite.

I. Methods of Preparation

Described herein are methods of purifying chlorite. It is intended that the methods described herein can be used to produce the formulations or pharmaceutical formulations described herein. However, the formulations and pharmaceutical formulations described herein may also be produced by other methods, and the formulations and pharmaceutical formulations described herein are not limited to those produced by the methods described herein.

In some variations, the purification is by subjecting a mixture comprising chlorite to conditions in which chlorite is in solution, but one or more impurities are insoluble. The chlorite is separated from the insoluble impurities. In some variations, the chlorite is further purified by crystallization of the chlorite from the mixture, and separation of the chlorite from the remaining mixture. In some variations, the chlorite is purified from a mixture comprising sodium chlorite.

Generally, the chlorite ions may be from any source containing chlorite. For example, chlorite may be a chlorite salt, for example alkali metal salts, sodium chlorite, potassium chlorite, and the like, or a mixture of chlorite salts. Alternatively, the source of chlorite may be from a formulation comprising chlorite. In some variations, chlorite is purified from a formulation comprising a pharmaceutical composition comprising sodium chlorite, TCDO or WF10. In another variation, chlorite is from a solution comprising sodium chlorite.

In some variations, impure chlorite, including but not limited to impure sodium chlorite, is dissolved in a solvent or a solvent system. In some variations, any solvent in which chlorite dissolves is used. In another variation, any solvent in which chlorite dissolves and with which chlorite does not react is used. In some variations, the solvent is distilled water. In some variations, the solvent is a non-organic solvent.

In some variations impure sodium chlorite is between about 0.1% to about 99% per weight of the starting material. As non-limiting examples of the purity of the chlorite starting material, the chlorite is between about any of 0.1% and about 5%; between about 1% and about 5%; between about 4% and about 10%; between about 1% and about 15%; between about 15% and about 25%; between about 5% and about 25%; between about 25% and about 50%; between about 50% and about 75%; between about 75% and about 85%; between about 85% to about 95%; between about 60% and about 90%; between about 95% and about 99% per weight of the starting material; at least or greater than about 50, at least or greater than about 60, at least or greater than about 70, at least or greater than about 80, at least or greater than about 90, or at least or greater than about 95% pure. If the impure chlorite is in a solvent, the percent purity is relative to the non-solvent components. In some variations the chlorite is between about 75% and about 85% pure. In some variations the chlorite is between about 85% and about 95% pure. In some variations the chlorite is at least or greater than about 85% pure.

In some variations, small amounts of hydrogen peroxide are added to the dissolved chlorite. While not wishing to be bound by theory, the addition of small amounts of hydrogen peroxide may reduce sodium chlorate to sodium chlorite. If desired, unreacted hydrogen peroxide may be subsequently removed. In some variations, hydrogen peroxide is added after the initial dissolution of chlorite step and subsequently removed by filtration, for example, by centrifugal filtration.

Briefly, one method of preparing a formulation comprising chlorite as disclosed herein can be achieve through the steps of: (a) concentrating a chlorite solution at a temperature between 60° C. to about 100° C., whereby impurities precipitate from the solution, (b) removing the impurities from the concentrated solution by filtration, (c) inducing crystallization of chlorite from the concentrated solution, (d) harvesting the resulting chlorite solids by filtration, and (e) dissolving the chlorite solids in an aqueous solvent. It is envisioned that in some variations the resulting aqueous formulation of chlorite comprises a purity of at least or greater than 80% chlorite, at least or greater than 85% chlorite, at least or greater than 90% chlorite, at least or greater than 95% chlorite or at least or greater than 99% chlorite. However, embodiments of the present disclosure are not limited thereto, and any suitable method of preparing chlorite or a pharmaceutically acceptable salt thereof can be utilized.

II. Chlorite Purity and pH

Described in present disclosure are compositions and methods using chlorite formulated in aqueous solution in which the chlorite is greater than 95% pure. In some cases, the chlorite can be greater than 97%, 99%, 99.5% or 99.9% pure. In some cases, the chlorite can be at least or greater than 95%, 97%, 99%, 99.5% or 99.9% pure. As used herein, the "purity" of chlorite in a sample is calculated as the percent weight of chlorite salt to the total weight of the sample. In determining the purity of chlorite in a solution, the weight of the solvent (e.g., water in an aqueous solution) is not included. Purity may be evaluated using ion chromatography and an ion detector, by calibrated integration of the respective peaks; for example, chlorite, chloride, chlorate, phosphate and sulfate in the compound or formulation. For example, chlorite is commercially available as sodium chlorite, technical grade, at a purity of 80% (catalog No. 244155 Sigma-Aldrich).

Alternatively, crystalline sodium chlorite is provided in a purity greater than 95%, greater than 96%, greater than 97%, greater than 98%, greater than 99%, greater than 99.5% or greater than 99.9%. Solid pharmaceutical formulations comprising crystalline sodium chlorite in a purity greater than 95%, greater than 96%, greater than 97%, greater than 98%, greater than 99%, greater than 99.5% or greater than 99.9% in addition to one or more pharmaceutical excipients are also encompassed.

The chlorite formulations for use with the present disclosure can comprise low amounts of chlorate, sulfate or chloride. As used herein, a formulation is "substantially free" of a molecule if the molecule comprises no more than 1 part in 1000 per weight of non-solvent molecules in the formulation. In certain embodiments, the weight ratio of chlorite to chlorate is greater than 100:1.5, greater than 100:0.5, greater than 100:1, or greater than 100:0.1. In one embodiment, the composition is substantially free of chlorate. In another embodiment, the weight ratio of chlorite to chloride is greater than 100:45.5 or greater than 100:8.5. In one embodiment the composition is substantially free of chloride. In a further embodiment, the weight ratio of chlorite to sulfate is greater than 100:16.4 or greater than 100:1.6. In one embodiment the composition is substantially free of sulfate.

The pH of a chlorite formulation for use with the present disclosure can be adjusted to between about 7 and about 11.5. In some embodiments, the pH of a chlorite formulation is lowered to between about 7 and about 11.5 using a pH adjusting compound that does not expose the formulation to high local acidity. In some embodiments, the pH adjusting compound is any one or more of monosodium phosphate, disodium phosphate, or acetic acid.

Also described herein are methods of preparing chlorite formulations and pharmaceutical formulations, including but not limited to the chlorite formulations specifically described herein. Also described herein are kits and methods of administration of the formulations and pharmaceutical formulations described herein. Various exemplary aspects and variations of the disclosure are described in the "Summary," as well as elsewhere herein, including but not limited to the Examples. It is also understood that the disclosure includes embodiments comprising, consisting essentially of, and/or consisting of one or more elements as described herein.

In some embodiments, the disclosure makes use of aqueous formulations comprising chlorite. In some embodiments, the chlorite formulation comprises an aqueous solvent, and optionally one or more other solvents for chlorite. In some embodiments, the formulations comprise chlorite and an aqueous solvent for chlorite, and have a pH of about 7 to about 11.5.

Solvents or combinations of solvents for use in the formulations described herein can be determined by a variety of methods known in the art. One non-limiting example includes (1) theoretically estimating solvent solubility parameter value(s) and choosing the one(s) that match with chlorite, using standard equations in the field; and (2) experimentally determining the saturation solubility of chlorite in the solvent(s), and (3) choosing one or more that exhibits the desired solubility, and (4) selecting a solvent or solvents that do not diminish the activity of chlorite, or that do not or only minimally react with chlorite. In some embodiments, the liquid formulations described herein comprise a plurality of solvents.

In some embodiments, the chlorite formulations comprise an aqueous solvent. In some variations, water is the principal solvent in the aqueous formulations. In some variations, water is at least or greater than about 50% by volume of the solvent component of an aqueous formulation. In some variations, water is at least or greater than about 50% by volume of the aqueous formulation. In some variations, water is any of between about 50 to about 60, between about 60 to about 70, between about 70 to about 80, between about 80 to about 90, between about 90 to about 99, at least or greater than about 50, at least or greater than about 60, at least or greater than about 70, at least or greater than about 80, at least or greater than about 90, or at least or greater than about 95, about 50, about 60, about 70, about 80, about 90, or about 95 percent by volume of the solvent component. In some variations, water is any of between about 50 to about 60, between about 60 to about 70, between about 70 to about 80, between about 80 to about 90, between about 90 to about 99, at least or greater than about 50, at least or greater than about 60, at least or greater than about 70, at least or greater than about 80, at least or greater than about 90, or at least or greater than about 95, percent by volume of the aqueous formulation. In some variations, water is at least or greater than about 95% by volume of the aqueous formulation. In some variations, water is between about 80 to about 90% by volume of the aqueous formulation. In some variations, water is between about 90 to about 99% by volume of the aqueous formulation.

The formulations may have differing concentration of chlorite. In some embodiments, the concentration of chlorite in the formulation is high, and then is diluted to a less concentrated form prior to administration. In some embodiments, a formulation described herein is diluted about, at least or greater than about or less than about 2.5×, about 5×, about 7.5×, about 10×, about 20×, about 25×, about 50×, about 100×, about 200×, about 250×, about 300×, about 500×, or about 1000×. In some embodiments, a formulation described herein is diluted between about 2× and about 10×, between about 10× and about 50×, between about 50× and about 100×, between about 100× and about 500×, or between about 500× and about 1000×. In some embodiments, a formulation as described herein is diluted between about 2× and about 10×. In some embodiments, a formulation as described herein is diluted between about 10× and about 50×. In some embodiments, a formulation as described herein is diluted about 7.5×. In some embodiments, a formulation as described herein is diluted about 25×. In some embodiments, a formulation as described herein is diluted about 200×.

In some embodiments, the concentration of chlorite in the formulations described herein is between about 1 µM and about 1.5 M. In another embodiments, the concentration of chlorite in the formulations described herein is between any of about 1 M and about 1.5 M; between about 1 µM and about 100 mM; between about between about 10 µM and about 100 mM; between about 0.1 mM and about 10 mM; between about 0.1 mM and about 500 mM; between about 0.1 mM and about 200 mM; between about 1 mM and about 100 mM; between about 0.1 mM and about 5 mM; between about 50 mM and about 100 mM; between about 55 mM and about 70 mM; between about 60 mM and about 65 mM; between about 100 mM and about 500 mM; between about 200 mM and about 400 mM; between about 300 mM and about 700 mM; about 1 mM; about 1.5 mM; about 2 mM; about 2.5 mM; about 3 mM; about 3.5 mM; about 4 mM; about 5 mM; about 10 mM; about 20 mM; about 30 mM; about 40 mM; about 50 mM; about 60 mM; about 62 mM; about 65 mM; about 70 mM; about 80 mM; about 90 mM; about 100 mM; at least or greater than about 0.1 mM; at least or greater than about 1 mM; at least or greater than about 2 mM; at least or greater than about 5 mM; at least or greater than about 10 mM; at least or greater than about 20 mM; at least or greater than about 30 mM; at least or greater than about 40 mM; at least or greater than about 50 mM; at least or greater than about 60 mM; at least or greater than about 70 mM; at least or greater than about 80 mM; at least or greater than about 90 mM; or at least or greater than about 100 mM. In preferred embodiments, the concentration of chlorite in the formulations described herein is about or at least or greater than about 60 mM.

In some embodiments, the concentration of chlorate in the formulations described herein is between about 50 mM and about 100 mM. In some embodiments, the concentration of chlorate in the formulations described herein is between about 55 mM and about 75 mM. In some embodiments, the concentration of chlorate in the formulations described herein is between about 0.1 mM and about 10 mM. In some embodiments, the concentration of chlorate in the formulations described herein is between about 1 mM and about 5 mM.

In some embodiments, the chlorite formulation has a pH no greater than about 12.0. In some embodiments, the pH of the formulation is any of no greater than about 11.5, about 11.0, about 10.5, about 10.0, about 9.5, about 9.0, about 8.5, about 8.0, about 7.5, about 7.0, about 6.5, or about 6.0. In some embodiments, the pH of the formulation is no greater than about 11.5. In some embodiments, the pH of the formulation is no greater than about 10.5. In some embodiments, the pH of the formulation is no greater than about 8.5. In some embodiments, the pH of the formulation is no greater than about 7.5. In some embodiments, the pH of the formulation is between any one or more of about 7 and about 12; between about 7 and about 11.5; between about 7 and about 10.5; between about 7 and about 10; between about 7 and about 9.5; between about 7 and about 9.0; between about 7 and about 8.5; between about 7 and about 8.0; between about 7 and about 7.5; between about 7.5 and about 8; between about 7.5 and about 8.5; between about 7 and about 8; between about 8 and about 9; between about 7.0 and about 8.5; between about 8 and about 8.5; between about 8.5 and about 9; between about 7.1 and about 7.7; between about 7.2 and about 7.6; between about 7.3 and about 7.4; about 7.0; about 7.1; about 7.2; about 7.3; about 7.4; about 7.5; about 7.6; about 7.7; about 7.8; about 7.9; about 8.0; about 8.1; about 8.2; about 8.3; about 8.4; about 8.5; about 8.6; about 8.7; about 8.8; or about 8.9. In some embodiments, the chlorite formulation has a pH of about 7.0 to about 9.0. In some embodiments, the chlorite formulation has a pH of about 7.0 to about 8.5. In some embodiments, the chlorite formulation has a pH of about 6.0 to about 8.5. In some embodiments, the chlorite formulation has a pH of about 7.0 to about 8.0. In some embodiments, the chlorite formulation has a pH of about 7.4. The chlorite formulation can have a pH that is at a physiological level.

In some embodiments, the chlorite formulations have a pH as described above, and are formulated for any one or more of parenteral, systemic, or intravenous administration. In some embodiments, the chlorite formulations have a pH as described above, and have a percentage chlorite purity as described herein.

In some embodiments, the formulations described herein have a pH as described above, and have a concentration of chlorite as described herein. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 1 and about 100 mM. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 1 and about 5 mM. In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, and have a concentration of chlorite between about 50 and about 80 mM.

In some embodiments, the aqueous formulations described herein have a pH between about 7 and about 11.5, or between about 7.0 and about 10, or between about 7.0 and about 9.0, or between about 7.0 and about 8.5, or between about 7.1 and about 7.7, wherein the pH was adjusted with a pH adjusting agent that is any one or more of a phosphate, or acetic acid.

In some embodiments, the formulations described herein are stable with respect to one or more of pH or chlorite degradation over a period of any of at least or greater than about 1 day, at least or greater than about 2 days, at least or greater than about 3 days, at least or greater than about 4 days, at least or greater than about 5 days, at least or greater than about 6 days, at least or greater than about 1 week, at least or greater than about 2 weeks, at least or greater than about 3 weeks, at least or greater than about 4 weeks, at least or greater than about 5 weeks, at least or greater than about 6 weeks, at least or greater than about 7 weeks, at least or greater than about 8 weeks, at least or greater than about 1 month, at least or greater than about 2 months, at least or greater than about 3 months, at least or greater than about 4 months, at least or greater than about 5 months, or at least or greater than about 6 months. In some embodiments, the formulations described herein are stable with respect to one or more of pH or chlorite degradation over a period of any of at least or greater than about 1 week. In some embodiments, the formulations are stable with respect to one or more of pH or chlorite degradation over a period of any of at least or greater than about 1 month. In some embodiments, the formulations described herein are stable with respect to one or more of pH or chlorite degradation at one or more of room temperature, refrigerated conditions, or approximately 4 degree C. In some embodiments, the formulations described herein are stable with respect to one or more of pH or chlorite degradation under conditions of diminished light or storage in a container that limits the amount of light to which the formulation is subjected. In some embodiments, the formulations described herein are stable with respect to one or more of pH or chlorite degradation when stored in the dark. Examples of stable pH, as used herein, means that the pH of the formulation changes by less than any of about 0.1, about 0.2, about 0.3, about 0.4, about 0.5, about 0.6, about 0.7, about 0.8, about 0.9, or about 1 relative to the pH of the formulation as initially prepared. In some embodiments, the pH of the formulation changes by less than about 0.2 relative to the pH of the formulation as initially prepared. The pH may be measured using, for example, a pH meter. Examples of stable chlorite formulations include those in which less than any of about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% of the chlorite degrades into a non-chlorite ion relative to the amount of chlorite present in the formulation as initially prepared. In some embodiments, less than about 2% of the chlorite degrades into a non-chlorite compound relative to the amount of chlorite present in the formulation as initially prepared. In some embodiments, less than about 0.5% of the chlorite degrades into a non-chlorite compound relative to the amount of chlorite present in the formulation as initially prepared. The presence of non-chlorite elements may be measured, for example, using gas chromatography (GC), mass spectrometry, or other methods known by those of skill in the art.

In some embodiments, the chlorite formulations described herein comprise no greater than about 5% by weight of deleterious non-chlorite elements of other commercially available formulations. In some embodiments, the chlorite formulations described herein comprise any of no greater than about 4%, about 3%, about 2%, about 1%, about 0.5%, about 0.3%, about 0.25%, about 0.2%, about 0.1%, about 0.05%, or about 0.02%, by weight of deleterious non-chlorite elements of other commercially available formulations. In some embodiments, the chlorite formulations described herein comprise any of no greater than about 4% by weight of deleterious non-chlorite elements of other commercially available formulations. In some embodiments, the chlorite formulations described herein comprise any of no greater than about 2% by weight of deleterious non-chlorite elements of other commercially available formulations. In some embodiments, the chlorite formulations described herein comprise any of no greater than about 0.5% by weight of deleterious non-chlorite elements of other commercially available formulations. In some embodiments, the chlorite formulations described herein comprise any of no greater than about 0.05% by weight of deleterious non-chlorite elements of other commercially available formulations. In some embodiments, the chlorite formulations described herein are substantially free of the deleterious non-chlorite elements of other commercially available formulations. Non-limiting examples of methods of detection of non-chlorite components include HPLC; SPCS, for example using a Novosep A2 column with 3.6 mM Sodium Carbonate as a mobile phase, 5µ, 250×4.0 mm, flow rate 0.8 mL/min; DS-Plus Suppressor, for example using a Novosep A2 column with 3.6 mM Sodium Carbonate as a mobile phase, 5µ, 250×4.0 mm, flow rate 0 8 mL/min; an Allsep A-2 Anion column using 2.1 mM NaHCO$_3$/1.6 mM Na$_2$CO$_3$ as a mobile phase, 100×4.6 mm, flow rate 2.0 mL/min; an anion HC column using 2.8 mM NaHCO$_3$: 2.2 mM Na$_2$CO$_3$ in 10% Methanol as a mobile phase, 150×4.6 mm, flow rate 1.4 mL/min; or an Allsep A-2 Anion column using 2.1 mM NaHCO$_3$/1.6 mM Na$_2$CO$_3$ as a mobile phase, 5µ, 100×4.6 mm, flow rate 1.0 mL/min. See, for example, the Alltech Associates, Inc. Grace Davison line of products and product information for details.

In some embodiments, the chlorite formulations described herein contain less than about 1.9% of chloride ions. In some embodiments, the chlorite formulation contains any of less than about 1.9%, less than about 1.8%; less than about 1.5%; less than about 1.0%; less than about 0.5%; less than about 0.3%; less than about 0.1%; less than about 0.05%; less than about 0.01%; less than about 0.001%; between about 0.001 to about 0.1%; between about 0.1 to about 0.5%; between about 0.5 to about 1.0%; between about 1.0 to about 1.5%; or between about 1.5 to about 1.8% by weight of chloride ions. In some embodiments, the chlorite formulation contains less than about 0.5% by weight of chloride ions. In some embodiments, the chlorite formulation contains less than about 0.24% by weight of chloride ions. In some embodiments, the chlorite formulation contains less than about 0.2% by weight of chloride ions. In some embodiments, the chlorite formulation contains less than about 0.1% by weight of chloride ions. In some embodiments, the chlorite formulation is substantially free of chloride ions. In some embodiments, the level of chloride ions is below the level of detection using HPLC.

In some embodiments, the chlorite formulation contains less than about 1.5% of chlorate ions. In some embodiments, the chlorite formulation contains any of less than about 1.4%, less than about 1.3%; less than about 1.0%; less than about 0.5%; less than about 0.3%; less than about 0.1%; less than about 0.01%; less than about 0.001%; between about 0.001 to about 0.1%; between about 0.001 to about 0.01%; between about 0.01 to about 0.1%; between about 0.1 to about 0.5%; between about 0.5 to about 1.0%; or between about 1.0 to about 1.4% of chlorate ions. In some embodiments, the chlorite formulation is substantially free of chlorate ions. In some embodiments, the chlorite formulation contains less than about 0.5% by weight of chlorate ions. In some variations, the chlorite formulation is substantially free of chlorate ions. In some embodiments, the chlorite formulation contains less than about 0.19% by weight of chlorate ions. In some embodiments, the chlorite formulation contains less than about 0.1% by weight of chlorate ions. In some embodiments, the level of chlorate ions is below the level of detection using HPLC.

In some embodiments, the chlorite formulation contains less than about 0.7% of sulfate ions. In some embodiments, the chlorite formulation contains any of less than about 0.65%; less than about 0.6%; less than about 0.5%; less than about 0.4%; less than about 0.3%; less than about 0.2%; less than about 0.1%; less than about 0.08%; less than about 0.07%; less than about 0.06%; less than about 0.05%; less than about 0.005%; less than about 0.0005%; between about 0.001 to about 0.1%; between about 0.01 to about 0.1%; between about 0.01 to about 0.5%; between about 0.06 to about 0.08%; or between about 0.5 to about 0.65% of sulfate ions. In some embodiments, the chlorite formulation contains between about 0.5 to about 0.65% of sulfate ions. In some embodiments, the chlorite formulation is substantially free of sulfate ions. In some embodiments, the chlorite formulation contains less than about 0.5% by weight of sulfate ions. In some embodiments, the chlorite formulation is substantially free of sulfate ions. In some embodiments, the chlorite formulation contains less than about 0.08% by weight of sulfate ions. In some embodiments, the level of sulfate ions is below the level of detection using HPLC.

In some embodiments, the chlorite formulations described herein comprise phosphate ions. In some embodiments, the chlorite formulations described herein comprise sodium ions. In some embodiments, a chlorite formulation comprises chlorite, an aqueous solvent, sodium, and phosphate ions. In some variations, the aqueous solvent consists essentially of water. In some embodiments, a chlorite formulation consists essentially of chlorite, water, sodium, and phosphate, and is substantially free of chlorate. In some embodiments, a chlorite formulation consists essentially of chlorite, water, sodium, and phosphate, and is substantially free of chlorate, and further comprises a pharmaceutically acceptable diluent. In some embodiments, sodium and phosphate are provided in whole or in part as monosodium phosphate or disodium phosphate. In some embodiments, the pharmaceutically acceptable diluent is a saline solution.

In some embodiments, the chlorite formulations described herein comprise no greater than about 10% by weight of by products or impurities present in commercially available technical grade chlorite. Non-limiting examples of by-products or impurities present in commercially available technical grade chlorite include chlorate, sulfate, chlorine dioxide, chloride, sodium bicarbonate, and sodium carbonate. In some embodiments, the chlorite formulations described herein comprise no greater than about any of 15%, about 12%, about 10%, about 9%, about 8%, about 7%, about 6%, about 5%, about 4%, about 3%, about 2%, about 1%, about 0.5%, about 0.3%, about 0.1%, between about 0.1 to about 5%; between about 5 to about 10%; or between about 10 to about 15% by weight of one or more degradation products or impurities present in commercially available technical grade chlorite, including but not limited to one or more of chlorate or sulfate. In some embodiments, the chlorite formulations described herein comprise no greater than about 0.5% by weight of degradation products or impurities present in commercially available technical grade chlorite, including but not limited to one or more of chlorate or sulfate. In some embodiments, the chlorite formulations described herein comprise no greater than about 5% by weight of degradation products or impurities present in commercially available technical grade chlorite, including but not limited to one or more of chlorate or sulfate. In some embodiments, the chlorite formulations described herein are substantially free of the degradation products or impurities present in commercially available technical grade chlorite, including but not limited to chlorate or sulfate.

In some embodiments, the formulations described herein are less toxic to a subject than previously reported chlorite formulations at the same concentration of chlorite, when administered by at least or greater than one of the routes of administration described herein, including but not limited to by non-topical, systemic, parenteral, or intravenous administration. In some embodiments, the toxicity of a chlorite formulation is analyzed for toxicity using an in vivo or in vitro toxicity assay, including well-known toxicity assays. In some embodiments, the chlorite formulation is analyzed for toxicity using a non-specific in vitro toxicity assay.

In another variation, toxicity is measured according to various response indicia of toxicity in a subject after administration of the chlorite formulations described herein, as compared to administration of other commercially available chlorite formulations. In some variations, toxicity is measured relative to systemic administration of chlorite formulated as WF10. In another variation, toxicity is measured relative to intravenous administration of chlorite formulated as WF10 to a subject. In some variations, toxicity is measured after administration to a mammalian subject, including but not limited to a human subject. In some variations, toxicity is measured as one or more of irritation to the surface to which the chlorite formulation is exposed, including but not limited to the gastrointestinal tract, nausea, vomiting, diarrhea, abdominal pain, hemolysis, methemoglobinemia, cyanosis, anuria, coma, convulsions, liver damage, kidney damage, loss of appetite, or weight loss. In some variations, toxicity is measured as one or more of asthenia, injection site pain, headache, rhinitis, or diarrhea. In another variation, toxicity is measured as anemia. In some variations, toxicity is measured as asthenia. In some variations, toxicity is measured as injection site reaction. In some variations, toxicity is measured as injection site pain.

III. Methods of Adjusting the pH of Formulations Sensitive to pH

Various methods can be used to adjust the pH of formulations and pharmaceutical formulations comprising chlorite. It is intended that the methods described herein can be used to produce the formulations or pharmaceutical formulations described herein for use with the present disclosure. However, the formulations and pharmaceutical formulations described herein may also be produced by other methods, and the formulations and pharmaceutical formulations described herein are not limited to those produced by the methods described herein.

Some compounds or formulations are sensitive to high local acidity or alkalinity, requiring proper methods to adjust the pH of such compounds or formulations. Preferred pH adjusting agent(s) or pH adjusting compound(s) are weak acids or weak bases having a pKa of about 4 to about 9, a pKa of about 5 to about 9, or a pKa of about 5 to about 8, or a pKa of about 6 to about 7.5. Examples include, but are not limited to a phosphate buffer having a pKa of about 4 to about 9 as well known in the field, for example, monobasic phosphates, or monosodium phosphate and/or disodium phosphate and lower alkanoic acids, for example, acetic acid or propionic acid. In some embodiments, the pH of a formulation sensitive to acidity is lowered to between about 7 and about 11.5 using a pH adjusting compound that does not expose the formulation to acidity, including but not limited to a high local acidity in the area around the pH adjusting compound. In some embodiments, the pH of a formulation sensitive to acidity is lowered to between about 7 and about 10 using a pH adjusting compound that does not expose the formulation to acidity, including but not limited to a high local acidity in the area around the pH adjusting compound. In some embodiments, the pH of a formulation sensitive to acidity is lowered to between about 7 and about 9.5 using a pH adjusting compound that does not expose the formulation to acidity, including but not limited to a high local acidity in the area around the pH adjusting compound. In some embodiments, the pH of a formulation sensitive to acidity is lowered to between about 7 and about 9.0 using a pH adjusting compound that does not expose the formulation to acidity, including but not limited to a high local acidity in the area around the pH adjusting compound. In some embodiments, the pH of a formulation sensitive to acidity is lowered to between about 7 and about 8.5 using a pH adjusting compound that does not expose the formulation to acidity, including but not limited to a high local acidity in the area around the pH adjusting compound. In some embodiments, the pH of a formulation sensitive to acidity is lowered to between about 7.1 and about 7.7 using a pH adjusting compound that does not expose the formulation to acidity, including but not limited to a high local acidity in the area around the pH adjusting compound.

"High local acidity," as used herein, refers to the pKa of one or more molecules local to a chlorite molecule, as opposed to the overall acidity of a solution as would be measured, for example, using a pH meter. To determine whether a pH-adjusting agent will subject chlorite to high local acidity, the pKa of the pH adjusting agent can be identified using, for example, the CRC Handbook of Chemistry and Physics (86th Edition, David R. Lide ed., CRC Press, 2005).

Lowering the pH of chlorite formulations has been challenging because many pH adjusting agents expose compounds or formulations to high acidity in the local area of the molecules of the pH-adjusting compound. In the presence of high local acidity, some amount of non-chlorite compounds are generated, e.g., chlorate and/or chlorine dioxide. See, e.g., Ullmann's Encyclopedia of Industrial Chemistry, Vol. A6, Ed. Wolfgang Gerhartz, 5th Ed. (1986), which is incorporated herein by reference in its entirety. Such degradation products may not be desired in formulations for parenteral or systemic administration to physiological systems, e.g., because they are not inactive in physiological systems. Some such degradation products result in toxicity, including but not limited to the toxicities, including but not limited to non-specific toxicity, described herein.

Unless the context makes clear, the pH of any of the formulations or pharmaceutical formulations described herein may be adjusted using the methods described herein.

In some variations, the activity of a therapeutic agent, including but not limited to chlorite, is diminished by exposure to high local acidity. "Diminished activity," as used herein, refers to an activity of a therapeutic agent that is qualitatively or quantitatively inferior to that of the therapeutic agent prior to the exposure to high local acidity. As one example, a changed activity that is qualitatively or quantitatively inferior to that of the therapeutic agent prior to the exposure to high local acidity would be a lesser efficacy of wound healing, or a lesser efficacy in treating one or more of the diseases or conditions described herein. In some variations, the changed activity is any of at least or greater than about 3%, at least or greater than about 5%, at least or greater than about 10%, at least or greater than about 15%, at least or greater than about 20%, or at least or greater than about 25% lower than the activity of the therapeutic agent prior to the exposure to high local acidity. In some variations, the changed activity is at least or greater than about 5% lower than the activity of the therapeutic agent prior to the exposure to high local acidity.

In some embodiments, the pH of a chlorite formulation is adjusted to any one or more of the pH levels described in the formulations section or elsewhere herein. In some embodiments, the pH of a chlorite formulation described between about 7 and about 11.5. In some embodiments, the method comprises lowering the pH of a formulation comprising chlorite to any of between about between about 7 and about 11; between about 7 and about 10.5; between about 7 and about 10; between about 7 and about 9.5; between about 7 and about 9; between about 7 and about 8.5; between about 7 and about 8.0; between about 7 and about 7.5; between about 7.5 and about 8; between about 7.5 and about 8.5; between about 7 and about 8; between about 7.1 and about 7.7; between about 7.2 and about 7.6; between about 7.3 and about 7.5; between about 8 and about 9; between about 8 and about 8.5; between about 8.5 and about 9; about 7.0; about 7.1; about 7.2; about 7.3; about 7.4; about 7.5; about 7.6; about 7.7; about 7.8; about 7.9; about 8.0; about 8.1; about 8.2; about 8.3; about 8.4; about 8.5; about 8.6; about 8.7; about 8.8; or about 8.9 using a pH adjusting agent that does not expose the chlorite to a high local acidity. In some embodiments, the method comprises lowering the pH of a formulation comprising chlorite to between about 7 and about 8.5. In some embodiments, the method comprises lowering the pH of a formulation comprising chlorite to between about 7 and about 8.0. In some embodiments, the method comprises lowering the pH of a formulation comprising chlorite to between about 7.1 and about 7.7. In some embodiments, the method comprises lowering the pH of a formulation comprising chlorite to about 7.4.

In one non-limiting example, the pH of a mixture comprising chlorite is adjusted using a pH adjusting agent that does not subject the chlorite to a local pH of below 7 when exposed to the mixture comprising chlorite. In some embodiments, the pH adjusting agent is monosodium phosphate, disodium phosphate, or a mixture thereof. In some embodiments, monosodium phosphate and/or disodium phosphate is used as a solid or in solution. In some embodiments, the pH adjusting agent is acetic acid.

In some embodiments, the pH of chlorite is adjusted by adding chlorite or an aqueous mixture comprising chlorite to a solution containing buffer. In some embodiments, the pH of chlorite is adjusted by adding chlorite or an aqueous mixture comprising chlorite to a solution of a phosphate buffer.

In some variations, one or more pH-adjusting agents are used to adjust the pH of a chlorite solution or mixture, and the resulting solution or mixture is analyzed for the presence of degradation products of chlorite, including but not limited to degradation products generated by high local acidity. In some variations, pH-adjusting agents such as acetic acid, monosodium phosphate, and/or disodium phosphate are used to adjust the pH of a chlorite solution or mixture, and the resulting solution or mixture is analyzed for the presence of chlorate or chlorine dioxide.

In some embodiments, the resulting solution or mixture is analyzed for degradation products using well known analytical methods such as HPLC, mass spectrometry, etc. In some embodiments, the resulting solution or mixture is analyzed for degradation products using a toxicity assay, including well-known toxicity assays. In some embodiments, the resulting solution or mixture is analyzed for impurities using a non-specific toxicity assay.

In some embodiments, the pH of a chlorite formulation is adjusted after a chlorite purification step. In some embodiments, the pH of a chlorite formulation is adjusted to between about 7 and about 11.5 without the generation of chlorite degradation products that are a result of high local acidity. In some embodiments, the pH of a chlorite formulation is adjusted to between about 7 and about 8.0 without the generation of chlorite degradation products that are a result of high local acidity. In some embodiments, the pH of the chlorite formulation is adjusted to any of between about 7 and about 11; between about 7 and about 10.5; between about 7 and about 10; between about 7 and about 9.5; between about 7 and about 9; between about 7 and about 8.5; between about 7 and about 8; between about 7 and about 7.5; between about 7.5 and about 8; between about 7.5 and about 8.5; between about 7 and about 8; between about 8 and about 9; between about 8 and about 8.5; or between about 8.5 and about 9 without the generation of chlorite degradation products that are a result of high local acidity.

IV. Pharmaceutical Formulations

Unless the context clearly indicates otherwise, any of the formulations described herein may be used in any of the pharmaceutical formulations described herein. In a preferred embodiment, the pharmaceutical composition can comprise: (a) chlorite; and (b) a pharmaceutically acceptable excipient. The pharmaceutical composition can further comprise a pH adjusting agent. In some embodiments, the pH adjusting agent comprises monosodium phosphate and/or disodium phosphate. The pH adjusting agent can comprise a phosphate buffer. The pH of the composition can be between about 7.1 and about 7.7, e.g., 7.4. The formulations can have low levels of harmful chlorate, e.g., the weight ratio of chlorite:chlorate can be greater than 100:1.5, greater than 100:1, greater than 99:1, greater than 97:1, or substantially free of chlorate. Such formulations can be formulated to be administered intravenously.

The pharmaceutical formulations described herein can be suitable for administration to a subject. By "suitable for administration to a subject" is meant that the pharmaceutical formulation, when obtained from a newly opened bottle and administered via the desired route, causes no greater than a clinically acceptable level of deleterious side effects.

The formulations or pharmaceutical formulations described herein can further comprise a saline solution. A saline solution, as used herein, refers to a physiologically acceptable solution with a physiologically acceptable level of sodium chloride. In some embodiments, the saline solution is isotonic.

The chlorite formulations for use with the present disclosure can be pharmaceutically acceptable chlorite formulations comprising one or more pharmaceutically acceptable excipients. Excipients, as used herein, refer to any non-chlorite, non-water, or non-saline element of a pharmaceutical formulation. Excipients include but are not limited to carriers, adjuvants, diluents, stabilizers, wetting agents, emulsifiers, buffers, preservatives, flavorings, inactive ingredients, gel formulations, erodible and non-erodible polymers, microspheres, liposomes, etc., including combinations of the foregoing, known to skilled artisans and described further herein. In some embodiments, the percent by weight of the excipient per the total volume of the formulation or pharmaceutical formulation is no greater than any of about 10%, about 9%, about 8%, about 7%, about 6%, about 5%, about 4%, about 3%, about 2%, about 1%, about 0.5%, about 0.4%, about 0.3%, about 0.2%, about 0.1%, or about 0.05%. In some embodiments, the percent by weight of the excipient per the total volume of the formulation or pharmaceutical formulation is no greater than about 1%. In some embodiments, the percent by weight of the excipient per the total volume of the formulation or pharmaceutical formulation is no greater than about 3%.

Below is a non-limiting and non-exhaustive list of excipients that are commonly used in the pharmaceutical arts. These excipients are commonly used in various types of formulations, including those formulated for intravenous, oral, intramuscular, or parenteral administration. Given the reactivity of chlorite, it is likely that some of the excipients listed below are inappropriate for a given pharmaceutical formulation. Whether or not a particular excipient is inappropriate for a given pharmaceutical formulation may depend upon the amount of the excipient being added to the pharmaceutical formulation. Before adding one or more of any excipient, including but not limited to the excipients described herein, to a pharmaceutical formulation of chlorite, it is important to consider the reactivity of the excipient with chlorite. Some organic molecules that are commonly used as excipients react with chlorite in such a way that the excipient is changed, including but not limited to a change that results in increased toxicity of the pharmaceutical formulation prior to exposure of the excipient to chlorite. In some embodiments, the pharmaceutical formulations described herein comprise one or more pharmaceutically acceptable excipients that do not react with chlorite. Preferably, the pharmaceutical formulations described herein comprise one or more pharmaceutically acceptable excipients that do not diminish the therapeutic effect of the pharmaceutical formulation relative to prior to exposure to the excipient.

The chlorite formulations described herein can comprise one or more pharmaceutically acceptable excipients that do not generate one or more of the deleterious non-chlorite elements of other commercially available chlorite formulations. In some embodiments, the chlorite formulations described herein comprise an excipient, and are substantially free of one or more of the deleterious non-chlorite elements of other commercially available chlorite formulations. The chlorite formulations described herein can comprise an excipient, and can be substantially free of one or more of the degradation products or impurities of other commercially available chlorite formulations as described herein.

The chlorite formulation can comprise a stabilizer. Stabilizers include but are not limited to agents that will do any of (1) improve the compatibility of excipients with a container, including a glass bottle or an encapsulating materials such as gelatin, (2) improve the stability of chlorite (e.g., prevent degradation), (3) improve formulation stability, or combinations thereof. Stabilizers may be selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. Amide analogues of stabilizers can also be used. The chosen stabilizer may change the hydrophobicity of the formulation (e.g., oleic acid, waxes), or improve the mixing of various components in the formulation (e.g., ethanol), control the moisture level in the formula (e.g., PVP or polyvinyl pyrrolidone), control the mobility of the phase (substances with melting points higher than room temperature such as long chain fatty acids, alcohols, esters, ethers, amides etc. or mixtures thereof; waxes), and/or improve the compatibility of the formula with encapsulating materials (e.g., oleic acid or wax). Some of these stabilizers may be used as solvents/co-solvents (e.g., ethanol). Stabilizers may be present in sufficient amount to inhibit chlorite's degradation.

The formulations described herein may contain one or more of a gelling agent or a release modifying agent.

The formulations described herein may contain one or more adjuvants appropriate for the indicated route of administration. Again, prior to the addition of any excipient to the formulations described herein, the reactivity of chlorite should be considered with respect to whether the resulting pharmaceutical formulation will be appropriate for administration via the desired route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solubilized formulation is required the therapeutic agent may be in a solvent including but not limited to polyethylene glycol of various molecular weights, propylene glycol of various molecular weights, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods and formulations described herein. The carrier or diluent may include time delay material, such as glyceryl monostearate or glyceryl distearate alone or with a wax, or other materials well known in the art. The formulations for use as described herein may also include gel formulations, erodible and non-erodible polymers, microspheres, and liposomes.

Additives and diluents normally utilized in the pharmaceutical arts can optionally be added to the pharmaceutical composition and the liquid formulation. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like. Exemplary preservatives include, but are not limited to, benzylalcohol, ethylalcohol, benzalkonium chloride, phenol, chlorobutanol, and the like. Some antioxidants provide oxygen or peroxide inhibiting agents and may be used in the formulations described herein, including but not limited to, butylated hydroxytoluene, butylhydroxyanisole, propyl gallate, ascorbic acid palmitate, a-tocopherol, and the like. Thickening agents, such as lecithin, hydroxypropylcellulose, aluminum stearate, and the like, may be used if desired, for example to improve one or more qualities of the formulation, such as the texture.

In some variations, the chlorite formulations for use with the disclosure are sterile. Sterilization can be by any method that is compatible with chlorite. In some embodiments, sterilization is via a method that does not generate a substantial amount of a degradation product of chlorite. In some embodiments, sterilization is via a method that does not cause a structural change in chlorite. In some embodiments, the formulations described herein are sterile pharmaceutical formulations for parenteral or intravenous administration. In some embodiments, the chlorite formulations described herein are sterile filtered, for example, through a sterile 0.22 micron filter.

The formulations or pharmaceutical formulations can be sterile-filterable. In some embodiments, the chlorite formulations described herein are formulated for administration by one or more of the routes of administration described herein. A formulation that is "formulated for administration" by a specified route of administration, as used herein, is a formulation that does not include pharmaceutical excipients that are considered inappropriate for the route of administration by those of skill in the relevant art. As one example, a formulation that is suitable for intravenous administration would not include a toothpaste excipient or carrier intended for topical administration, where the excipient or carrier is considered inappropriate for the specified route of administration by those of skill in the relevant art.

Chlorite-containing agent in any form disclosed herein can be provided in any suitable formulation, which can be selected according to the desired route of administration as disclosed herein. In one embodiment, the formulation of the drug product comprises purified sodium chlorite which may include a certain amount of water content, buffer such as sodium phosphate dibasic, and sterile water for injection (USP) as a vehicle. In one embodiment, the amount of purified sodium chlorite is about 5.6 mg/mL (including a batch factor to reflect the water content of the batch), the amount of sodium phosphate dibasic is about 0.107 mg/mL, and sterile water to bring the volume up to 1 mL. In certain embodiments, a formulation according to the disclosure consists essentially of purified sodium chlorite, buffer, and sterile water for injection (USP) as the vehicle. In certain embodiments, the formulated drug product is stable for up to 3 months at 25. degree. C./60% relative humidity and/or 40. degree. C./75% relative humidity conditions.

Methods of Treatment

Disclosed herein are exemplary methods of patient selection and methods of treatment with a pharmaceutical composition comprising sodium chlorite. Factors which qualify patients a members of the ALS patients subpopulation likely to be responsive to treatment with a pharmaceutical composition comprising sodium chlorite include patient age, elevated plasma CRP levels, or time since ALS symptom onset, and combinations thereof.

Also disclosed herein are methods of treating juvenile ALS. In an exemplary embodiment a method of treating juvenile ALS comprises patients with stable disease having elevated C-reactive protein (CRP) levels of at least or greater than 1.13 mg/L.

Also disclosed herein are methods of treating endometriosis. In an exemplary embodiment a method of treating endometriosis comprises administering chlorite to a subject.

In one aspect, the methods of treating ALS in a subject described herein may comprise administering to the subject chlorite at a dosage of 2 mg/kg chlorite (in the form of formulated sodium chlorite) in the active arm for five days of drug infused over 60 minutes the first month followed by three days in a row per month for the subsequent 5 months, wherein the subject is a member of the target ALS patient population. In some embodiments, the method comprises administering to the subject chlorite at a dosage of 1 mg/kg pharmaceutical composition comprising sodium chlorite. A patient may be a member of the target ALS patient population based on elevated plasma C-reactive protein (CRP) levels exceeding 1.13 mg/L, and patient age of 40-65. In some embodiments, a patient may be a member of the target ALS patient population on the basis of highly elevated plasma C-reactive protein (CRP) level (e.g. exceeding 3 mg/L), time since ALS symptom onset (e.g. greater than 12 months), age (e.g. age 40-65), or a combination thereof.

Aspects described herein include methods of treating a subject having ALS with chlorite, the method comprising a) determining whether the subject has a high plasma C-reactive protein (CRP) level by performing or having performed an assay on a plasma sample from the subject to determine if the plasma sample has at least or greater than 1.13 mg/L CRP, and if the plasma sample has at least or greater than 1.13 mg/L the subject has a high plasma CRP level, and b) if the subject has a high plasma CRP level, then administering chlorite to the subject, wherein the subject is age 40-65. Non-limiting plasma CRP levels include levels at least or greater than 1.1 mg/L, at least or greater than 1.13 mg/L at least or greater than 1.15 mg/L, at least or greater than 1.2 mg/L, at least or greater than 1.3 mg/L, at least or greater than 1.4 mg/L, at least or greater than 1.5 mg/L, at least or greater than 1.6 mg/L, at least or greater than 1.7 mg/L, at least or greater than 1.8 mg/L, at least or greater than 1.9 mg/L, at least or greater than 2.1 mg/L, at least or greater than 2.2 mg/L, at least or greater than 2.3 mg/L, at least or greater than 2.4 mg/L, at least or greater than 2.5 mg/L, at least or greater than 2.6 mg/L, at least or greater than 2.7 mg/L, at least or greater than 2.8 mg/L, at least or greater than 2.9 mg/L, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. Non-limiting plasma CRP levels include levels no more or less than 30 mg/L, no more or less than 29 mg/L, no more or less than 28 mg/L, no more or less than 27 mg/L, no more or less than 26 mg/L, no more or less than 25 mg/L, no more or less than 24 mg/L, no more or less than 23 mg/L, no more or less than 22 mg/L, no more or less than 21 mg/L, no more or less than 20 mg/L, no more or less than 15 mg/L, or no more or less than 10 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. In some methods, the subject has experienced a symptom of ALS for at least or greater than 12, or at least or greater than 18 months prior to administration of the chlorite. For instance, the subject has experienced a symptom of ALS for at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, at least or greater than 30 months, or at least or greater than 33 months. ALS symptoms include those described herein, including, without limitation, muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms. In an example embodiment, the method is performed as described in Examples 1-4.

Aspects described herein also include combination therapy with one or more neurotrophic factors. In some cases, the neurotropic factors include: neurotrophins, glial cell-line derived neurotrophic factor family ligands (GFLs), or neuropoietic cytokines. In some cases, the neurotrophic factor comprises Brain-derived neurotrophic factor (BDNF). In some cases, the BDNF promotes thymocyte survival. In some cases, the BDNF promotes survival of dorsal root ganglion neurons. In some cases, the neurotrophic factor comprises Nerve growth factor (NGF). In some cases, the NGF promotes promote myelination and the differentiation of neuron, possibly using the high-affinity receptor TrkA. In some cases, the neurotrophic factor comprises Neurotrophin-3, or Neurotrophin-4. In some cases, the neurotrophic factor comprises ciliary neurotrophic factor, glial cell line-derived neurotrophic factor (GDNF), artemin, neurturin, or persephin. In some cases, the neurotrophic factor comprises ephrin: A1, A2, A3, A4, A5, B1, B2, or B3. In some cases, the neurotrophic factor comprises epidermal growth factor, neuregulins, transforming growth factor alpha (TGFα), or transforming growth factor beta (TGFβ).

In one aspect, described herein are methods of treating ALS in a subject, the method comprising administering to the subject chlorite, wherein the subject is 40-65 years old. Also described herein are methods of treating a subject having ALS with chlorite, the method comprising determining if the subject is 40-65 years old, and if the subject is 40-65 years old, administering chlorite to the subject. In some embodiments, the method comprises not treating the subject if the subject is not 40-65 years old. In some methods, the subject has experienced a symptom of ALS for at least or greater than 12, or at least or greater than 18 months prior to administration of the chlorite. For instance, the subject has experienced a symptom of ALS for at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, at least or greater than 30 months, or at least or greater than 33 months. At least or greater than 12 months may be as high as 30, 40, 50, or 60 months, for instance, the subject has experienced a symptom of ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months. ALS symptoms include those described herein, including, without limitation, muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms of ALS. Diagnosis of ALS may be accomplished based on Electromyogram (EMG); nerve conduction; magnetic resonance imaging (MRI); spinal fluid analysis; or muscle biopsy. In some methods, a sample from the subject has a level of at least or greater than 3 mg/L CRP. At least or greater than 3 mg/L includes, without limitation, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. The subject's plasma CRP levels may be as high as 5, 6, 7, 8, 9 or 10 mg/L. For instance, the subject's plasma CRP levels may be 3 mg/L to 10 mg/L, 3.1 mg/L to 10 mg/L, 3.2 mg/L to 10 mg/L, 3.3 mg/L to 10 mg/L, 3.4 mg/L to 10 mg/L, 3.5 mg/L to 10 mg/L, 3.6 mg/L to 10 mg/L, 3.7 mg/L to 10 mg/L, 3.8 mg/L to 10 mg/L, 3.9 mg/L to 10 mg/L, 4 mg/L to 10 mg/L, 4.1 mg/L to 10 mg/L, 4.2 mg/L to 10 mg/L, 4.3 mg/L to 10 mg/L, 4.4 mg/L to 10 mg/L, 4.5 mg/L to 10 mg/L, 4.6 mg/L to 10 mg/L, 4.7 mg/L to 10 mg/L, 4.8 mg/L to 10 mg/L, 4.9 mg/L to 10 mg/L, 5 mg/L to 10 mg/L, 3 mg/L to 8 mg/L, 3.1 mg/L to 8 mg/L, 3.2 mg/L to 8 mg/L, 3.3 mg/L to 8 mg/L, 3.4 mg/L to 8 mg/L, 3.5 mg/L to 8 mg/L, 3.6 mg/L to 8 mg/L, 3.7 mg/L to 8 mg/L, 3.8 mg/L to 8 mg/L, 3.9 mg/L to 8 mg/L, 4 mg/L to 8 mg/L, 4.1 mg/L to 8 mg/L, 4.2 mg/L to 8 mg/L, 4.3 mg/L to 8 mg/L, 4.4 mg/L to 8 mg/L, 4.5 mg/L to 8 mg/L, 4.6 mg/L to 8 mg/L, 4.7 mg/L to 8 mg/L, 4.8 mg/L to 8 mg/L, 4.9 mg/L to 8 mg/L, or 5 mg/L to 8 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. In an example embodiment, the method is performed as described in Examples 1-4.

In one aspect, described herein are methods of treating ALS in a subject, the method comprising administering to the subject chlorite, wherein the subject is age 40-65. In another aspect, the method may comprise determining if the subject has an elevated plasma C-reactive protein (CRP) level as indicated by a plasma sample from the subject having at least or greater than 3 mg/L CRP, and administering to the subject chlorite, wherein the subject is age 40-65. In another aspect, the method may comprise determining if the subject has experienced a symptom of ALS for at least or greater than 12 months and administering to the subject chlorite, wherein the subject is age 40-65. In a further aspect, the method may comprise determining if the subject has an elevated plasma C-reactive protein (CRP) level as indicated by a plasma sample from the subject having at least or greater than 3 mg/L CRP determining if the subject has experienced a symptom of ALS for at least or greater than 12 months and administering to the subject chlorite, wherein the subject is age 40-65.

In some embodiments, the subject is age 40-65, for example, age 45-65, 50-65, 55-65, 60-65, 45-60, 45-55, or 45-50. In some embodiments, the subject is up to age 65, for example, age 20-65, 25-65, 30-65, 35-65, 40-65, 45-65, 50-65, 55-65, 60-65, 20-60, 20-55, 20-50, 20-45, 20-40, 20-35, 20-30, 20-25, 25-65, 25-60, 25-55, 25-50, 25-45, 25-40, 25-35, 25-30, 30-65, 30-60, 30-55, 30-50, 30-45, 30-40, 30-35, 35-65, 35-60, 35-55, 35-50, 35-45, 35-40, 40-65, 40-60, 40-55, 40-50, 40-45, 45-65, 45-60, 45-55, 45-50, 50-65, 50-60, 50-55, 55-65, 55-60, or 60-65.

Also described herein are methods of treating a subject having ALS with chlorite, the method comprising a) determining whether the subject has an elevated plasma C-reactive protein (CRP) level by performing or having performed an assay on a plasma sample from the subject to determine if the plasma sample has at least or greater than 3 mg/L CRP, and if the plasma sample has at least or greater than 3 mg/L the subject has an elevated plasma CRP level, and b) if the subject has an elevated plasma CRP level, then administering chlorite to the subject wherein the subject is age 40-65. Non-limiting elevated plasma CRP levels include levels at least or greater than 3 mg/L, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. The elevated plasma CRP levels may be as high as 5, 6, 7, 8, 9 or 10 mg/L. For instance, the elevated plasma CRP levels may be 3 mg/L to 10 mg/L, 3.1 mg/L to 10 mg/L, 3.2 mg/L to 10 mg/L, 3.3 mg/L to 10 mg/L, 3.4 mg/L to 10 mg/L, 3.5 mg/L to 10 mg/L, 3.6 mg/L to 10 mg/L, 3.7 mg/L to 10 mg/L, 3.8 mg/L to 10 mg/L, 3.9 mg/L to 10 mg/L, 4 mg/L to 10 mg/L, 4.1 mg/L to 10 mg/L, 4.2 mg/L to 10 mg/L, 4.3 mg/L to 10 mg/L, 4.4 mg/L to 10 mg/L, 4.5 mg/L to 10 mg/L, 4.6 mg/L to 10 mg/L, 4.7 mg/L to 10 mg/L, 4.8 mg/L to 10 mg/L, 4.9 mg/L to 10 mg/L, 5 mg/L to 10 mg/L, 3 mg/L to 8 mg/L, 3.1 mg/L to 8 mg/L, 3.2 mg/L to 8 mg/L, 3.3 mg/L to 8 mg/L, 3.4 mg/L to 8 mg/L, 3.5 mg/L to 8 mg/L, 3.6 mg/L to 8 mg/L, 3.7 mg/L to 8 mg/L, 3.8 mg/L to 8 mg/L, 3.9 mg/L to 8 mg/L, 4 mg/L to 8 mg/L, 4.1 mg/L to 8 mg/L, 4.2 mg/L to 8 mg/L, 4.3 mg/L to 8 mg/L, 4.4 mg/L to 8 mg/L, 4.5 mg/L to 8 mg/L, 4.6 mg/L to 8 mg/L, 4.7 mg/L to 8 mg/L, 4.8 mg/L to 8 mg/L, 4.9 mg/L to 8 mg/L, or 5 mg/L to 8 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. In an example embodiment, the method is performed as described in Examples 1-4.

Also described herein are methods of treating a subject having ALS with chlorite, the method comprising a) determining the length of time a subject has experienced a symptom of ALS for at least or greater than 12 months, and b) administering to the subject chlorite, wherein the subject is age 40-65. Non-limiting examples of ALS symptom duration include wherein subject has experienced a symptom of ALS for at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, or at least or greater than 30 months. At least or greater than 12 months may be as high as 30, 40, 50, or 60 months, for instance, the subject has experienced a symptom of ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months. ALS symptoms include those described herein, including, without limitation, muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms.

Also described herein are methods of treating a subject having ALS with chlorite, the method comprising a) determining if the subject has an elevated plasma C-reactive protein (CRP) level as indicated by a plasma sample from the subject having at least or greater than 3 mg/L CRP; b) determining the length of time a subject has experienced a symptom of ALS for at least or greater than 12 months, and c) administering to the subject chlorite, wherein the subject is age 40-65. Also described herein are methods of treating a subject having ALS with chlorite, the method comprising a) determining whether the subject has an elevated plasma C-reactive protein (CRP) level by performing or having performed an assay on a plasma sample from the subject to determine if the plasma sample has at least or greater than 3 mg/L CRP, and if the plasma sample has at least or greater than 3 mg/L the subject has an elevated plasma CRP level, and b) if the subject has an elevated plasma CRP level, then administering chlorite to the subject wherein the subject is age 40-65. Non-limiting elevated plasma CRP levels include levels at least or greater than 3 mg/L, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. The elevated plasma CRP levels may be as high as 5, 6, 7, 8, 9 or 10 mg/L. For instance, the elevated plasma CRP levels may be 3 mg/L to 10 mg/L, 3.1 mg/L to 10 mg/L, 3.2 mg/L to 10 mg/L, 3.3 mg/L to 10 mg/L, 3.4 mg/L to 10 mg/L, 3.5 mg/L to 10 mg/L, 3.6 mg/L to 10 mg/L, 3.7 mg/L to 10 mg/L, 3.8 mg/L to 10 mg/L, 3.9 mg/L to 10 mg/L, 4 mg/L to 10 mg/L, 4.1 mg/L to 10 mg/L, 4.2 mg/L to 10 mg/L, 4.3 mg/L to 10 mg/L, 4.4 mg/L to 10 mg/L, 4.5 mg/L to 10 mg/L, 4.6 mg/L to 10 mg/L, 4.7 mg/L to 10 mg/L, 4.8 mg/L to 10 mg/L, 4.9 mg/L to 10 mg/L, 5 mg/L to 10 mg/L, 3 mg/L to 8 mg/L, 3.1 mg/L to 8 mg/L, 3.2 mg/L to 8 mg/L, 3.3 mg/L to 8 mg/L, 3.4 mg/L to 8 mg/L, 3.5 mg/L to 8 mg/L, 3.6 mg/L to 8 mg/L, 3.7 mg/L to 8 mg/L, 3.8 mg/L to 8 mg/L, 3.9 mg/L to 8 mg/L, 4 mg/L to 8 mg/L, 4.1 mg/L to 8 mg/L, 4.2 mg/L to 8 mg/L, 4.3 mg/L to 8 mg/L, 4.4 mg/L to 8 mg/L, 4.5 mg/L to 8 mg/L, 4.6 mg/L to 8 mg/L, 4.7 mg/L to 8 mg/L, 4.8 mg/L to 8 mg/L, 4.9 mg/L to 8 mg/L, or 5 mg/L to 8 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. Non-limiting examples of ALS symptom duration include wherein subject has experienced a symptom of ALS for at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, or at least or greater than 30 months. At least or greater than 12 months may be as high as 30, 40, 50, or 60 months, for instance, the subject has experienced a symptom of ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months. ALS symptoms include those described herein, including, without limitation, muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms.

In one aspect, described herein are methods of treating ALS in a subject, the method comprising administering to the subject chlorite, wherein the subject has an elevated plasma C-reactive protein (CRP) level as indicated by a plasma sample from the subject having at least or greater than 3 mg/L CRP. Also described herein are methods of treating a subject having ALS with chlorite, the method comprising a) determining whether the subject has an elevated plasma C-reactive protein (CRP) level by performing or having performed an assay on a plasma sample from the subject to determine if the plasma sample has at least or greater than 3 mg/L CRP, and if the plasma sample has at least or greater than 3 mg/L the subject has an elevated plasma CRP level, and b) if the subject has an elevated plasma CRP level, then administering chlorite to the subject. Non-limiting elevated plasma CRP levels include levels at least or greater than 3 mg/L, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. The elevated plasma CRP levels may be as high as 5, 6, 7, 8, 9 or 10 mg/L. For instance, the elevated plasma CRP levels may be 3 mg/L to 10 mg/L, 3.1 mg/L to 10 mg/L, 3.2 mg/L to 10 mg/L, 3.3 mg/L to 10 mg/L, 3.4 mg/L to 10 mg/L, 3.5 mg/L to 10 mg/L, 3.6 mg/L to 10 mg/L, 3.7 mg/L to 10 mg/L, 3.8 mg/L to 10 mg/L, 3.9 mg/L to 10 mg/L, 4 mg/L to 10 mg/L, 4.1 mg/L to 10 mg/L, 4.2 mg/L to 10 mg/L, 4.3 mg/L to 10 mg/L, 4.4 mg/L to 10 mg/L, 4.5 mg/L to 10 mg/L, 4.6 mg/L to 10 mg/L, 4.7 mg/L to 10 mg/L, 4.8 mg/L to 10 mg/L, 4.9 mg/L to 10 mg/L, 5 mg/L to 10 mg/L, 3 mg/L to 8 mg/L, 3.1 mg/L to 8 mg/L, 3.2 mg/L to 8 mg/L, 3.3 mg/L to 8 mg/L, 3.4 mg/L to 8 mg/L, 3.5 mg/L to 8 mg/L, 3.6 mg/L to 8 mg/L, 3.7 mg/L to 8 mg/L, 3.8 mg/L to 8 mg/L, 3.9 mg/L to 8 mg/L, 4 mg/L to 8 mg/L, 4.1 mg/L to 8 mg/L, 4.2 mg/L to 8 mg/L, 4.3 mg/L to 8 mg/L, 4.4 mg/L to 8 mg/L, 4.5 mg/L to 8 mg/L, 4.6 mg/L to 8 mg/L, 4.7 mg/L to 8 mg/L, 4.8 mg/L to 8 mg/L, 4.9 mg/L to 8 mg/L, or 5 mg/L to 8 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. In an example embodiment, the method is performed as described in Examples 1-4. In some methods, the subject may have experienced a symptom of ALS for at least or greater than 12 months. For instance, the subject has experienced a symptom of ALS for at least or greater than 12 months, 13 months, 14 months, 15 months, 16 months, 17 months, 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, or at least or greater than 30 months. At least or greater than 12 months may be as high as 30, 40, 50, or 60 months, for instance, the subject has experienced a symptom of ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months. ALS symptoms include those described herein, including, without limitation, muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms of ALS. Diagnosis of ALS may be accomplished based on Electromyogram (EMG); nerve conduction; magnetic resonance imaging (MRI); spinal fluid analysis; or muscle biopsy. In some methods, the subject is 40-65 years old.

In one aspect, described herein are methods of treating ALS in a subject, the method comprising administering to the subject chlorite, wherein the subject has experienced a symptom of ALS for at least or greater than 12, or at least or greater than 18 months prior to administration of the chlorite. Also described herein are methods of treating a subject having ALS with chlorite, the method comprising a) determining the length of time the subject has experienced a symptom of ALS, and b) if the subject has experienced a symptom of ALS for at least or greater than 12 or at least or greater than 18 months, then administering chlorite to the subject. For instance, the subject has experienced a symptom of ALS for at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, or at least or greater than 30 months. At least or greater than 12 months may be as high as 30, 40, 50, or 60 months, for instance, the subject has experienced a symptom of ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months. ALS symptoms include those described herein, including, without limitation, muscle weakness, muscle cramping, muscle twitching, muscle spasms, difficulty in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms of ALS. Diagnosis of ALS may be accomplished based on Electromyogram (EMG); nerve conduction; magnetic resonance imaging (MRI); spinal fluid analysis; or muscle biopsy. In some methods, a sample from the subject has a level of at least or greater than 3 mg/L CRP. At least or greater than 3 mg/L includes, without limitation, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. The subject's plasma CRP levels may be as high as 5, 6, 7, 8, 9 or 10 mg/L. For instance, the subject's plasma CRP levels may be 3 mg/L to 10 mg/L, 3.1 mg/L to 10 mg/L, 3.2 mg/L to 10 mg/L, 3.3 mg/L to 10 mg/L, 3.4 mg/L to 10 mg/L, 3.5 mg/L to 10 mg/L, 3.6 mg/L to 10 mg/L, 3.7 mg/L to 10 mg/L, 3.8 mg/L to 10 mg/L, 3.9 mg/L to 10 mg/L, 4 mg/L to 10 mg/L, 4.1 mg/L to 10 mg/L, 4.2 mg/L to 10 mg/L, 4.3 mg/L to 10 mg/L, 4.4 mg/L to 10 mg/L, 4.5 mg/L to 10 mg/L, 4.6 mg/L to 10 mg/L, 4.7 mg/L to 10 mg/L, 4.8 mg/L to 10 mg/L, 4.9 mg/L to 10 mg/L, 5 mg/L to 10 mg/L, 3 mg/L to 8 mg/L, 3.1 mg/L to 8 mg/L, 3.2 mg/L to 8 mg/L, 3.3 mg/L to 8 mg/L, 3.4 mg/L to 8 mg/L, 3.5 mg/L to 8 mg/L, 3.6 mg/L to 8 mg/L, 3.7 mg/L to 8 mg/L, 3.8 mg/L to 8 mg/L, 3.9 mg/L to 8 mg/L, 4 mg/L to 8 mg/L, 4.1 mg/L to 8 mg/L, 4.2 mg/L to 8 mg/L, 4.3 mg/L to 8 mg/L, 4.4 mg/L to 8 mg/L, 4.5 mg/L to 8 mg/L, 4.6 mg/L to 8 mg/L, 4.7 mg/L to 8 mg/L, 4.8 mg/L to 8 mg/L, 4.9 mg/L to 8 mg/L, or 5 mg/L to 8 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. In an example embodiment, the method is performed as described in Examples 1-4. In some methods, the subject is 40-65 years old.

In one aspect, described herein are methods of treating amyotrophic lateral sclerosis (ALS) in a subject, the method comprising administering to the subject chlorite, wherein the subject: i) has an elevated plasma C-reactive protein (CRP) level as indicated by a plasma sample from the subject having at least or greater than 3 mg/L CRP, and ii) has experienced a symptom of ALS for at least or greater than 12 or at least or greater than 18 months prior to administration of the chlorite. Also described herein are methods of treating a subject having ALS with chlorite, the method comprising a) determining whether the subject has an elevated plasma C-reactive protein (CRP) level by: performing or having performed an assay on a plasma sample from the subject to determine if the plasma sample has at least or greater than 3 mg/L CRP, and if the plasma sample has at least or greater than 3 mg/L the subject has an elevated plasma CRP level, b) determining the length of time the subject has experienced a symptom of ALS, and c) if the subject has an elevated plasma CRP level and has experienced a symptom of ALS for at least or greater than 12 or at least or greater than 18 months, then administering chlorite to the subject. Non-limiting elevated plasma CRP levels include levels at least or greater than 3 mg/L, at least or greater than 3.1 mg/L, at least or greater than 3.2 mg/L, at least or greater than 3.3 mg/L, at least or greater than 3.4 mg/L, at least or greater than 3.5 mg/L, at least or greater than 3.6 mg/L, at least or greater than 3.7 mg/L, at least or greater than 3.8 mg/L, at least or greater than 3.9 mg/L, at least or greater than 4 mg/L, at least or greater than 4.1 mg/L, at least or greater than 4.2 mg/L, at least or greater than 4.3 mg/L, at least or greater than 4.4 mg/L, at least or greater than 4.5 mg/L, at least or greater than 4.6 mg/L, at least or greater than 4.7 mg/L, at least or greater than 4.8 mg/L, at least or greater than 4.9 mg/L, or at least or greater than 5 mg/L. The elevated plasma CRP levels may be as high as 5, 6, 7, 8, 9 or 10 mg/L. For instance, the elevated plasma CRP levels may be 3 mg/L to 10 mg/L, 3.1 mg/L to 10 mg/L, 3.2 mg/L to 10 mg/L, 3.3 mg/L to 10 mg/L, 3.4 mg/L to 10 mg/L, 3.5 mg/L to 10 mg/L, 3.6 mg/L to 10 mg/L, 3.7 mg/L to 10 mg/L, 3.8 mg/L to 10 mg/L, 3.9 mg/L to 10 mg/L, 4 mg/L to 10 mg/L, 4.1 mg/L to 10 mg/L, 4.2 mg/L to 10 mg/L, 4.3 mg/L to 10 mg/L, 4.4 mg/L to 10 mg/L, 4.5 mg/L to 10 mg/L, 4.6 mg/L to 10 mg/L, 4.7 mg/L to 10 mg/L, 4.8 mg/L to 10 mg/L, 4.9 mg/L to 10 mg/L, 5 mg/L to 10 mg/L, 3 mg/L to 8 mg/L, 3.1 mg/L to 8 mg/L, 3.2 mg/L to 8 mg/L, 3.3 mg/L to 8 mg/L, 3.4 mg/L to 8 mg/L, 3.5 mg/L to 8 mg/L, 3.6 mg/L to 8 mg/L, 3.7 mg/L to 8 mg/L, 3.8 mg/L to 8 mg/L, 3.9 mg/L to 8 mg/L, 4 mg/L to 8 mg/L, 4.1 mg/L to 8 mg/L, 4.2 mg/L to 8 mg/L, 4.3 mg/L to 8 mg/L, 4.4 mg/L to 8 mg/L, 4.5 mg/L to 8 mg/L, 4.6 mg/L to 8 mg/L, 4.7 mg/L to 8 mg/L, 4.8 mg/L to 8 mg/L, 4.9 mg/L to 8 mg/L, or 5 mg/L to 8 mg/L. Non-limiting methods of determining plasma level in a sample include latex agglutination, latex-enhanced nephelometry, photometric measurement of antigen-antibody reaction, and highly sensitive Near Infrared Particle Immunoassay rate methodology. In an example embodiment, the method is performed as described in Examples 1-4. In some cases, at least or greater than 12 months includes at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, or at least or greater than 30 months. At least or greater than 12 months may be as high as 30, 40, 50, or 60 months, for instance, the subject has experienced a symptom of ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months. ALS symptoms include those described herein, including, without limitation, muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, and combinations of two or more thereof. Determining the length of time the subject has experienced a symptom of ALS may comprise reviewing the subject's medical history for symptoms of ALS, reviewing the subject's medical history for a diagnosis of ALS, or inquiring from the subject as to when they first began to experience symptoms of ALS. Diagnosis of ALS may be accomplished based on Electromyogram (EMG); nerve conduction; magnetic resonance imaging (MRI); spinal fluid analysis; or muscle biopsy. In some methods, the subject is 40-65 years old.

In some methods, the subject may have experienced a symptom of ALS for at least or greater than 12 months or at least or greater than 18 months, and may also have an elevated plasma CRP level of at least or greater than 3.0 mg/L; for example, between 12-24 months or between 18-21 months since symptom onset and a CRP level between 3.0-10 mg/L; between 12-24 months or between 18-21 months since symptom onset and a CRP level between 3.0-5.0 mg/L; between 12-24 months or between 18-21 months since symptom onset and a CRP level between 3.0-4.0 mg/L; between 12-24 months or between 18-21 months since symptom onset and a CRP level between 3.1-5.0 mg/L; between 12-24 months or between 18-21 months since symptom onset and a CRP level between 3.2-5.0 mg/L; between 12-24 months or between 18-21 months since symptom onset and a CRP level between 3.3-5.0 mg/L; between 12-24 months or between 18-21 months since symptom onset and a CRP level between 3.3-5.0 mg/L; between 12-24 months or between 18-21 months since symptom onset and a CRP level between 3.4-5.0 mg/L; between 12-24 months or between 18-21 months since symptom onset and a CRP level between 3.5-5.0 mg/L; between 12-24 months or between 18-21 months since symptom onset and a CRP level between 3.6-5.0 mg/L; between 12-24 months or between 18-21 months since symptom onset and a CRP level between 3.7-5.0 mg/L; between 12-24 months or between 18-21 months since symptom onset and a CRP level between 3.8-5.0 mg/L; between 12-24 months or between 18-21 months since symptom onset and a CRP level between 3.9-5.0 mg/L; between 12-24 months or between 18-21 months since symptom onset and a CRP level between 4-10 mg/L; or between 12-24 months or between 18-21 months since symptom onset and a CRP level between 4.1-5.0 mg/L; between 12-24 months or between 18-21 months since symptom onset and a CRP level between 4.2-5.0 mg/L; between 12-24 months or between 18-21 months since symptom onset and a CRP level between 4.3-5.0 mg/L; between 12-24 months or between 18-21 months since symptom onset and a CRP level between 4.3-5.0 mg/L; between 12-24 months or between 18-21 months since symptom onset and a CRP level between 4.4-5.0 mg/L; between 12-24 months or between 18-21 months since symptom onset and a CRP level between 4.5-5.0 mg/L; between 12-24 months or between 18-21 months since symptom onset and a CRP level between 4.6-5.0 mg/L; between 12-24 months or between 18-21 months since symptom onset and a CRP level between 4.7-5.0 mg/L; between 12-24 months or between 18-21 months since symptom onset and a CRP level between 4.8-5.0 mg/L; between 12-24 months or between 18-21 months since symptom onset and a CRP level between 4.9-5.0 mg/L. In some methods, the subject is 40-65 years old.

In some methods, the subject may have experienced a symptom of ALS for at least or greater than 21 months, and may also have an elevated plasma CRP level of at least or greater than 3.0 mg/L; for example, between 21-36 months since symptom onset and a CRP level between 3.0-10 mg/L; between 21-36 months since symptom onset and a CRP level between 3.0-5.0 mg/L; between 21-36 months since symptom onset and a CRP level between 3.0-4.0 mg/L; between 21-36 months since symptom onset and a CRP level between 3.1-5.0 mg/L; between 21-36 months since symptom onset and a CRP level between 3.2-5.0 mg/L; between 21-36 months since symptom onset and a CRP level between 3.3-5.0 mg/L; between 21-36 months since symptom onset and a CRP level between 3.3-5.0 mg/L; between 21-36 months since symptom onset and a CRP level between 3.4-5.0 mg/L; between 21-36 months since symptom onset and a CRP level between 3.5-5.0 mg/L; between 21-36 months since symptom onset and a CRP level between 3.6-5.0 mg/L; between 21-36 months since symptom onset and a CRP level between 3.7-5.0 mg/L; between 21-36 months since symptom onset and a CRP level between 3.8-5.0 mg/L; between 21-36 months since symptom onset and a CRP level between 3.9-5.0 mg/L; between 21-36 months since symptom onset and a CRP level between 4-10 mg/L; or between 21-36 months since symptom onset and a CRP level between 4.1-5.0 mg/L; between 21-36 months since symptom onset and a CRP level between 4.2-5.0 mg/L; between 21-36 months since symptom onset and a CRP level between 4.3-5.0 mg/L; between 21-36 months since symptom onset and a CRP level between 4.3-5.0 mg/L; between 21-36 months since symptom onset and a CRP level between 4.4-5.0 mg/L; between 21-36 months since symptom onset and a CRP level between 4.5-5.0 mg/L; between 21-36 months since symptom onset and a CRP level between 4.6-5.0 mg/L; between 21-36 months since symptom onset and a CRP level between 4.7-5.0 mg/L; between 21-36 months since symptom onset and a CRP level between 4.8-5.0 mg/L; between 21-36 months since symptom onset and a CRP level between 4.9-5.0 mg/L. In some methods, the subject is 40-65 years old.

In some methods, the subject may have experienced a symptom of ALS for at least or greater than 12 months or at least or greater than 18 months, and may also have an elevated plasma CRP level of at least or greater than 4.0 mg/L; for example, between 12-24 months or between 18-21 months since symptom onset and a CRP level between 4.0-10 mg/L; between 12-24 months or between 18-21 months since symptom onset and a CRP level between 4.0-6.0 mg/L; between 12-24 months or between 18-21 months since symptom onset and a CRP level between 4.0-5.0 mg/L; between 12-24 months or between 18-21 months since symptom onset and a CRP level between 4.1-6.0 mg/L; between 12-24 months or between 18-21 months since symptom onset and a CRP level between 4.2-6.0 mg/L; between 12-24 months or between 18-21 months since symptom onset and a CRP level between 4.3-6.0 mg/L; between 12-24 months or between 18-21 months since symptom onset and a CRP level between 4.3-6.0 mg/L; between 12-24 months or between 18-21 months since symptom onset and a CRP level between 4.4-6.0 mg/L; between 12-24 months or between 18-21 months since symptom onset and a CRP level between 4.5-6.0 mg/L; between 12-24 months or between 18-21 months since symptom onset and a CRP level between 4.6-6.0 mg/L; between 12-24 months or between 18-21 months since symptom onset and a CRP level between 4.7-6.0 mg/L; between 12-24 months or between 18-21 months since symptom onset and a CRP level between 4.8-6.0 mg/L; between 12-24 months or between 18-21 months since symptom onset and a CRP level between 4.9-6.0 mg/L; between 12-24 months or between 18-21 months since symptom onset and a CRP level between 4-10 mg/L; or between 12-24 months or between 18-21 months since symptom onset and a CRP level between 5.1-6.0 mg/L; between 12-24 months or between 18-21 months since symptom onset and a CRP level between 5.2-6.0 mg/L; between 12-24 months or between 18-21 months since symptom onset and a CRP level between 5.3-6.0 mg/L; between 12-24 months or between 18-21 months since symptom onset and a CRP level between 5.3-6.0 mg/L; between 12-24 months or between 18-21 months since symptom onset and a CRP level between 5.4-6.0 mg/L; between 12-24 months or between 18-21 months since symptom onset and a CRP level between 5.5-6.0 mg/L; between 12-24 months or between 18-21 months since symptom onset and a CRP level between 5.6-6.0 mg/L; between 12-24 months or between 18-21 months since symptom onset and a CRP level between 5.7-6.0 mg/L; between 12-24 months or between 18-21 months since symptom onset and a CRP level between 5.8-6.0 mg/L; between 12-24 months or between 18-21 months since symptom onset and a CRP level between 5.9-6.0 mg/L. In some methods, the subject is 40-65 years old.

In some methods, the subject may have experienced a symptom of ALS for at least or greater than 18 months, and may also have an elevated plasma CRP level of at least or greater than 4.0 mg/L; for example, between 21-36 months since symptom onset and a CRP level between 4.0-10 mg/L; between 21-36 months since symptom onset and a CRP level between 4.0-6.0 mg/L; between 21-36 months since symptom onset and a CRP level between 4.0-5.0 mg/L; between 21-36 months since symptom onset and a CRP level between 4.1-6.0 mg/L; between 21-36 months since symptom onset and a CRP level between 4.2-6.0 mg/L; between 21-36 months since symptom onset and a CRP level between 4.3-6.0 mg/L; between 21-36 months since symptom onset and a CRP level between 4.3-6.0 mg/L; between 21-36 months since symptom onset and a CRP level between 4.4-6.0 mg/L; between 21-36 months since symptom onset and a CRP level between 4.5-6.0 mg/L; between 21-36 months since symptom onset and a CRP level between 4.6-6.0 mg/L; between 21-36 months since symptom onset and a CRP level between 4.7-6.0 mg/L; between 21-36 months since symptom onset and a CRP level between 4.8-6.0 mg/L; between 21-36 months since symptom onset and a CRP level between 4.9-6.0 mg/L; between 21-30 months since symptom onset and a CRP level between 4-10 mg/L; or between 21-36 months since symptom onset and a CRP level between 5.1-6.0 mg/L; between 21-36 months since symptom onset and a CRP level between 5.2-6.0 mg/L; between 21-36 months since symptom onset and a CRP level between 5.3-6.0 mg/L; between 21-36 months since symptom onset and a CRP level between 5.3-6.0 mg/L; between 21-36 months since symptom onset and a CRP level between 5.4-6.0 mg/L; between 21-36 months since symptom onset and a CRP level between 5.5-6.0 mg/L; between 21-36 months since symptom onset and a CRP level between 5.6-6.0 mg/L; between 21-36 months since symptom onset and a CRP level between 5.7-6.0 mg/L; between 21-36 months since symptom onset and a CRP level between 5.8-6.0 mg/L; between 21-36 months since symptom onset and a CRP level between 5.9-6.0 mg/L. In some methods, the subject is 40-65 years old.

In any of the methods described herein, treating comprises reducing a symptom of ALS, reducing progression of ALS, or increasing life expectancy in the subject, or a combination thereof. In any of the methods described herein, treating results in no disease progression in the subject after administration using the ALS functional rating scale (ALSFRS-R). In some methods, treatment may comprise assessing the subject's disease progression using the ALS functional rating scale (ALSFRS-R); and halting of disease progression may include a decrease of not more than 3 points in the ALSFRS-R over a six-month period. Treatment may also comprise halting disease progression. Treatment may also comprise change in pulmonary function as measured by slow vital capacity readings, or a longer time to tracheotomy, as compared to a subject that has not been treated with chlorite. Treatment may also comprise reducing a level of blood inflammatory biomarkers in the subject. Treatment may also comprise reducing CRP levels in the subject.

In any of the methods described herein, treating comprises halting of ALS disease progression, including halting loss in patient vital capacity. Treating may comprise halting loss in patient vital capacity, including, for example, a loss of not more than 0.05%, 0.075%, 0.1%, 0.125%, 0.15%, 0.2%, 0.225%, 0.25%, 0.275%, 0.3%, 0.5%, 0.75%, 1%, 1.25%, 1.5%, 1.75%, 2%, 3%, 4%, 5%, 6%, 7%, 8%, 9%, 10%, 12.5%, 15%, 17.5%, 20%, 22.5%, or 25% over a six month period.

In any of the methods described herein, the subject is diagnosed, or has been diagnosed, with ALS. The subject may be diagnosed based on Electromyogram (EMG); nerve conduction; magnetic resonance imaging (MRI); spinal fluid analysis; or muscle biopsy. In some methods, the subject is or has been diagnosed with ALS at least or greater than 12 months prior to administration of the chlorite. In some cases, at least or greater than 12 months includes at least or greater than 12 months, at least or greater than 13 months, at least or greater than 14 months, at least or greater than 15 months, at least or greater than 16 months, at least or greater than 17 months, at least or greater than 18 months, at least or greater than 19 months, at least or greater than 20 months, at least or greater than 21 months, at least or greater than 22 months, at least or greater than 23 months, at least or greater than 24 months, at least or greater than 25 months, at least or greater than 26 months, at least or greater than 27 months, at least or greater than 28 months, at least or greater than 29 months, or at least or greater than 30 months. At least or greater than 12 months may be as high as 30, 40, 50, or 60 months, for instance, the subject is or has been diagnosed with ALS for 12 months to 60 months, 12 months to 50 months, 12 months to 40 months, 12 months to 30 months, 13 months to 60 months, 13 months to 50 months, 13 months to 40 months, 13 months to 30 months, 14 months to 60 months, 14 months to 50 months, 14 months to 40 months, 14 months to 30 months, 15 months to 60 months, 15 months to 50 months, 15 months to 40 months, 15 months to 30 months, 16 months to 60 months, 16 months to 50 months, 16 months to 40 months, 16 months to 30 months, 17 months to 60 months, 17 months to 50 months, 17 months to 40 months, 17 months to 30 months, 18 months to 60 months, 18 months to 50 months, 18 months to 40 months, 18 months to 30 months, 19 months to 60 months, 19 months to 50 months, 19 months to 40 months, 19 months to 30 months, 20 months to 60 months, 20 months to 50 months, 20 months to 40 months, 20 months to 30 months, 21 months to 60 months, 21 months to 50 months, 21 months to 40 months, 21 months to 30 months, 22 months to 60 months, 22 months to 50 months, 22 months to 40 months, 22 months to 30 months, 23 months to 60 months, 23 months to 50 months, 23 months to 40 months, 23 months to 30 months, 24 months to 60 months, 24 months to 50 months, 24 months to 40 months, 24 months to 30 months, 25 months to 60 months, 25 months to 50 months, 25 months to 40 months, or 25 months to 30 months.

In some methods chlorite comprises sodium chlorite. In some methods treating a subject with chlorite may comprise intravenously administering chlorite, or a pharmaceutically acceptable salt thereof (e.g. sodium chlorite), at a dose of 2 mg/kg over approximately 60 minutes using an infusion pump every day for five days for the first month and then for three consecutive days each month thereafter, for six months.

In some methods chlorite comprises sodium chlorite or a pharmaceutically acceptable salt thereof. In some methods treating a subject with chlorite may comprise intravenously administering chlorite, or a pharmaceutically acceptable salt thereof (e.g. sodium chlorite), at a dose of 1 mg/kg, 2 mg/kg, or 3 mg/kg, over approximately 30 minutes using an infusion pump. Treatment may further comprise administering 20 infusions over 6 cycles during a 25-week period. Cycle 1 may comprise 5 consecutive daily infusions (e.g. 5 infusions over a 1-week period). Cycles 2, 3, 4, 5, and 6 may comprise 3 consecutive daily infusions (e.g. 3 infusions over a 1-week period).

In some methods, treatment may comprise intravenously administering chlorite, or a pharmaceutically acceptable salt thereof (e.g. sodium chlorite), at a dose of 1.6, 2.0, or 3.2 mg/kg (of chlorite) as a 30-minute infusion. Treatment may further comprise administering approximately 90 such infusions approximately every other day over a 6-month period.

In some methods, treatment may comprise intravenously administering chlorite, or a pharmaceutically acceptable salt thereof (e.g., sodium chlorite), at a dose of 1.5, 2.0, 2.5, or 3.0 mg/kg (as chlorite) as a 30-minute or 60-minute infusion. Treatment may further comprise administering approximately 90 such infusions approximately every other day over a 6-month period, or 180 such infusions daily over a 6-month period.

In some methods, treatment may comprise intravenously administering chlorite, or a pharmaceutically acceptable salt thereof (e.g. sodium chlorite), such a pharmaceutical composition comprising sodium chlorite, at a dose of 1.0, 1.5, 2.0, 2.5, or 3.0 mg/kg daily as a 30-minute infusion. Treatment may further comprise administering approximately 180 such daily infusions over a 6-month period.

In some methods, treatment may comprise intravenously administering chlorite, or a pharmaceutically acceptable salt thereof (e.g. sodium chlorite), such a pharmaceutical composition comprising sodium chlorite, to a juvenile ALS patient at a dose of at a dose of 1 mg/kg, 2 mg/kg, or 3 mg/kg, over approximately 60 minutes using an infusion pump. Treatment may further comprise administering 20 infusions over 6 cycles during a 25-week period. Cycle 1 may comprise 5 consecutive daily infusions (e.g. 5 infusions over a 1-week period). Cycles 2, 3, 4, 5, and 6 may comprise 3 consecutive daily infusions (e.g. 3 infusions over a 1-week period).

In some methods, treatment may comprise intravenously administering chlorite, or a pharmaceutically acceptable salt thereof (e.g. sodium chlorite), such a pharmaceutical composition comprising sodium chlorite, to an endometriosis patient at a dose of at a dose of 1 mg/kg, 2 mg/kg, or 3 mg/kg, over approximately 60 minutes using an infusion pump. Treatment may further comprise administering 20 infusions over 6 cycles during a 25-week period. Cycle 1 may comprise 5 consecutive daily infusions (e.g. 5 infusions over a 1-week period). Cycles 2, 3, 4, 5, and 6 may comprise 3 consecutive daily infusions (e.g. 3 infusions over a 1-week period).

Treatment using the methods disclosed herein may also be accomplished using potassium chlorite or a pharmaceutically acceptable salt thereof.

In an example embodiment, the method may be performed as described in Examples 1-4 below.

EXAMPLES

Below are examples of the methods of patient selection and treatment disclosed herein. The data presented in the present disclosure is drawn from two 6-month phase 2 trials conducted with NP001 in ALS patients, which were registered at ClinicalTrials.gov (NCT01281631 for Phase 2A and NCT02794857 for Phase 2B). NP001 drug product (DP) is a clear, colorless, sterile solution of sodium chlorite and contains no preservatives. NP001 DP contains purified sodium chlorite (5.61 mg/mL, 62 mM), sodium phosphate, dibasic (0.107 mg/mL) and sterile water for injection, at a pH of 7.5 to 9.5. The active moiety is chlorite, and all clinical doses are expressed as mg/kg chlorite. A concentration of 5.61 mg/mL sodium chlorite (62 mM) translates to 4.2 mg/mL chlorite (62 mM). The formulation is packaged in 30 mL Type 1 flint glass vials with 20 mM stoppers and capped with red aluminum overseals. Each single-use 30 mL vial delivers 20 mL (nominal) of NP001. The formulation is not intended for IV administration neat. Dose preparation instructions specify combining the formulation with 0.45% sodium chloride (half normal saline obtained from commercial vendors) to achieve a total exact volume of 250 mL infusion solution prior to administration.

The data focuses on pre-study rate of disease progression, baseline plasma C-reactive protein (CRP) levels and clinical outcome in subjects receiving 2 mg/kg NP001 (a pharmaceutical composition comprising sodium chlorite) or placebo. Statistical analysis was performed using SAS 9.4 (SAS Institute, Cary, North Carolina, USA). For all analyses, a two-sided p-value<0.05 was considered statistically significant. The methods of patient selection are based upon statistical analysis of data from the clinical trials, and is representative of actual patients having the characteristics described, actually treated with a pharmaceutical composition comprising sodium chlorite or placebo. However, the methods of patient selection and treatment methods were not part of the clinical trials, and are embodiments of the present disclosure.

The phase 2A trial enrolled 138 ALS patients within three years of symptom onset and had three equal arms; placebo, 1 mg/kg and 2 mg/kg NP001 (a pharmaceutical composition comprising sodium chlorite).

The data presented with NP001 sensitivity corresponds with ALS patients that were slowly progressive, had a longer time from ALS symptom onset, and the only subset with evidence of inflammation (high percentage of blood granulocytes). Elevation in CRP after 21 months can signal the presence of a progressive inflammatory process that drives this large ALS disease subset.

The phase 2B trial was conducted from August 2016 through December 2017 at 21 sites in the United States and one in Canada. The study was fully enrolled and did not terminate early. Participants were men and women who were diagnosed with probable or definite ALS according to El Escorial criteria. Participants were required to have an onset of ALS-related weakness within 3 years, SVC>65% of predicted, and a clinically estimated life expectancy of >6 months. All participants were required to have high sensitivity CRP (hs-CRP) levels at screening at least or greater than 1.13 mg/L, the median value noted in the phase 2A trial. Participants receiving riluzole had to be on a stable dose for 30 days. Individuals on continuous positive airway pressure or bilevel positive airway pressure, those with active pulmonary disease, and those who had received recent immunotherapy were excluded.

The study was randomized, double-blind, and placebo-controlled, and study drug was administered over 6 cycles. Participants were allocated in a 1:1 manner to NP001 (a pharmaceutical composition comprising sodium chlorite) 2 mg/kg/day (of chlorite), or placebo, and stratified by ALS site of onset (bulbar/limb). Study drug was infused over 30 minutes by an infusion pump. Participants received a total of 20 infusions over 6 monthly cycles as previously defined. There was one month between the start of each cycle. Cycle 1 consisted of 5-serial daily infusions. Cycles 2, 3, 4, 5, and 6 each consisted of 3 consecutive daily infusions. The randomized population who received at least one dose of a pharmaceutical composition comprising sodium chlorite or placebo and had at least one post-baseline ALSFRS-R total score assessment was pre-defined as the modified intent-to-treat (mITT) population. Investigators, site staff, and ALSFRS-R raters remained blinded to treatment allocation throughout the study. An independent data monitoring committee periodically evaluated safety during the trial.

All randomized participants who received at least one dose of study drug are included in the analysis and summaries of safety data. Tolerability and safety were assessed via adverse event (AE) reports, vital signs, ECGs, laboratory parameters, physical examinations, and formal phlebitis scoring.

Participants were seen for efficacy and safety assessments at monthly intervals. The primary efficacy measure in this study was the mean change from baseline in the ALSFRS-R score following 6 months of treatment. Secondary efficacy measures included the mean percentage change from baseline in predicted SVC following 6 months of treatment, and percentage of participants who did not worsen as assessed by the change from baseline in the ALSFRS-R score following 6 months of treatment (non-progressors).

Statistical analysis was performed using SAS 9.4 and JMP Pro 16 (SAS Institute, Cary, North Carolina, USA). In general, data were summarized using counts and percentages for categorical data and using standard univariate descriptive statistics (number of participants, mean, standard deviation, median) for continuous data. Fisher's exact test was used to compare percentages between placebo and a pharmaceutical composition comprising sodium chlorite with respect to non-progressors. Analysis of covariance models was used to compare placebo to each a pharmaceutical composition comprising sodium chlorite group for continuous data. For all analyses, a two-sided p-value<0.05 was considered statistically significant Duration of ALS at baseline was the months since ALS symptom onset. Average disease progression (DP) at baseline was assessed using the formula:

$$Avg.DP = \frac{(48 - ALSFRS-R-R \text{ score at baseline})}{ALS \text{ duration}}$$

Genetic Testing Information of Familial ALS

| Familial ALS | Placebo (N = 14) | Pharmaceutical composition comprising sodium chlorite 2 mg/kg (N = 2) |
|---|---|---|
| Genetic testing | 8 participants had genetic testing, 4 out of 8 participants had gene mutation (3 with C9ORF72 & 1 with Profilin 9 gene mutation). No genetic mutations were found in the other 4 participants. | 1 participant had genetic testing and confirmed with SOD1 gene mutation. |
| Without genetic testing | 6 participants did not have genetic testing. | 1 participant did not have genetic testing. |

N = Number of participants.

Baseline Demographics of Participants with Plasma CRP at Least or Greater than 1.13 mg/L and Age 40-65 Years at Baseline

| Characteristics | pharmaceutical composition comprising sodium chlorite 2 mg/kg (N = 56) | Placebo (N = 61) | Overall (N = 117) |
|---|---|---|---|
| Sex, N (%) | | | |
| Female | 19 (33.9%) | 17 (27.9%) | 36 (30.8%) |
| Male | 37 (66.1%) | 44 (72.1%) | 81 (69.2%) |
| Age at enrollment in years, mean ± SD | 56.0 ± 6.5 | 54.5 ± 6.0 | 55.2 ± 6.3 |
| Type of ALS [1], N (%) | | | |
| Familial | 1 (1.8%) | 12 (19.7%) | 13 (11.1%) |
| Sporadic | 55 (98.2%) | 49 (80.3%) | 104 (88.9%) |
| Site of ALS onset, N (%) | | | |
| Bulbar | 7 (12.5%) | 12 (19.7%) | 19 (16.2%) |
| Limb | 49 (87.5%) | 49 (80.3%) | 98 (83.8%) |
| El Escorial criteria for ALS, N (%) | | | |
| Definite | 26 (46.4%) | 27 (44.3%) | 53 (45.3%) |
| Probable | 21 (37.5%) | 24 (39.3%) | 45 (38.5%) |
| Probable Laboratory Supported | 3 (5.4%) | 4 (6.6%) | 7 (6.0%) |
| Possible | 6 (10.7%) | 6 (9.8%) | 12 (10.3%) |
| ALSFRS-R score at baseline, mean ± SD | 39.2 ± 4.1 | 37.4 ± 4.8 | 38.3 ± 4.5 |
| Vital capacity at baseline, mean ± SD | 96.1 ± 19.8 | 90.8 ± 17.6 | 93.3 ± 18.8 |
| Months since ALS symptom onset [2], mean ± SD | 20.20 ± 8.41 | 17.60 ± 7.89 | 18.85 ± 8.21 |
| Baseline hs-CRP (mg/L), mean ± SD | 3.94 ± 3.55 | 3.12 ± 2.10 | 3.51 ± 2.90 |
| Baseline hs-CRP of non-progressors [3] (mg/L), mean ± SD | 2.57 ± 2.37 (N = 7) | 5.52 ± 5.04 (N = 19) | 4.73 ± 4.63 (N = 26) |

[1] For familial ALS: 7 out of 12 participants in placebo group had genetic testing, only 4 participants were confirmed with gene mutation, there were no significant differences in clinical outcome. One in a pharmaceutical composition comprising sodium chlorite & 5 in placebo participants did not have genetic testing.
[2] Months from ALS symptom onset to baseline
[3] Non-progressors: Participants showing no decline of ALSFRS-R score over 6 months of trial.
N=Number of participants.
SD=Standard deviation.
ALSFRS-R=ALS Functional Rating Scale-Revised.
hs-CRP=High sensitivity C-Reactive Protein.

Example 1: Treatment of a Subpopulation of ALS Patients with Chlorite (Phase 2A Results)

Treatment of ALS patients with NP001 (a pharmaceutical composition comprising sodium chlorite) begins with identifying the patient as a candidate for such treatment with a pharmaceutical composition comprising sodium chlorite based on patient characteristics that place them within the target ALS patient population likely to be responsive to treatment with a pharmaceutical composition comprising sodium chlorite. In this example, these characteristics includes any patient with ALS.

A Phase 1 controlled trial of NP001 in patients with ALS demonstrated the safety, tolerability and dose dependent down-regulation of monocyte activation. The Phase 2A study assessed the safety, tolerability, and preliminary efficacy of NP001 for slowing progression of ALS. A modest, non-significant trend in slowing of progression was noted, greatest in those patients with elevated systemic inflammation at baseline. Elevated inflammation was defined as having plasma wide-range C-reactive protein (wr-CRP) values greater than 1.13 mg/L in whom the change from baseline on the ALSFRS-R scale was −2.2 points over the 6-month treatment period compared to −5.1 points in the placebo group. Additionally, more than twice as many patients on high dose pharmaceutical composition comprising sodium chlorite (25%) did not progress during six months of treatment compared to placebo (11%). Most "non progressors" had an elevated baseline biomarker of inflammation. Elevated inflammation associated IL-18 and lipopolysaccharide (LPS) levels at baseline, normalized following treatment with 2 mg/kg NP001.

Example 2: Treatment of a Subpopulation of ALS Patients with Chlorite (Phase 2B Results)

Approximately 300 subjects were screened to yield 68 randomized to placebo and 70 to NP001. 117 participants completed planned dosing. FIG. 1 shows the flowchart of individual disposition in the phase 2B trial. It should be noted that one placebo and three NP001 patients discontinued the trial to initiate treatment with edaravone, which had been approved for the treatment of ALS after initiation of the trial. The only significant difference in TEAEs between NP001 and placebos is the higher rate of infusion related side effects in the NP001 group. Infusion related sensations of burning resolved for most patients with a slowing of the infusion rate.

Treatment of ALS patients with NP001 (a pharmaceutical composition comprising sodium chlorite) begins with identifying the patient as a candidate for such treatment with a pharmaceutical composition comprising sodium chlorite based on patient characteristics that place them within the target ALS patient population likely to be responsive to treatment with a pharmaceutical composition comprising sodium chlorite. In this example, these characteristics includes patients with stable disease having elevated C-reactive protein (CRP) levels of at least or greater than 1.13 mg/L, and patient age 40-65.

Patients are treated with NP001 at a dosage of 2 mg/kg chlorite in the active arm for 5 days of drug infused over 60 minutes the first month followed by three days in a row per month for the subsequent 5 months.

Patients are then evaluated for ALS disease progression using the ALS functional rating scale (ALSFRS-R), and by measuring vital capacity (VC), weekly. ALSFRS-R evaluation is conducted using questionnaire-based methodology. VC is measured using a spirometer.

One of the most common adverse events was infusion site pain. It is found that this adverse event could be mitigated by slowing infusion from 30 minutes to 60 minutes.

The primary endpoint in each of the phase 2 trials was change from baseline ALSFRS-R score in participants receiving 2 mg/kg a pharmaceutical composition comprising sodium chlorite or placebo over the six-month studies. The secondary endpoint in each trial was percent change in predicted vital capacity (VC) over the six-months of study, which serves as a predictor of mortality in ALS patients. The phase 2A trial assessed the percent predicted VC change in forced vital capacity (FVC) whereas the phase 2B assessed percent predicted VC change in SVC. Percent predicted VC change from baseline values between FVC and SVC are comparable, therefore the evaluation of a pharmaceutical composition comprising sodium chlorite effects on VC combined changes from both trials normalized to "percent of predicted VC change from baseline [100×(predicted VC at study end−predicted VC at baseline)/predicted VC at baseline]". The plasma concentrations of wr-CRP as exploratory biomarkers were measured for the phase 2A. For the phase 2B, the plasma hs-CRP values were used as one of the entry criteria. To combine two sets of CRP data from the phase 2A and phase 2B for data analysis, the plasma wr-CRP values from the phase 2A were converted to hs-CRP using a simple calibration equation from Ziv-Baran et al to adjust the wr-CRP values (Adjusted wrCRP=0.3136+0.8803×wrCRP). Analyses of baseline disease clinical factors and demographic factors were conducted by treatment group.

Figure 2:
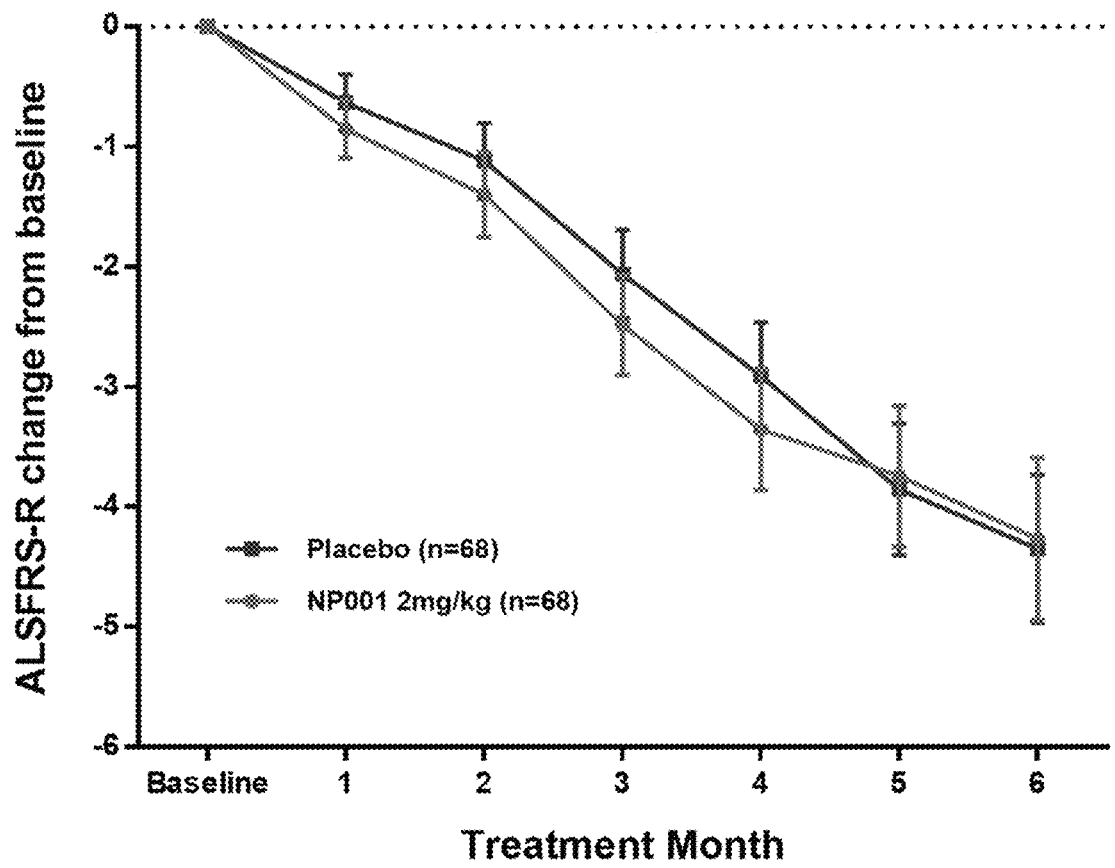
FIG. 2 shows a graph of ALSFRS-R score change from baseline of subjects treated with a pharmaceutical composition comprising sodium chlorite (NP001) as opposed to a placebo.
Figure 3:
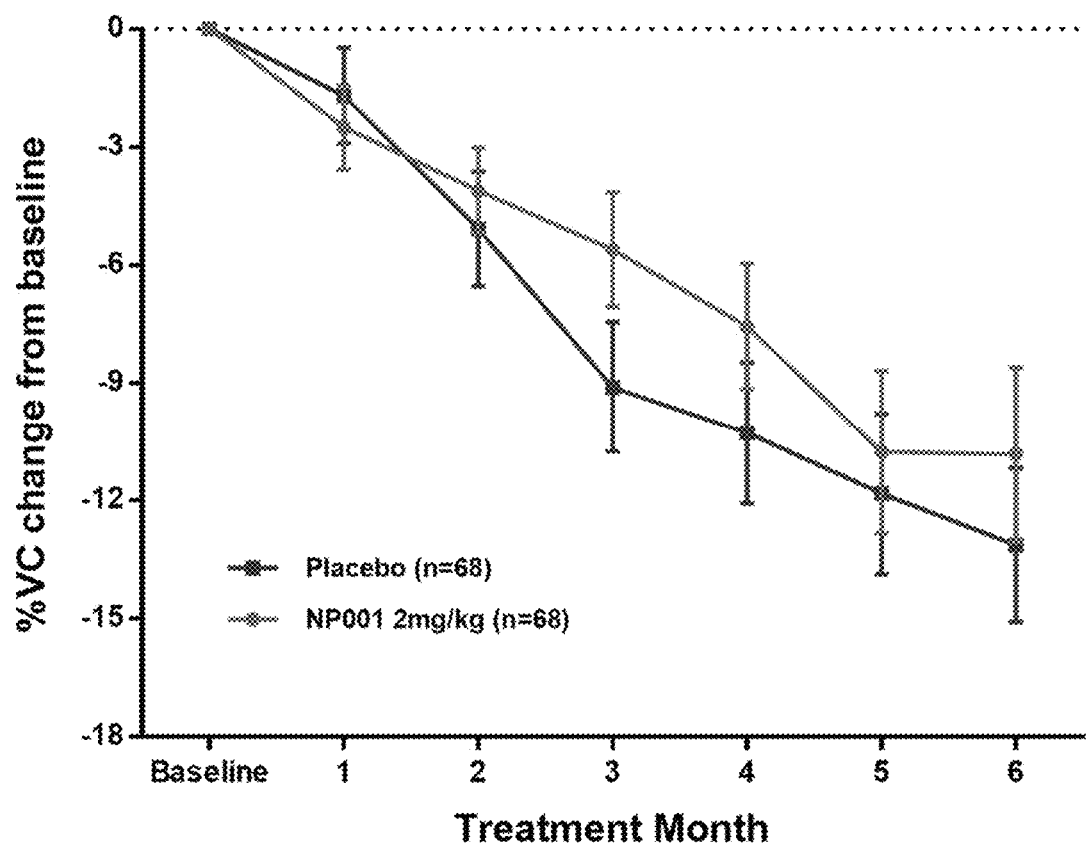
FIG. 3 shows a graph vital capacity change of subjects treated with a pharmaceutical composition comprising sodium chlorite (NP001) as opposed to a placebo.
Figure 5:
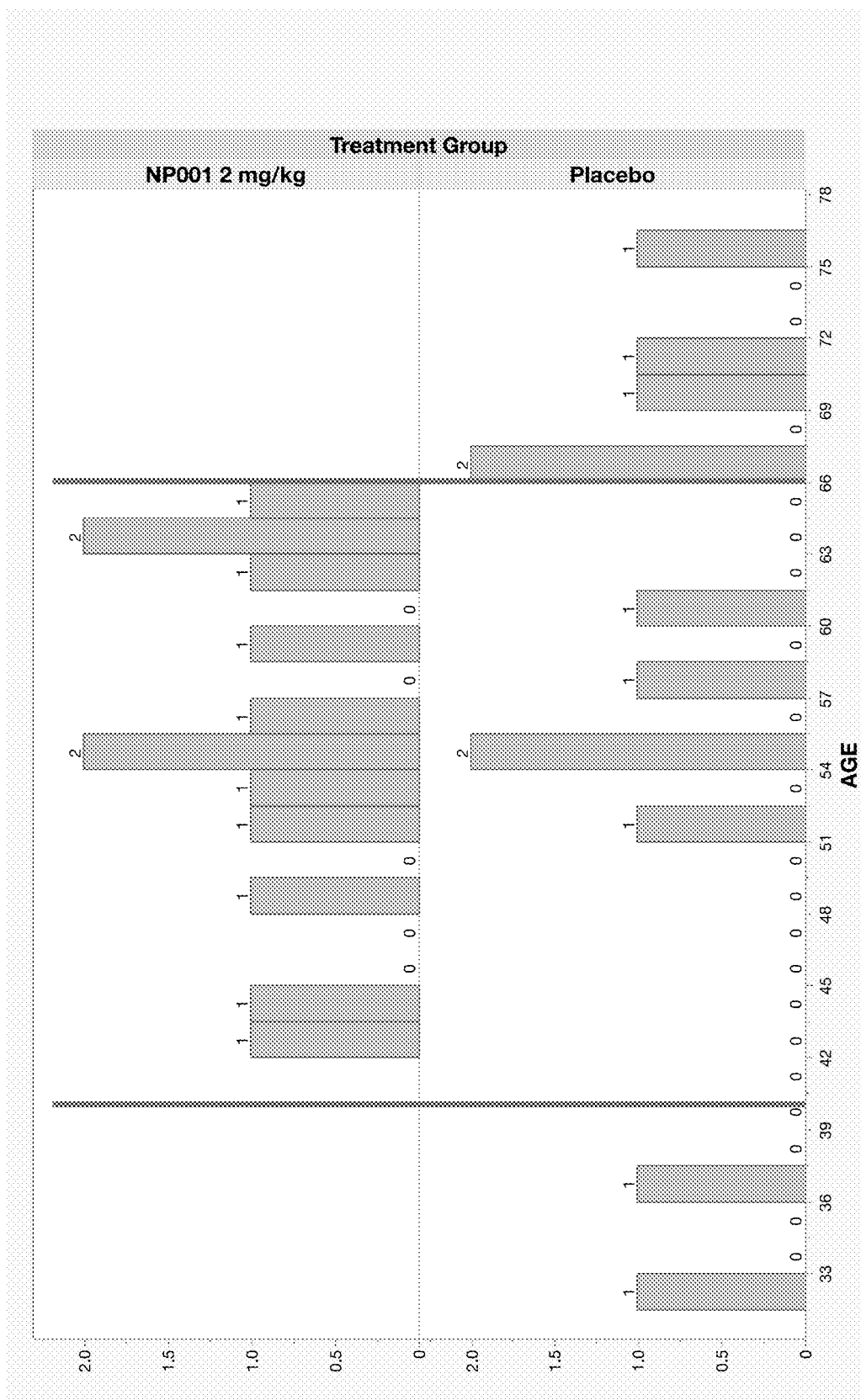
FIG. 5 shows an age distribution chart of subjects who did not progress during the trial.

FIG. 2 shows ALSFRS-R change score change from baseline of all patients in the study. ALSFRS-R score change from baseline for participants treated with a pharmaceutical composition comprising sodium chlorite depicted with circles (n=68) and compared to placebo group depicted with squares (n=68). Bars represent mean of ALSFRS-R score change from baseline±SEM. No differences were seen between a pharmaceutical composition comprising sodium chlorite and placebo groups by the end of study (a pharmaceutical composition comprising sodium chlorite=−4.3 vs. Placebo=−4.3) (Wilcoxon test, p=0.71). FIG. 3 shows a graph vital capacity change of subjects treated with a pharmaceutical composition comprising sodium chlorite as opposed to a placebo. Mean change from baseline in percent predicted SVC for participants treated with a pharmaceutical composition comprising sodium chlorite (n=68) is depicted with circles and compared with the placebo group (n=68) depicted with squares. Bars represent mean of % predicted SVC change from baseline±SEM. There was no significant difference between a pharmaceutical composition comprising sodium chlorite treated patients and placebos by the end of study (a pharmaceutical composition comprising sodium chlorite=−10.8% vs. Placebo=−13.1%) (Wilcoxon test, p=0.15). FIG. 4 shows a bar chart of the non-progression rate of subjects treated with a pharmaceutical composition comprising sodium chlorite as opposed to a placebo. Non-progression rate with non-progressors defined as no decrease in ALSFRS-R score at baseline to 6 months. The proportion of non-progressors (Non-progression rate) in 2 mg/kg a pharmaceutical composition comprising sodium chlorite treatment (13 out of 55) was similar to placebo group (12 out of 62) (Fisher's exact test, p=0.65). FIG. 5 shows an age distribution chart of subjects who did not progress during the trial. Age distribution plot with increasing age (years) of participant on the X-axis and the number of participants in particular age categories on the Y axis. The top panel represents the age distribution of a pharmaceutical composition comprising sodium chlorite treated non-progressors, 13 of a pharmaceutical composition comprising sodium chlorite treated non-progressors in the phase 2B group (all of the phase 2B a pharmaceutical composition comprising sodium chlorite non-progressors) fell into the 40-65-year-old age range (Top panel, n=13), however, only 5 out of 12 placebo non-progressors were in the 40-65-year age range (Bottom panel, n=12) (Fisher's exact test, p=0.002).

There were three efficacy outcome measures defined at the initiation of the phase 2B study that were reported at the end of the study. No significant differences were seen. The change from baseline in a pharmaceutical composition comprising sodium chlorite vs. placebo in both the ALSFRS-R score as well as the % change in predicted vital capacity showed similar rates of decline (FIG. 2 and FIG. 3). The analysis of % non-progressors in those completing the study showed no difference between a pharmaceutical composition comprising sodium chlorite and placebo groups.

No clinically significant differences in reduction between the two groups are noted when evaluated based only upon treatment with a pharmaceutical composition comprising sodium chlorite.

Example 3: Treatment of a Subpopulation of ALS Patients with Chlorite (Post-Hoc Analysis)

Treatment of ALS patients with NP001 (a pharmaceutical composition comprising sodium chlorite) begins with identifying the patient as a candidate for such treatment with a pharmaceutical composition comprising sodium chlorite based on patient characteristics that place them within the target ALS patient population likely to be responsive to treatment with a pharmaceutical composition comprising sodium chlorite. In this example, these characteristics includes patients with stable disease having elevated C-reactive protein (CRP) levels of at least or greater than 1.13 mg/L, and patient age 40-65.

Patients are treated with NP001 (a pharmaceutical composition comprising sodium chlorite) at a dosage of 2 mg/kg chlorite for 5 days of drug infused over 60 minutes the first month followed by three days in a row per month for the subsequent 5 months.

Patients are then evaluated for ALS disease progression using the ALS functional rating scale (ALSFRS-R), and by measuring vital capacity (VC), weekly. ALSFRS-R evaluation is conducted using questionnaire-based methodology. VC is measured using a spirometer.

It is observed that patients undergoing treatment with a pharmaceutical composition comprising sodium chlorite as described in this example experienced slowing of disease progression beginning at initiation, as measured by evaluation of ALSFRS-R change from baseline; slowing of respiratory function decline in a time frame overlapping that of the ALSFRS-R effect on the drug administration effect beginning at 1 month after initiation; supporting an overall conclusion of slowed disease progression in a significant proportion of ALS patients.

Figure 6:
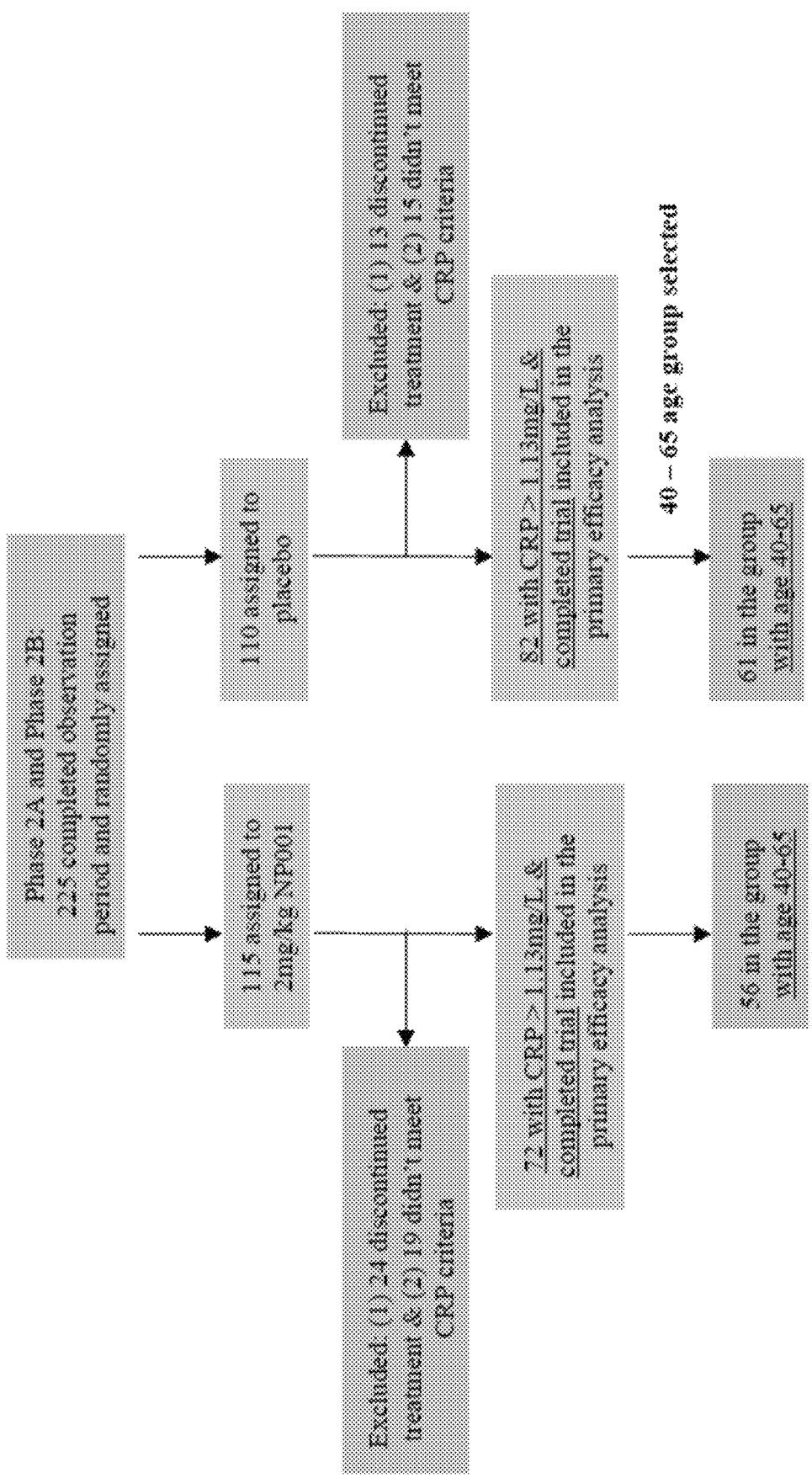
FIG. 6 shows a flow chart summarizing subject distribution with combined participant assignments within the trial.
Figure 7:
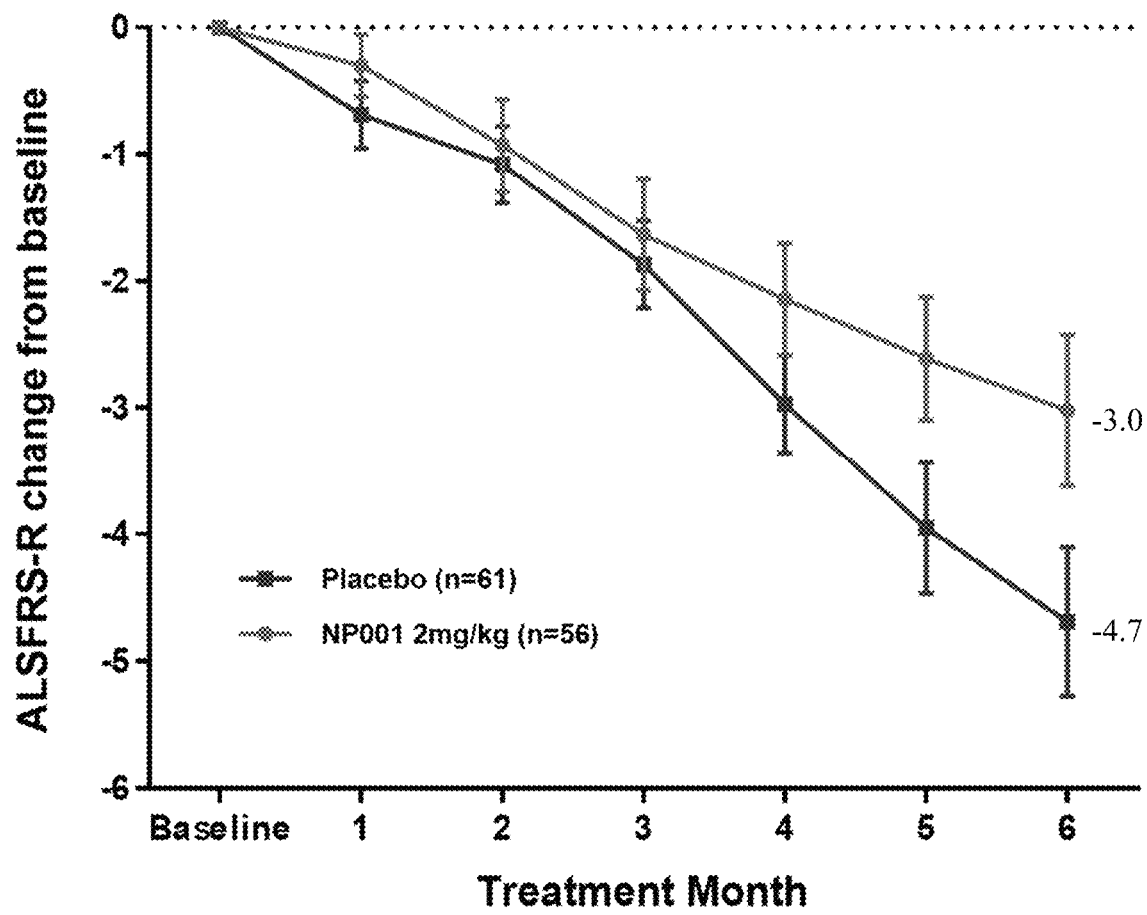
FIG. 7 shows a graph of ALSFRS-R score change from baseline of patients age 40-65 with plasma CRP at least or greater than 1.13 mg/mL treated with a pharmaceutical composition comprising sodium chlorite (NP001) as opposed to a placebo.
Figure 8:
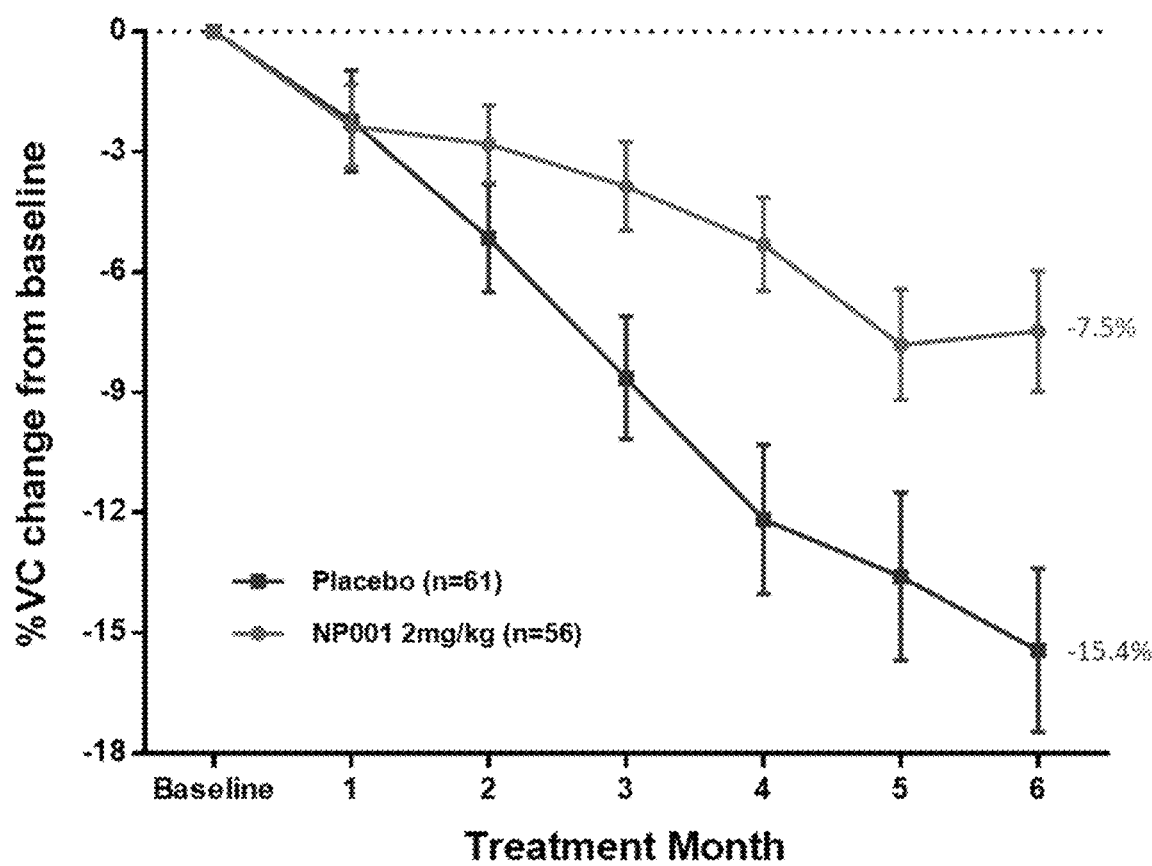
FIG. 8 shows a graph of percent vital capacity change from baseline of patients age 40-65 with plasma CRP at least or greater than 1.13 mg/mL treated with a pharmaceutical composition comprising sodium chlorite (NP001) as opposed to a placebo.
Figure 9:
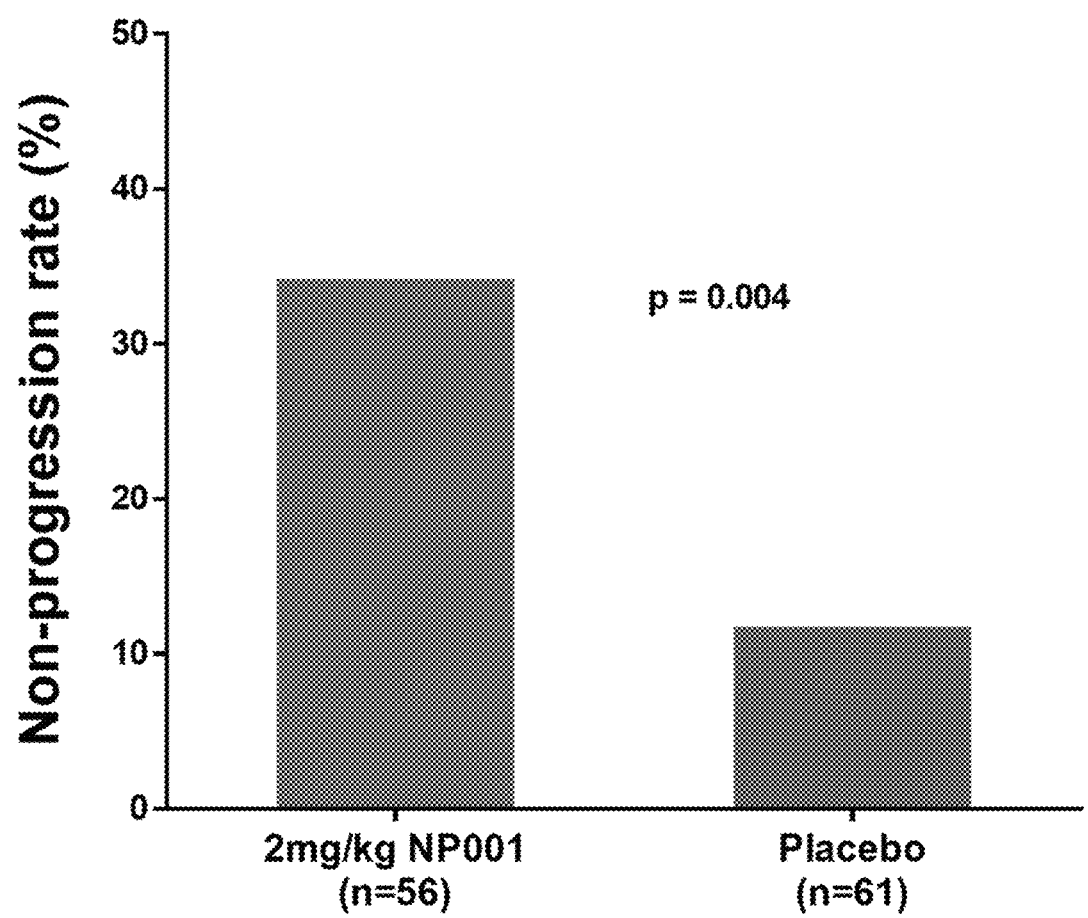
FIG. 9. shows a bar chart of the non-progression rate of subjects age 40-65 with plasma CRP at least or greater than 1.13 mg/mL treated with a pharmaceutical composition comprising sodium chlorite (NP001) as opposed to a placebo.

FIG. 6 shows a flow chart summarizing subject distribution with combined participants assignments within the trial, including the categorization of patients age 40-65 with plasma CRP levels greater than 1.13 mg/L treated with NP001 as opposed to a placebo. FIG. 7 shows a graph of ALSFRS-R score change from baseline of patients age 40-65 with plasma CRP greater than 1.13 mg/mL treated with NP001 as opposed to a placebo. ALSFRS-R score change from baseline for participants treated with NP001 (n=56) depicted with circles and compared to placebo group (n=61) depicted with squares. Bars represent mean of ALSFRS-R score change from baseline±SEM. The NP001 treatment group showed a 36% slower progression rate by the end of study (Wilcoxon test, p=0.01). FIG. 8 shows a graph of percent vital capacity change from baseline of patients age 40-65 with plasma CRP greater than 1.13 mg/mL treated with NP001 as opposed to a placebo. Percent predicted VC change from baseline for participants treated with NP001 (n=56) is depicted with circles and compared with the placebo group (n=61) depicted with squares. Bars represent mean of % predicted VC change from baseline±SEM. Average % VC lost over the 6 months of study: NP001: −7.5% (−1.3% per month); Placebo: −15.4% (−2.6% per month). The NP001 treatment arm lost 51% less respiratory function than the placebo arm by the end of study (Wilcoxon test, p<0.001). FIG. 9. shows a bar chart of the non-progression rate of subjects age 40-65 with plasma CRP greater than 1.13 mg/mL treated with NP001 (a pharmaceutical composition comprising sodium chlorite) as opposed to a placebo. Non-progressors defined as having no decrease in ALSFRS-R score from baseline to 6 months, by treatment group, restricted to those with plasma CRP greater than 1.13 mg/L and age between 40 and 65 years at baseline in phase 2A & 2B trials. The proportion of non-progressors (Non-progression rate) in 2 mg/kg NP001 treatment (19 out of 56) was significantly greater than that of the placebo group (7 out of 61) (Fisher's exact test, p=0.004). In participants with plasma CRP greater than 3 mg/L at baseline, the non-progression rate for a pharmaceutical composition comprising sodium chlorite treated was 46% (13/28) vs. 4.5% (1/22) in the placebo group (Fisher's exact test, p=0.001)

It is observed patients age 40-65 with plasma CRP greater than 1.13 mg/mL treated with NP001 as opposed to a placebo experienced slowed ALS disease progression which corresponds to a reduced decrease in ALSFRS-R score, a reduced loss of vital capacity, and an increased non-progression rate.

Thirteen participants in the Phase 2B NP001 group and 12 in the placebo group did not progress out of a total of 117 participants who completed the study. A demographic analysis of these participants identified a non-random age association with NP001 non-progressors as compared to placebo non-progressors (Fisher's exact, p=0.002). NP001 treated non-progressors were within a 40-65-year-old age range. Placebo non-progressors were arrayed across the range (32-76 years) of ages within the phase 2B study. This non-random age association with NP001 treatment was confirmed with a follow up evaluation of NP001 non-progressors in the phase 2A study were in the 40-65-year age range.

154 participants with baseline plasma hs-CRP of greater than 1.13 mg/L had completed either the phase 2A or 2B trials. The table below shows the baseline demographics and characteristics of the 154 participants included in the post hoc evaluation by treatment group. Based on the initial observations of non-progressor characteristics in the phase 2B, a subset of 40-65-year-old individuals from this combined 154-participant cohort from both pharmaceutical composition comprising sodium chlorite and placebo treated groups were chosen for efficacy evaluations. The selection process for this final group is shown in FIG. 6. Approximately 76% (117) of the 154 participants who completed the trials fell into the 40-65-year-old age group all of whom had plasma CRP greater than 1.13 mg/L. The demographics of this smaller group were similar to the overall phase 2 combined demographics.

Baseline Demographics and Characteristics of Participants in the Phase 2A & 2B Trials Included in Post Hoc Evaluation by Treatment Group.

| Characteristics | NP001 2 mg/kg (N = 72) | Placebo (N = 82) | Overall (N = 154) |
|---|---|---|---|
| Sex, N (%) | | | |
| Female | 24 (33.3%) | 23 (28.0%) | 47 (30.5%) |
| Male | 48 (66.7%) | 59 (72.0%) | 107 (69.5%) |
| Age at enrollment in years, mean ± SD | 56.3 ± 10.6 | 56.0 ± 9.9 | 56.1 ± 10.2 |
| Type of ALS, N (%) | | | |
| Familial | 1 (1.4%) | 15 (18.3%) | 16 (10.4%) |
| Sporadic | 71 (98.6%) | 67 (81.7%) | 138 (89.6%) |
| Site of ALS onset, N (%) | | | |
| Bulbar | 9 (12.5%) | 14 (17.1%) | 23 (14.9%) |
| Limb | 63 (87.5%) | 68 (82.9%) | 131 (85.1%) |
| El Escorial criteria for ALS, N (%) | | | |
| Definite | 32 (44.4%) | 35 (42.7%) | 67 (43.5%) |
| Probable | 29 (40.3%) | 35 (42.7%) | 64 (41.6%) |
| Probable Laboratory Supported | 5 (6.9%) | 6 (7.3%) | 11 (7.1%) |
| Possible | 6 (8.3%) | 6 (7.3%) | 12 (7.8%) |
| ALSFRS-R score at baseline, mean ± SD | 38.4 ± 4.6 | 37.5 ± 5.5 | 37.9 ± 5.1 |
| Vital capacity at baseline, mean ± SD | 93.3 ± 19.4 | 89.9 ± 18.4 | 91.5 ± 18.9 |
| Months since ALS symptom onset [1], mean ± SD | 19.62 ± 8.45 | 18.14 ± 8.12 | 18.83 ± 8.28 |
| hs-CRP at baseline (mg/L), mean ± SD | 4.08 ± 3.46 | 3.97 ± 5.17 | 4.02 ± 4.44 |

[1] Months from ALS symptom onset to baseline

Among the 117 evaluable 40-65-year-old participants, the change in ALSFRS-R score and % predicted VC score change from baseline to study end were calculated by treatment (FIGS. 7 and 8). As compared with the placebo group, the NP001 group showed a slower decline in ALSFRS-R score (36%, FIG. 7) (p=0.01). In addition, NP001-treated patients had a 51% slowing of VC loss compared to placebo (FIG. 8) (p<0.001).

Participants showing no loss of ALSFRS-R score over 6 months (non-progressors from both treated and placebo groups) were significantly more likely to have had NP001 treatment (FIG. 9). 34% (19/56) of a pharmaceutical composition comprising sodium chlorite treated participants were non-progressors compared to 11% (7/61) of placebos over the same time frame (p=0.004). Compared to non-progressors in placebo group, higher levels of baseline CRP were observed in a pharmaceutical composition comprising sodium chlorite-treated non-progressors. In participants with even higher CRP levels, >3 mg/L at baseline, 46% (13/28) of a pharmaceutical composition comprising sodium chlorite treated as compared with 4.5% of placebos (1/22) were non-progressors (Fisher's exact, p=0.001).

In ALS patients, loss of respiratory vital capacity translates directly to poor survival. Similar to the variability seen in ALSFRS-R score comparisons, respiratory function changes in ALS patients are reproducible over time, whether the measures are FVC or SVC. Natural history studies of VC over time in ALS patients confirm an average loss of 2.5-3% of respiratory function per month. In this post hoc analysis, a pharmaceutical composition comprising sodium chlorite slowed respiratory VC loss to 1.3% per month as compared to the placebo group with a loss of 2.6%/month.

Some results of the studies are summarized in the table below:

| | NP001 2 mg/kg (CRP > 1.13 mg/L, n = 75) | | | | | | | | | | |
|---|---|---|---|---|---|---|---|---|---|---|---|
| | Stable (6 F/14 M) | | | | | | Progressors (20 F/35 M) | | | | |
| | N | Mean | Std Dev | Median | Min | Max | N | Mean | Std Dev | Median | Min | Max |
| AGE | 20 | 52.9 | 7.7 | 53.5 | 40 | 65 | 55 | 57.3 | 11.1 | 59.0 | 28 | 78 |
| Baseline ALSFRS-R Score | 20 | 38.6 | 4.4 | 40.0 | 28 | 45 | 55 | 38.1 | 4.8 | 39.0 | 28 | 47 |
| Baseline VC | 20 | 100.6 | 19.3 | 99.0 | 69 | 132 | 55 | 95.0 | 20.3 | 88.0 | 57 | 139 |
| ALS duration (Months) | 20 | 22.89 | 8.02 | 23.80 | 6.97 | 33.17 | 55 | 18.34 | 8.27 | 16.83 | 2.67 | 35.80 |
| Average DP Rate @Baseline | 20 | 0.48 | 0.28 | 0.42 | 0.13 | 1.29 | 55 | 0.67 | 0.50 | 0.61 | 0.03 | 2.58 |
| CRP (mg/L) | 20 | 5.94 | 5.24 | 4.30 | 1.21 | 22.20 | 55 | 3.67 | 2.63 | 2.67 | 1.15 | 10.43 |

Assessment of NP001 activity showed that the percent of non-progressors over the 6 months of study was significantly higher in the NP001 treatment arm than in the placebo arm. In patients with clinically significant levels of plasma CRP (at least or greater than 3 mg/L) there was a 10:1 response advantage for those treated with NP001 as compared to placebo controls. Unlike activity in any other class of drug tested in ALS patients, NP001 (a pharmaceutical composition comprising sodium chlorite) administration was associated with disease stabilization for at least 6 months in a significant subset of patients. Further, consistent with the anti-inflammatory activities of a pharmaceutical composition comprising sodium chlorite, the patients who benefitted from treatment were more likely to be those with higher level of inflammation as defined by blood CRP levels.

A patient without any loss of ALSFRS-R score is categorized as having "stable" disease. Both NP001 treated and placebo groups of patients are scored as to the proportion of patients who had stable disease over the 6-month trials. A pharmaceutical composition comprising sodium chlorite may have dose dependently stabilized symptom progression in a subset of patients.

In patients between the ages of 40 and 65 years old with plasma CRP at least or greater than 1.13 mg/L, NP001 (a pharmaceutical composition comprising sodium chlorite) treatment shows a statistically significant reduction in the loss of critical body function as measured by both changes in ALSFRS-R and respiratory vital capacity scoring.

Example 4: Treatment of a Subpopulation of ALS Patients with Chlorite

Treatment of ALS patients with a pharmaceutical composition comprising sodium chlorite (e.g., NP001) begins with identifying the patient as a candidate for such treatment with a pharmaceutical composition comprising sodium chlorite based on patient characteristics that place them within the target ALS patient population likely to be responsive to treatment with a pharmaceutical composition comprising sodium chlorite. In this example, these characteristics includes patients with stable disease having elevated C-reactive protein (CRP) levels of at least or greater than 1.13 mg/L, patient age 40-65, and wherein the subject has a sporadic ALS pathology.

In this example, sporadic ALS pathology includes where the subject has no familial history of ALS (e.g., does not have an inherited ALS pathology), wherein the subject does not have a mutation in an ALS-associated gene, and wherein the subject does not have a mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3, 4,B4, ALS3, ALS7, ALS6-21, or ALS-FTD.

Patients are treated with a pharmaceutical composition comprising sodium chlorite at a dosage of 2 mg/kg chlorite in the active arm for 5 days of drug infused over 60 minutes the first month followed by three days in a row per month for the subsequent 5 months.

Patients are then evaluated for ALS disease progression using the ALS functional rating scale (ALSFRS-R), and by measuring vital capacity (VC), weekly. ALSFRS-R evaluation is conducted using questionnaire-based methodology. VC is measured using a spirometer.

It is observed that patients undergoing treatment with a pharmaceutical composition comprising sodium chlorite as described in this example experienced slowing of disease progression beginning at initiation, as measured by evaluation of ALSFRS-R change from baseline; slowing of respiratory function decline in a time frame overlapping that of the ALSFRS-R effect on the drug administration effect beginning at 1 month after initiation; supporting an overall conclusion of slowed disease progression in a significant proportion of ALS patients. It is further observed that an increased percentage of patients undergoing treatment with a pharmaceutical composition comprising sodium chlorite as described in this example experience slowed disease progression when compared to the cohort of Example 2 which does not account for subject sporadic ALS pathology.

In patients between the ages of 40 and 65 years old with plasma CRP at least or greater than 1.13 mg/L, and with a sporadic ALS pathology; a pharmaceutical composition comprising sodium chlorite treatment shows a statistically significant reduction in the loss of critical body function as measured by both changes in ALSFRS-R and respiratory vital capacity scoring.

Explanation of Terminology Used in the Present Disclosure

The terminology used herein is for the purpose of describing particular embodiments only and is not intended to be limiting of the disclosure. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Treatment", "treating", "palliating" and "ameliorating", as used herein, are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "effective amount", "therapeutic amount" or "therapeutic effective amount" which is further described herein, encompasses both this lesser effective amount and the usual effective amount, and indeed, any amount that is effective to elicit a particular condition, effect, and/or response. As such, a dose of any such subject of concurrent administration may be less than that which might be used were it administered alone. One or more effect (s) of any such subject (s) of administration may be additive or synergistic. Any such subject(s) of administration may be administered more than one time. The effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or down-regulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

"Subject" refers to an animal, such as a mammal, for example a human. The methods described herein can be useful in both human therapeutics, pre-clinical, and veterinary applications. In some embodiments, the subject is a mammal, and in some embodiments, the subject is human.

The term "in vivo" refers to an event that takes place in a subject's body.

While embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents.

Embodiments

1. A method for treating a subject with chlorite, wherein the subject has amyotrophic lateral sclerosis (ALS), the method comprising: determining if the subject is age 40-65, and if the subject is age 40-65, administering the chlorite to the subject.
2. The method of embodiment 1, wherein if the subject is not age 40-65, not administering the chlorite to the subject.
3. A method of treating amyotrophic lateral sclerosis (ALS) in a subject, the method comprising administering to the subject chlorite, wherein the subject is 45 to 65 years old.
4. The method of any one of embodiments 1-3, wherein the subject has an elevated plasma C-reactive protein (CRP) level.

5. The method of embodiment 4, wherein the elevated plasma CRP level is greater than 3 mg/L CRP in a plasma sample from the subject.
6. The method of any one of embodiments 1-3, wherein prior to administering the chlorite to the subject, the method further comprises: determining whether the subject has an elevated plasma C-reactive protein (CRP) level; wherein the chlorite is administered to the subject if the subject is age 40-65 and has an elevated plasma CRP level.
7. The method of embodiment 6, wherein determining whether the subject has an elevated plasma CRP level comprises performing or having performed an assay on a plasma sample from the subject to determine the level of CRP in the plasma sample.
8. The method of embodiment 6 or embodiment 7, wherein the elevated plasma CRP level is greater than 3 mg/L CRP in the plasma sample from the subject.
9. The method of embodiment 4 or embodiment 8, wherein the subject has an elevated plasma CRP level if the plasma sample has greater than 3.1, 3.2, 3.3, 3.4, 3.5, 3.6, 3.7, 3.8, 3.9, or 4 mg/L CRP.
10. The method of any one of embodiments 4-9, wherein the CRP level is or has been determined by latex agglutination, latex-enhanced nephelometry, photometric measurement of antigen-antibody reaction, or highly sensitive Near Infrared Particle Immunoassay rate methodology.
11. The method of any one of embodiments 1-10, wherein the subject has experienced a symptom of ALS for at least 12 months prior to administering the chlorite to the subject.
12. The method of any one of embodiments 1-10, wherein prior to administering the chlorite to the subject, the method further comprises: determining whether the subject has experienced a symptom of ALS for at least 12 months; wherein the chlorite is administered to the subject if the subject is age 40-65 and has experienced a symptom of ALS for at least 12 months.
13. The method of embodiment 12, wherein determining the length of time the subject has experienced a symptom of ALS comprises reviewing the subject's medical history for symptoms of ALS, reviewing the subject's medical history for a diagnosis of ALS, or inquiring from the subject as to when they first began to experience symptoms of ALS, or a combination thereof.
14. The method of any one of embodiments 11-13, wherein the symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
15. The method of any one of embodiments 11-14, wherein the subject has experienced a symptom of ALS for at least 18 months or at least 21 months prior to administering the chlorite to the subject.
16. A method of treating amyotrophic lateral sclerosis (ALS) in a subject, the method comprising: (a) determining the age of the subject and whether the subject has an elevated level of plasma C-reactive protein (CRP), and (b) if the subject is age 40-65 and has an elevated level of plasma CRP, administering chlorite to the subject.
17. The method of embodiment 16, wherein if the subject is not age 40-65, not administering the chlorite to the subject.
18. The method of embodiment 16 or embodiment 17, wherein if the subject does not have an elevated level of plasma CRP, not administering the chlorite to the subject.
19. A method of treating amyotrophic lateral sclerosis (ALS) in a subject, the method comprising administering to the subject chlorite, wherein the subject is age 40-65 and has an elevated level of CRP.
20. The method of any one of embodiments 16-19, wherein the high level of plasma CRP is greater than 3 mg/L CRP in a plasma sample from the subject.
21. The method of embodiment 20, wherein the high level of plasma CRP is greater than 3.1, 3.2, 3.3, 3.4, 3.5, 3.6, 3.7, 3.8, 3.9, or 4 mg/L CRP in the plasma sample from the subject.
22. The method of any one of embodiments 16-21, wherein the CRP level is or has been determined by latex agglutination, latex-enhanced nephelometry, photometric measurement of antigen-antibody reaction, or highly sensitive Near Infrared Particle Immunoassay rate methodology.
23. The method of any one of embodiments 16-22, wherein the subject has experienced a symptom of ALS for at least 12 months prior to administering the chlorite to the subject.
24. The method of any one of embodiments 16-22, wherein prior to administering the chlorite to the subject, the method further comprises: determining whether the subject has experienced a symptom of ALS for at least 12 months; wherein the chlorite is administered to the subject if the subject is age 40-65, has an elevated level of plasma CRP, and has experienced a symptom of ALS for at least 12 months.
25. The method of embodiment 24, wherein determining the length of time the subject has experienced a symptom of ALS comprises reviewing the subject's medical history for symptoms of ALS, reviewing the subject's medical history for a diagnosis of ALS, or inquiring from the subject as to when they first began to experience symptoms of ALS, or a combination thereof.
26. The method of any one of embodiments 23-25, wherein the symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
27. The method of any one of embodiments 23-26, wherein the subject has experienced a symptom of ALS for at least 18 months or at least 21 months prior to administering the chlorite to the subject.
28. A method of treating amyotrophic lateral sclerosis (ALS) in a subject, the method comprising: (a) determining: the age of the subject, whether the subject has an elevated level of plasma C-reactive protein (CRP), and whether the subject has experienced a symptom of ALS for at least 12 months; and (b) if the subject is age 40-65, has an elevated level of plasma CRP, and has experienced a symptom of ALS for at least 12 months, administering chlorite to the subject.
29. The method of embodiment 28, wherein if the subject is not age 40-65, not administering the chlorite to the subject.
30. The method of embodiment 28 or embodiment 29, wherein if the subject does not have an elevated level of plasma CRP, not administering the chlorite to the subject.

31. The method of any one of embodiments 28-30, wherein if the subject has not experienced a symptom of ALS for at least 12 months, not administering chlorite to the subject.
32. A method of treating amyotrophic lateral sclerosis (ALS) in a subject, the method comprising administering to the subject chlorite, wherein the subject is age 40-65, has an elevated level of CRP, and has experienced a symptom of ALS for at least 12 months.
33. The method of any one of embodiments 28-32, wherein the high level of plasma CRP is greater than 3 mg/L CRP in a plasma sample from the subject.
34. The method of embodiment 33, wherein the high level of plasma CRP is greater than 3.1, 3.2, 3.3, 3.4, 3.5, 3.6, 3.7, 3.8, 3.9, or 4 mg/L CRP in the plasma sample from the subject.
35. The method of any one of embodiments 28-34, wherein the CRP level is or has been determined by latex agglutination, latex-enhanced nephelometry, photometric measurement of antigen-antibody reaction, or highly sensitive Near Infrared Particle Immunoassay rate methodology.
36. The method of any one of embodiments 28-35, wherein determining the length of time the subject has experienced a symptom of ALS comprises reviewing the subject's medical history for symptoms of ALS, reviewing the subject's medical history for a diagnosis of ALS, or inquiring from the subject as to when they first began to experience symptoms of ALS, or a combination thereof.
37. The method of any one of embodiments 28-36, wherein the symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
38. The method of any one of embodiments 28-37, wherein the subject has experienced a symptom of ALS for at least 18 months or at least 21 months prior to administering the chlorite to the subject.
39. A method for treating a subject with chlorite, wherein the subject has amyotrophic lateral sclerosis (ALS), the method comprising:
a) determining whether the subject has an elevated plasma C-reactive protein (CRP) level by: performing or having performed an assay on a plasma sample from the subject to determine if the plasma sample has greater than 3 mg/L CRP, and if the plasma sample has greater than 3 mg/L the subject has an elevated plasma CRP level,
b) determining the length of time the subject has experienced a symptom of ALS, and
c) if the subject has an elevated plasma CRP level and has experienced a symptom of ALS for at least 12 months, then administering chlorite to the subject.
40. The method of embodiment 39, wherein the subject has an elevated plasma CRP level if the plasma sample has greater than 3.1, 3.2, 3.3, 3.4, 3.5, 3.6, 3.7, 3.8, 3.9, or 4 mg/L CRP.
41. The method of embodiment 39 or embodiment 40, wherein determining if the plasma sample has greater than 3 mg/mL CRP comprises latex agglutination, latex-enhanced nephelometry, photometric measurement of antigen-antibody reaction, or highly sensitive Near Infrared Particle Immunoassay rate methodology.
42. The method of any one of embodiments 39-41, wherein the subject has experienced a symptom of ALS for at least 18 months or at least 21 months prior to administering chlorite to the subject.
43. The method of any one of embodiments 39-42, wherein determining the length of time the subject has experienced a symptom of ALS comprises reviewing the subject's medical history for symptoms of ALS, reviewing the subject's medical history for a diagnosis of ALS, or inquiring from the subject as to when they first began to experience symptoms of ALS.
44. The method of any one of embodiments 39-43, wherein a symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
45. The method of any one of embodiments 39-44 further comprising determining if the patient is age 40-65, and if the patient is age 40-65 administering chlorite to the subject.
46. A method of treating amyotrophic lateral sclerosis (ALS) in a subject, the method comprising administering to the subject chlorite, wherein the subject:
i) has an elevated plasma C-reactive protein (CRP) level as indicated by a plasma sample from the subject having greater than 3 mg/L CRP, and
ii) has experienced a symptom of ALS for at least 12 months prior to administration of the chlorite.
47. The method of embodiment 46, wherein the subject has an elevated plasma CRP level if the plasma sample has greater than 3.1, 3.2, 3.3, 3.4, 3.5, 3.6, 3.7, 3.8, 3.9, or 4 mg/L CRP.
48. The method of embodiment 46 or embodiment 47, wherein the subject has been determined to have an elevated plasma CRP level in a method comprising latex agglutination, latex-enhanced nephelometry, photometric measurement of antigen-antibody reaction, or highly sensitive Near Infrared Particle Immunoassay rate methodology.
49. The method of any one of embodiments 46-48, wherein the subject has experienced a symptom of ALS for at least 18 months or at least 21 months prior to administering chlorite to the subject.
50. The method of any one of embodiments 46-49, wherein a symptom of ALS comprises muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
51. A method for treating a subject with chlorite, wherein the subject has amyotrophic lateral sclerosis (ALS), the method comprising:
a) determining whether the subject has an elevated plasma C-reactive protein (CRP) level by: performing or having performed an assay on a plasma sample from the subject to determine if the plasma sample has greater than 3 mg/L CRP, and if the plasma sample has greater than 3 mg/L the subject has an elevated plasma CRP level, and
b) if the subject has an elevated plasma CRP level, then administering chlorite to the subject.

52. The method of embodiment 51, wherein the subject has an elevated plasma CRP level if the plasma sample has greater than 3.1, 3.2, 3.3, 3.4, 3.5, 3.6, 3.7, 3.8, 3.9, or 4 mg/L CRP.
53. The method of embodiment 51 or embodiment 52, wherein determining if the plasma sample has greater than 3 mg/mL CRP comprises latex agglutination, latex-enhanced nephelometry, photometric measurement of antigen-antibody reaction, or highly sensitive Near Infrared Particle Immunoassay rate methodology.
54. The method of any one of embodiments 51-53, wherein prior to step (b) the subject has experienced a symptom of ALS for at least 12 months, at least 18 months or at least 21 months.
55. The method of embodiment 54, wherein a symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
56. The method of any one of embodiments 46-55 further comprising determining if the patient is age 40-65, and if the patient is age 40-65, administering chlorite to the subject.
57. A method for treating a subject with chlorite, wherein the subject has amyotrophic lateral sclerosis (ALS), the method comprising:
a) determining the length of time the subject has experienced a symptom of ALS, and
b) if the subject has experienced a symptom of ALS for at least 12 months, then administering chlorite to the subject.
58. The method of embodiment 57, wherein the subject has experienced a symptom of ALS for at least 18 or at least 21 months prior to administering chlorite to the subject.
59. The method of embodiment 57 or embodiment 58, wherein determining the length of time the subject has experienced a symptom of ALS comprises reviewing the subject's medical history for symptoms of ALS, reviewing the subject's medical history for a diagnosis of ALS, or inquiring from the subject as to when they first began to experience symptoms of ALS.
60. The method of any one of embodiments 57-59, wherein a symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
61. The method of any one of embodiments 57-60, wherein a sample of plasma from the subject has greater than 3 mg/L CRP.
62. The method of embodiment 61, wherein a sample of plasma from the subject has greater than 3.1, 3.2, 3.3, 3.4, 3.5, 3.6, 3.7, 3.8, 3.9, or 4 mg/L CRP.
63. The method of embodiment 61 or embodiment 62, wherein the level of CRP in the sample of plasma from the subject is or has been determined by a method comprising latex agglutination, latex-enhanced nephelometry, photometric measurement of antigen-antibody reaction, or highly sensitive Near Infrared Particle Immunoassay rate methodology.
64. A method of treating amyotrophic lateral sclerosis (ALS) in a subject, the method comprising administering to the subject chlorite, wherein the subject has an elevated plasma C-reactive protein (CRP) level as indicated by a plasma sample from the subject having greater than 3 mg/L CRP.
65. The method of embodiment 64, wherein the subject has an elevated plasma CRP level if the plasma sample has greater than 3.9 mg/L CRP.
66. The method of embodiment 64 or embodiment 65, wherein the subject has been determined to have an elevated plasma CRP level in a method comprising latex agglutination, latex-enhanced nephelometry, photometric measurement of antigen-antibody reaction, or highly sensitive Near Infrared Particle Immunoassay rate methodology.
67. The method of any one of embodiments 64-66, wherein the subject has experienced a symptom of ALS for at least 12 months, at least 18 months or at least 21 months prior to administration of the chlorite.
68. The method of embodiment 67, wherein a symptom of ALS comprises muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
69. The method of any one of embodiments 57-68 further comprising determining if the patient is age 40-65, and if the patient is age 40-65, administering chlorite to the subject.
70. A method of treating amyotrophic lateral sclerosis (ALS) in a subject, the method comprising administering to the subject chlorite, wherein the subject has experienced a symptom of ALS for at least 12 months prior to administration of the chlorite.
71. The method of embodiment 70, wherein the subject has experienced a symptom of ALS for at least 18 months or at least 21 months prior to administering chlorite to the subject.
72. The method of embodiment 70 or embodiment 71, wherein determining the length of time the subject has experienced a symptom of ALS comprises reviewing the subject's medical history for symptoms of ALS, reviewing the subject's medical history for a diagnosis of ALS, or inquiring from the subject as to when they first began to experience symptoms of ALS.
73. The method of any one of embodiments 70-72, wherein a symptom of ALS comprises muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.
74. The method of any one of embodiments 70-73, wherein a sample of plasma from the subject has greater than 3 mg/L CRP.
75. The method of embodiment 74, wherein a sample of plasma from the subject has greater than 3.1, 3.2, 3.3, 3.4, 3.5, 3.6, 3.7, 3.8, 3.9, or 4 mg/L CRP.
76. The method of embodiment 74 or embodiment 75, wherein the level of CRP in the sample of plasma from the subject is or has been determined by a method comprising latex agglutination, latex-enhanced nephelometry, photometric measurement of antigen-antibody reaction, or highly sensitive Near Infrared Particle Immunoassay rate methodology.

77. The method of any one of embodiments 70-76, further comprising determining if the patient is age 40-65, and if the patient is age 40-65 administering chlorite to the subject.

78. The method of any one of embodiments 1-77, wherein treating comprises reducing a symptom of ALS, reducing progression of ALS, or increasing life expectancy in the subject, or a combination thereof.

79. The method of any one of embodiments 1-78, wherein treating comprises no disease progression in the subject after administration using the ALS functional rating scale (ALSFRS-R).

80. The method of any one of embodiments 1-79, wherein treating comprises not more than a decrease of 3 points in the ALSFRS-R score.

81. The method of any one of embodiments 1-80, wherein treating comprises change in pulmonary function as measured by slow vital capacity readings.

82. The method of any one of embodiments 1-81 wherein treating comprises a longer time to tracheotomy as compared to a subject that has not been treated with chlorite.

83. The method of any one of embodiments 1-82, wherein treating comprises a reduced level of blood inflammatory biomarkers.

84. The method of any one of embodiments 1-83, wherein the subject has displayed one or more symptoms of ALS as based on Electromyogram (EMG), nerve conduction, magnetic resonance imaging (MRI), spinal fluid analysis, or muscle biopsy, or a combination thereof.

85. The method of any one of embodiments 1-84, wherein the subject is or has been diagnosed with ALS.

86. The method of embodiment 85, wherein the subject has been diagnosed with ALS based on Electromyogram (EMG), nerve conduction, magnetic resonance imaging (MRI), spinal fluid analysis, or muscle biopsy, or a combination thereof.

87. The method of embodiment 85 or embodiment 86, wherein the subject is or has been diagnosed with ALS at least 12 months prior to administration of the chlorite.

88. The method of any one of embodiments 1-87, wherein the chlorite comprises sodium chlorite.

89. The method of any one of embodiments 1-87, wherein the chlorite comprises potassium chlorite.

90. The method of any one of embodiments 1-89, wherein the chlorite is administered at 2 mg/kg body weight per dose.

91. The method of any one of embodiments 1-90, wherein the chlorite is administered intravenously.

92. The methods of any of embodiments 1-91, wherein treating further comprises halting loss of subject vital capacity.

93. The method of embodiment 92, wherein halting loss of subject vital capacity comprises a loss of subject vital capacity of not more than 0.05%, 0.075%, 0.1%, 0.125%, 0.15%, 0.2%, 0.225%, 0.25%, 0.275%, 0.3%, 0.5%, 0.75%, 1%, 1.25%, 1.5%, 1.75%, 2%, 3%, 4%, 5%, 6%, 7%, 8%, 9%, 10%, 12.5%, 15%, 17.5%, 20%, 22.5%, or 25% over a six month period.

94. A method of treating amyotrophic lateral sclerosis (ALS) in a subject, the method comprising:
determining the subject to have an elevated plasma C-reactive protein (CRP) level of greater than 1.13 mg/L prior to administering NP001 chlorite;
determining the age of the subject to be age 40-65 prior to administering NP001 chlorite;
administering to the subject NP001 chlorite intravenously over 60 minutes at 2 mg/kg body weight per dose for 5 days for one month;
administering to the subject NP001 chlorite intravenously over 60 minutes at 2 mg/kg body weight per dose for 3 days in a row per month for the subsequent 5 months,
wherein the NP001 chlorite is at least 95% pure, and
wherein the NP001 chlorite is pH balanced to a pH of 7.4.

95. The method of embodiment 1 further comprising determining the subject to have an elevated plasma C-reactive protein (CRP) level of greater than 3.00 mg/L.

96. Chlorite for use in treating amyotrophic lateral sclerosis (ALS) in a subject, wherein the subject has one or more of characteristics (i) to (iii):
(i) the subject is 45 to 65 years old; and/or
(ii) the subject has an elevated plasma level of CRP; and/or
(iii) the subject has experienced a symptom of ALS for at least 12 months prior to the use of chlorite in their treatment.

97. Chlorite for use according to embodiment 96, wherein characteristic (ii) is a plasma level of greater than 1.13 mg/L CRP.

98. Chlorite for use according to embodiment 96, wherein characteristic (ii) is a plasma level of greater than 3 mg/L CRP.

99. Chlorite for use according to embodiment 98, wherein characteristic (ii) is a plasma level of greater than 3.1, 3.2, 3.3, 3.4, 3.5, 3.6, 3.7, 3.8, 3.9, or 4 mg/L CRP.

100. Chlorite for use according to embodiments 96-99, wherein the subject has characteristics (i) and (ii).

101. Chlorite for use according to embodiments 96-100, wherein the subject has characteristics (i), (ii) and (iii).

102. Chlorite for use according to embodiments 96-101, wherein the subject has characteristics (ii) and (iii), and wherein the elevated plasma level of CRP is greater than 1.13 mg/L.

103. Chlorite for use according to embodiments 96-102, wherein the subject has characteristics (ii) and (iii), and wherein the elevated plasma level of CRP is greater than 3 mg/L.

104. Chlorite for use according to embodiments 96-103, wherein plasma levels of CRP is or has been determined by latex agglutination, latex-enhanced nephelometry, photometric measurement of antigen-antibody reaction, or highly sensitive Near Infrared Particle Immunoassay rate methodology.

105. Chlorite for use according to embodiments 96-104, wherein the length of time the subject has experienced a symptom of ALS in characteristic (iii) is at least 18 months or at least 21 months prior to the use of chlorite in their treatment.

106. Chlorite for use according to embodiments 96-105, wherein the length of time the subject has experienced a symptom of ALS is or has been determined by reviewing the subject's medical history for symptoms of ALS, reviewing the subject's medical history for a diagnosis of ALS, or inquiring from the subject as to when they first began to experience symptoms of ALS, or a combination thereof.

107. Chlorite for use according to embodiments 96-106, wherein the symptom of ALS in characteristic (iii) comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.

108. Chlorite for use according to embodiments 96-107, wherein treating achieves one or more of: (a) reducing a symptom of ALS, reducing progression of ALS, or increasing life expectancy in the subject, or a combination thereof; (b) the subject has no disease progression after administration using the ALS functional rating scale (ALSFRS R); (c) the subject has not more than a decrease of 3 points in the ALSFRS R score; (d) the subject achieves change in pulmonary function as measured by slow vital capacity readings; (e) a longer time to tracheotomy as compared to a subject that has not been treated with chlorite; (f) a reduced level of blood inflammatory biomarkers; and/or (g) halting loss of subject vital capacity; and/or (h) the subject has a loss of vital capacity of not more than 0.05%, 0.075%, 0.1%, 0.125%, 0.15%, 0.2%, 0.225%, 0.25%, 0.275%, 0.3%, 0.5%, 0.75%, 1%, 1.25%, 1.5%, 1.75%, 2%, 3%, 4%, 5%, 6%, 7%, 8%, 9%, 10%, 12.5%, 15%, 17.5%, 20%, 22.5%, or 25% over a six month period.

109. Chlorite for use according to embodiments 96-108, wherein the subject has displayed one or more symptoms of ALS as based on electromyogram, nerve conduction, magnetic resonance imaging, spinal fluid analysis, or muscle biopsy, or a combination thereof.

110. Chlorite for use according to embodiment 109, wherein the subject has been diagnosed with ALS based on electromyogram, nerve conduction, magnetic resonance imaging, spinal fluid analysis, or muscle biopsy, or a combination thereof.

111. Chlorite for use according to embodiments 96-110, wherein the subject is or has been diagnosed with ALS at least 12 months prior to the use of chlorite in their treatment.

112. Chlorite for use according to embodiments 96-111, wherein the chlorite comprises sodium chlorite or potassium chlorite.

113. Chlorite for use according to embodiments 96-112, wherein the chlorite is administered at 2 mg/kg body weight per dose.

114. Chlorite for use according to embodiments 96-113, wherein the chlorite is administered intravenously.

115. Chlorite for use according to embodiments 96-114, wherein the chlorite is administered to the subject intravenously over 60 minutes at 2 mg/kg body weight per dose for (a) 5 days for one month then (b) 3 days in a row per month for the subsequent 5 months, wherein the chlorite is at least 95% pure, and wherein the chlorite is pH balanced to a pH of 7.4.

116. The use of chlorite in the manufacture of a medicament for treating ALS, wherein the medicament is for use as defined in embodiments 96-115.

117. A sodium chlorite composition for use in treating amyotrophic lateral sclerosis (ALS) in a subject characterized in that the sodium chlorite composition is administered intravenously over a 60-minute period to the subject, wherein the sodium chlorite composition comprises purified sodium chlorite, wherein the sodium chlorite composition is administered at 2 mg chlorite per kg of the subject's body weight, wherein the sodium chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the sodium chlorite composition comprises dibasic sodium phosphate and has a pH between 7.5 and 9.5.

118. The sodium chlorite composition according to embodiment 117, wherein (i) the progression of the subject's ALS is slowed, (ii) loss of the subject's function is slowed, or (iii) loss of the subject's vital capacity is slowed.

119. The sodium chlorite composition according to embodiment 117, wherein the subject is 40 to 65 years old.

120. The sodium chlorite composition according to embodiment 117, wherein the subject has a plasma C-reactive protein (CRP) level of greater than 1.13 mg/L.

121. The sodium chlorite composition according to embodiment 117, wherein the subject has a plasma hs-CPR level of greater than 1.13 mg/L, or optionally wherein the subject has a plasma hs-CPR level of greater than 3.0 mg/L.

122. The sodium chlorite composition according to embodiment 117, wherein the subject has experienced a symptom of ALS for at least 18 months prior to administering the sodium chlorite composition to the subject, optionally wherein a symptom of ALS comprises: muscle weakness, muscle cramping, muscle twitching, muscle spasms, difficultly in maintaining body posture, difficultly chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.

123. The sodium chlorite composition according to embodiment 117, wherein the subject has a sporadic ALS pathology, 124. The sodium chlorite composition according to embodiment 117, wherein the subject does not have an inherited ALS pathology.

125. The sodium chlorite composition according to embodiment 124, wherein the subject does not have a mutation in an ALS-associated gene, and optionally wherein the subject does not have a mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD.

126. A sodium chlorite composition for use in treating amyotrophic lateral sclerosis (ALS) in a subject with a plasma C-reactive protein (CRP) level of greater than 1.13 mg/L characterized in that the sodium chlorite composition is administered intravenously over a 60-minute period to the subject, wherein the sodium chlorite composition comprises purified sodium chlorite, wherein the sodium chlorite composition is administered at 2 mg chlorite per kg of the subject's body weight, wherein the sodium chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the sodium chlorite composition comprises dibasic sodium phosphate and has a pH between 7.5 and 9.5.

127. A sodium chlorite composition for use in treating amyotrophic lateral sclerosis (ALS) in a subject with a plasma hs-CRP level of greater than 1.13 mg/L characterized in that the sodium chlorite composition is administered intravenously over a 60-minute period to the subject, wherein the sodium chlorite composition comprises purified sodium chlorite, wherein the sodium chlorite composition is administered at 2 mg chlorite per kg of the subject's body weight, wherein the sodium chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the sodium chlorite composition comprises dibasic sodium phosphate and has a pH between 7.5 and 9.5.

128. The sodium chlorite composition according to any one of embodiments 126 or 127, wherein the subject is 40 to 65 years old.

129. A sodium chlorite composition for use in treating amyotrophic lateral sclerosis (ALS) in a subject aged 40 to 65 years characterized in that the sodium chlorite composition is administered intravenously over a 60-minute period to the subject, wherein the sodium chlorite composition comprises purified sodium chlorite, wherein the sodium chlorite composition is administered at 2 mg chlorite per kg of the subject's body weight, wherein the sodium chlorite composition is initially administered daily for 5 days in a row in the first month, and daily for 3 days in a row in subsequent months, wherein the purified sodium chlorite is at least 97% pure, wherein the purified sodium chlorite comprises no more than 2.0% sodium chloride, wherein the purified sodium chlorite comprises no more than 1.0% sodium chlorate, and wherein the sodium chlorite composition comprises dibasic sodium phosphate and has a pH between 7.5 and 9.5.

130. The sodium chlorite composition according to embodiment 129, wherein the subject has a plasma hs-CRP level of greater than 1.13 mg/L.

131. A sodium chlorite composition for use in treating amyotrophic lateral sclerosis (ALS) in a subject characterized in that the sodium chlorite composition is administered intravenously over a 60-minute period to the subject, wherein the sodium chlorite composition is administered at 2 mg chlorite per kg of the subject's body weight; wherein the sodium chlorite composition is initially administered daily for 5 days in a row in the first month, and daily for 3 days in a row in subsequent months; wherein the purified sodium chlorite is at least 97% pure; wherein the purified sodium chlorite comprises no more than 2.0% sodium chloride; wherein the purified sodium chlorite comprises no more than 1.0% sodium chlorate; wherein the sodium chlorite composition comprises dibasic sodium phosphate and has a pH between 7.5 and 9.5; and wherein the subject has at least one ALS response factor selected from:
(a) age 40 to 65 years;
(b) plasma hs-CRP level of greater than 1.13 mg/L;
(c) experienced a symptom of ALS for at least 18 months prior to administration of the sodium chlorite composition
(d) no inherited ALS pathology;
(e) no mutation in an ALS-associated gene; and
(f) no mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD.

132. A method of treating amyotrophic lateral sclerosis (ALS) in a subject aged 40 to 65 years, the method comprising:
administering intravenously to the subject a chlorite composition comprising purified sodium chlorite;
wherein the chlorite composition is administered at 2 mg chlorite per kg of the subject's body weight;
wherein the chlorite composition is initially administered daily for 5 days in a row in the first month, and daily for 3 days in a row in subsequent months;
wherein the purified sodium chlorite is at least 97% pure;
wherein the purified sodium chlorite comprises no more than 2.0% sodium chloride;
wherein the purified sodium chlorite comprises no more than 1.0% sodium chlorate; and
wherein the chlorite composition comprises dibasic sodium phosphate and has a pH between 7.5 and 9.5.

133. The method of embodiment 132, wherein the progression of the subject's ALS is slowed.

134. The method of any one of embodiments 132-133, wherein loss of the subject's function is slowed.

135. The method of any one of embodiments 132-134, wherein loss of the subject's vital capacity is slowed.

136. The method of any one of embodiments 132-135, wherein the chlorite composition is administered over a 60-minute period.

137. The method of any one of embodiments 132-136, wherein the subject has a plasma C-reactive protein (CRP) level of greater than 1.13 mg/L.

138. The method of any one of embodiments 132-137, wherein the subject has a plasma hs-CPR level of greater than 1.13 mg/L.

139. The method of any one of embodiments 132-138, wherein the subject has a plasma hs-CPR level of greater than 3.0 mg/L.

140. The method of any one of embodiments 132-139, wherein the subject has experienced a symptom of ALS for at least 18 months prior to administering the chlorite composition to the subject.

141. The method of embodiment 140, wherein a symptom of ALS comprises: muscle weakness, muscle cramping, muscle twitching, muscle spasms, difficultly in maintaining body posture, difficulty chewing, slow or slurred speech, difficulty swallowing, increased salivation, loss of fine motor skills, difficultly climbing stairs, difficulty breathing, shortness of breath, loss of coordination, pain, fatigue, difficultly walking, increased clumsiness, or a combination of two or more thereof.

142. The method of any one of embodiments 132-141, wherein the subject has a sporadic ALS pathology.

143. The method of any one of embodiments 132-142, wherein the subject does not have an inherited ALS pathology.

144. The method of any one of embodiments 132-143, wherein the subject does not have a mutation in an ALS-associated gene.

145. The method of any one of embodiments 132-144, wherein the subject does not have a mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD.

146. A method of treating amyotrophic lateral sclerosis (ALS) in a subject with a plasma C-reactive protein (CRP) level of greater than 1.13 mg/L, the method comprising:
administering intravenously to the subject a chlorite composition comprising purified sodium chlorite;
wherein the chlorite composition is administered at 2 mg chlorite per kg of the subject's body weight;
wherein the chlorite composition is initially administered for 5 days in a row in the first month, and for 3 days in a row in subsequent months;
wherein the purified sodium chlorite is at least 97% pure;
wherein the purified sodium chlorite comprises no more than 2.0% sodium chloride;
wherein the purified sodium chlorite comprises no more than 1.0% sodium chlorate; and
wherein the chlorite composition comprises dibasic sodium phosphate and has a pH between 7.5 and 9.5.

147. A method of treating amyotrophic lateral sclerosis (ALS) in a subject with a plasma hs-CRP level of greater than 1.13 mg/L, the method comprising:
administering intravenously to the subject a chlorite composition comprising purified sodium chlorite;
wherein the chlorite composition is administered at 2 mg chlorite per kg of the subject's body weight;
wherein the chlorite composition is initially administered for 5 days in a row in the first month, and for 3 days in a row in subsequent months;
wherein the purified sodium chlorite is at least 97% pure;
wherein the purified sodium chlorite comprises no more than 2.0% sodium chloride;
wherein the purified sodium chlorite comprises no more than 1.0% sodium chlorate; and 148. The method of any one of embodiments 146-147, wherein the subject is 40 to 65 years old.

149. The method of any one of embodiments 146-148, wherein the chlorite composition is administered over a 60-minute period.

150. A method of treating amyotrophic lateral sclerosis (ALS) in a subject, the method comprising:
administering intravenously over a 60-minute period to the subject a chlorite composition comprising purified sodium chlorite;
wherein the chlorite composition is administered at 2 mg chlorite per kg of the subject's body weight;
wherein the chlorite composition is initially administered for 5 days in a row in the first month, and for 3 days in a row in subsequent months;
wherein the purified sodium chlorite is at least 97% pure;
wherein the purified sodium chlorite comprises no more than 2.0% sodium chloride;
wherein the purified sodium chlorite comprises no more than 1.0% sodium chlorate; and
wherein the chlorite composition comprises dibasic sodium phosphate and has a pH between 7.5 and 9.5.

151. The method of embodiment 150, wherein the subject has a plasma hs-CRP level of greater than 1.13 mg/L.

152. The method of any one of embodiments 150-151, wherein the subject is 40 to 65 years old.

153. A method of treating amyotrophic lateral sclerosis (ALS) in a subject, the method comprising:
administering intravenously to the subject a chlorite composition comprising purified sodium chlorite;
wherein the chlorite composition is administered at 2 mg chlorite per kg of the subject's body weight;
wherein the chlorite composition is initially administered daily for 5 days in a row in the first month, and daily for 3 days in a row in subsequent months;
wherein the purified sodium chlorite is at least 97% pure;
wherein the purified sodium chlorite comprises no more than 2.0% sodium chloride;
wherein the purified sodium chlorite comprises no more than 1.0% sodium chlorate;
wherein the chlorite composition comprises dibasic sodium phosphate and has a pH between 7.5 and 9.5; and
wherein the subject has at least one ALS response factor selected from:
(a) age 40 to 65 years;
(b) plasma hs-CRP level of greater than 1.13 mg/L;
(c) experienced a symptom of ALS for at least 18 months prior to administration of the chlorite composition.
(d) no inherited ALS pathology;
(e) no mutation in an ALS-associated gene; and
(f) no mutation in SOD1, ALS2, Chromosome 18, SEXT, SPG11, FUS, Chromosome 20, VAPB, ANG, TARDBP/TDP-43, FIG4, OPTN, ATXN2, VCP, UBQLN2, SIGMAR1, CHMP2B, PFN1, ERBB4, HNRNPA1, MATR3, TUBA4A, ANXA11, NEK1, C9orf72, CHCHD10, SQSTM1, TARDBP, SETX, TAF15, EWSR1, hnRNPA2B1, ELP3, TBK1, DCTN1, NEFH, PRPH, C19ORF12, SS18L1, PNPLA6, PON1-3, DAO, CHRNA3,4,B4, ALS3, ALS7, ALS6-21, or ALS-FTD.

What is claimed is:

1. A method of treating amyotrophic lateral sclerosis (ALS), the method comprising:
a) contacting an aqueous pharmaceutical formulation of sodium chlorite with saline to provide a diluted sodium chlorite formulation, wherein the saline is a solution of 0.45% sodium chloride, wherein the diluted sodium chlorite formulation has a volume of 250 mL;
b) administering the diluted sodium chlorite formulation to a subject, wherein the subject has ALS, wherein the administering is by infusion at an infusion site, wherein the infusion is begun as infusion for 30 minutes;
c) during the infusion, determining that the subject experiences pain at the infusion site; and
d) based on the determining that the subject experiences pain at the infusion site, slowing the infusion from 30 minutes to 60 minutes.

2. The method of claim 1, wherein the administering the diluted sodium chlorite formulation to the subject halts loss in vital capacity of the subject.

3. The method of claim 1, wherein the ALS is familial.

4. The method of claim 1, wherein the ALS is sporadic.

5. The method of claim 1, wherein the diluted sodium chlorite formulation is a dosage of 2 mg/kg body weight of the subject.

6. The method of claim 1, wherein the aqueous pharmaceutical formulation of sodium chlorite has a concentration of sodium chlorite of 62 mM.

7. The method of claim 1, wherein the aqueous pharmaceutical formulation of sodium chlorite comprises sodium phosphate.

8. The method of claim 1, wherein the aqueous pharmaceutical formulation of sodium chlorite has a pH of 7.5 to 9.5.

9. The method of claim 1, wherein the aqueous pharmaceutical formulation of sodium chlorite is packaged in a 30 mL glass vial.

10. The method of claim 1, wherein the aqueous pharmaceutical formulation of sodium chlorite is packaged in a 30 mL glass vial with a stopper capped with an overseal.

11. A method of treating amyotrophic lateral sclerosis (ALS), the method comprising:
  a) contacting an aqueous pharmaceutical formulation of sodium chlorite with saline to provide a diluted sodium chlorite formulation, wherein the saline is a solution of 0.45% sodium chloride;
  b) administering to a subject in need thereof the diluted sodium chlorite formulation, wherein the administering is by infusion at an infusion site, wherein the infusion is begun as infusion for 30 minutes;
  c) during the infusion, determining that the subject experiences pain at the infusion site; and
  d) based on the determining that the subject experiences pain at the infusion site, slowing the infusion from 30 minutes to 60 minutes,
  wherein the aqueous pharmaceutical formulation of sodium chlorite has a concentration of sodium chlorite of 62 mM;
  wherein the aqueous pharmaceutical formulation of sodium chlorite comprises sodium phosphate;
  wherein the aqueous pharmaceutical formulation of sodium chlorite has a pH of 7.5 to 9.5;
  wherein the aqueous pharmaceutical formulation of sodium chlorite is packaged in a 30 mL glass vial with a stopper capped with an overseal; and
  wherein the diluted sodium chlorite formulation has a volume of 250 mL.

* * * * *